(12) United States Patent
Peterson

(10) Patent No.: US 8,940,016 B2
(45) Date of Patent: Jan. 27, 2015

(54) MECHANICAL METHOD AND APPARATUS FOR SEQUENTIAL TISSUE FASTENING

(75) Inventor: James A. Peterson, Edina, MN (US)

(73) Assignee: Incisive Surgical, Inc., Plymouth, MN (US)

(*) Notice: Subject to any disclaimer, the term of this patent is extended or adjusted under 35 U.S.C. 154(b) by 337 days.

(21) Appl. No.: 13/324,680

(22) Filed: Dec. 13, 2011

(65) Prior Publication Data

US 2012/0083831 A1 Apr. 5, 2012

Related U.S. Application Data

(62) Division of application No. 11/487,951, filed on Jul. 17, 2006, now Pat. No. 8,100,939.

(60) Provisional application No. 60/699,460, filed on Jul. 15, 2005.

(51) Int. Cl.
*A61B 17/08* (2006.01)
*A61B 17/04* (2006.01)
(Continued)

(52) U.S. Cl.
CPC .......... *A61B 17/08* (2013.01); *A61B 17/0469* (2013.01); *A61B 17/0482* (2013.01); *A61B 17/064* (2013.01); *A61B 17/0644* (2013.01); *A61B 17/0682* (2013.01); *A61B 17/29* (2013.01); *A61B 2017/00004* (2013.01); *A61B 2017/0409* (2013.01); *A61B 2017/0412* (2013.01);
(Continued)

(58) Field of Classification Search
USPC .................. 606/139, 142–144, 151, 213–216
See application file for complete search history.

(56) References Cited

U.S. PATENT DOCUMENTS

| 718,649 A | 1/1903 | Morehouse |
|---|---|---|
| 2,283,814 A | 5/1942 | LaPlace |

(Continued)

FOREIGN PATENT DOCUMENTS

| EP | 1323384 | 7/2003 |
|---|---|---|
| EP | 0657139 | 12/2003 |

(Continued)

OTHER PUBLICATIONS

Brochure: *Information Booklet for Auto Suture® Purse String Instrument*, Auto Suture Company, a division of United States Surgical Corporation, Norwalk, CT, 2 pgs., 1978.
Brochure: *La Sutura Perde it Filo*, Farmitalia Carlo Erba, 4 pgs., not dated.
*Evaluation of New Absorbable Lactomer Subcuticular Staple*, G.C. Zachmann, P.A. Foresman, T.J. Bill, D.J. Bentrem, G.T. Rodeheaver, R.F. Edlich, Journal of Applied Biomaterial, vol. 5, No. 3, pp. 221-116, 1994.
(Continued)

*Primary Examiner* — Gregory Anderson
*Assistant Examiner* — Christina Lauer
(74) *Attorney, Agent, or Firm* — Patterson Thuente Pedersen, P.A.

(57) ABSTRACT

A mechanical system for rotatably, sequentially securing opposing sides of a tissue wound with a fastener. An applicator apparatus is capable of imparting rotatable motion to a falcate tissue penetrator that sequentially pierces and carries a fastener into a first side and a second side of the tissue wound. The first side and second side of tissue can be simultaneously captured and positioned with respect to a tissue definition member or alternatively, the first tissue side and second tissue side can be individually, sequentially captured and positioned relative to the tissue definition member. The applicator apparatus can comprise a single fastener for small tissue wounds or resections or alternatively, the applicator can comprise a plurality of staged fasteners for use in closing a larger wounds or wounds with increased tension.

2 Claims, 57 Drawing Sheets

(51) Int. Cl.
  *A61B 17/064* (2006.01)
  *A61B 17/068* (2006.01)
  *A61B 17/29* (2006.01)
  *A61B 17/00* (2006.01)
  *A61B 17/06* (2006.01)

(52) U.S. Cl.
  CPC . *A61B2017/0419* (2013.01); *A61B 2017/0427* (2013.01); *A61B 2017/06052* (2013.01)
  USPC .......................................................... 606/213

(56) References Cited

U.S. PATENT DOCUMENTS

| | | | |
|---|---|---|---|
| 2,344,071 A | 3/1944 | Wilson et al. |
| 2,351,608 A | 6/1944 | Greenwood |
| 2,439,383 A | 4/1948 | Erickson |
| 2,526,902 A | 10/1950 | Rublee |
| 2,881,762 A | 4/1959 | Lowrie |
| 2,959,172 A | 11/1960 | Held |
| 3,074,409 A | 1/1963 | Bielz |
| 3,082,426 A | 3/1963 | Miles |
| 3,123,077 A | 3/1964 | Alcamo |
| 3,297,033 A | 1/1967 | Schmitt et al. |
| 3,344,790 A | 10/1967 | Dorner |
| 3,570,497 A | 3/1971 | Lemole |
| 3,601,302 A | 8/1971 | Potekhina et al. |
| 3,636,956 A | 1/1972 | Schneider |
| 3,638,654 A | 2/1972 | Akuba |
| 3,643,851 A | 2/1972 | Green et al. |
| 3,716,058 A | 2/1973 | Tanner, Jr. |
| 3,757,629 A | 9/1973 | Schneider |
| 3,792,010 A | 2/1974 | Wasserman et al. |
| 3,858,783 A | 1/1975 | Kapitanov et al. |
| 4,014,492 A | 3/1977 | Rothfuss |
| 4,027,676 A | 6/1977 | Mattei |
| 4,047,533 A | 9/1977 | Perciaccante et al. |
| 4,162,678 A | 7/1979 | Fedotov et al. |
| 4,164,225 A | 8/1979 | Johnson et al. |
| 4,204,541 A | 5/1980 | Kapitanov |
| 4,217,902 A | 8/1980 | March |
| 4,259,959 A | 4/1981 | Walker |
| 4,261,244 A | 4/1981 | Becht et al. |
| 4,317,451 A | 3/1982 | Cerwin et al. |
| 4,345,601 A | 8/1982 | Fukuda |
| 4,354,628 A | 10/1982 | Green |
| 4,396,139 A | 8/1983 | Hall et al. |
| 4,399,810 A | 8/1983 | Samuels et al. |
| 4,407,286 A | 10/1983 | Noiles et al. |
| 4,410,125 A | 10/1983 | Noiles et al. |
| D271,418 S | 11/1983 | Campbell et al. |
| 4,428,376 A | 1/1984 | Mericle |
| 4,430,998 A | 2/1984 | Harvey et al. |
| 4,434,796 A | 3/1984 | Karapetian et al. |
| 4,440,171 A | 4/1984 | Nomoto et al. |
| 4,454,875 A | 6/1984 | Pratt et al. |
| 4,467,805 A | 8/1984 | Fukuda |
| 4,484,580 A | 11/1984 | Nomoto et al. |
| 4,485,816 A | 12/1984 | Krumme |
| 4,485,953 A | 12/1984 | Rothfuss |
| 4,493,322 A | 1/1985 | Becht |
| 4,505,273 A | 3/1985 | Braun et al. |
| 4,506,669 A | 3/1985 | Blake, III |
| D278,656 S | 4/1985 | Green et al. |
| 4,508,253 A | 4/1985 | Green |
| 4,526,173 A | 7/1985 | Sheehan |
| 4,526,174 A | 7/1985 | Froehlich |
| 4,534,352 A | 8/1985 | Korthoff |
| 4,535,772 A | 8/1985 | Sheehan |
| 4,548,202 A | 10/1985 | Duncan |
| 4,557,265 A | 12/1985 | Andersson |
| 4,566,620 A | 1/1986 | Green et al. |
| 4,568,009 A | 2/1986 | Green |
| 4,570,623 A | 2/1986 | Ellison et al. |
| 4,573,622 A | 3/1986 | Green et al. |
| 4,583,670 A | 4/1986 | Alvarado |
| 4,592,498 A | 6/1986 | Braun et al. |
| 4,593,843 A | 6/1986 | Saravis |
| 4,596,249 A | 6/1986 | Freda et al. |
| 4,596,350 A | 6/1986 | Smith et al. |
| 4,603,693 A | 8/1986 | Conta et al. |
| 4,607,638 A | 8/1986 | Crainich |
| 4,610,251 A | 9/1986 | Kumar |
| 4,618,086 A | 10/1986 | Li et al. |
| 4,619,262 A | 10/1986 | Taylor |
| D287,630 S | 1/1987 | Sharkany et al. |
| 4,637,380 A | 1/1987 | Orejola |
| 4,646,741 A | 3/1987 | Smith |
| 4,655,222 A | 4/1987 | Florez et al. |
| 4,665,916 A | 5/1987 | Green |
| 4,671,279 A | 6/1987 | Hill |
| 4,676,245 A | 6/1987 | Fukuda |
| 4,696,300 A | 9/1987 | Anderson |
| 4,719,917 A | 1/1988 | Barrows et al. |
| 4,724,840 A * | 2/1988 | McVay et al. .................. 606/215 |
| 4,728,020 A | 3/1988 | Green et al. |
| 4,741,337 A | 5/1988 | Smith et al. |
| 4,752,024 A | 6/1988 | Green et al. |
| 4,753,636 A | 6/1988 | Free |
| 4,762,260 A | 8/1988 | Richards et al. |
| 4,776,506 A | 10/1988 | Green |
| 4,789,090 A | 12/1988 | Blake, III |
| 4,799,483 A | 1/1989 | Kraff |
| 4,802,478 A | 2/1989 | Powell |
| 4,809,695 A | 3/1989 | Gwathmey et al. |
| 4,869,414 A | 9/1989 | Green et al. |
| 4,873,976 A | 10/1989 | Schreiber |
| 4,887,601 A | 12/1989 | Richards |
| 4,887,756 A | 12/1989 | Puchy |
| 4,895,148 A | 1/1990 | Bays et al. |
| 4,899,745 A | 2/1990 | Laboureau et al. |
| 4,915,100 A | 4/1990 | Green |
| 4,924,866 A | 5/1990 | Yoon |
| 4,932,960 A | 6/1990 | Green et al. |
| 4,938,408 A | 7/1990 | Bedi et al. |
| 4,955,898 A | 9/1990 | Matsutani et al. |
| 4,969,591 A | 11/1990 | Richards et al. |
| 4,976,686 A | 12/1990 | Ball et al. |
| 4,976,715 A | 12/1990 | Bays et al. |
| 4,979,954 A | 12/1990 | Gwathmey et al. |
| 4,981,149 A | 1/1991 | Yoon et al. |
| 4,994,073 A | 2/1991 | Green |
| 5,002,562 A | 3/1991 | Oberlander |
| 5,002,563 A | 3/1991 | Pyka |
| 5,007,921 A | 4/1991 | Brown |
| 5,015,252 A | 5/1991 | Jones |
| 5,026,390 A | 6/1991 | Brown |
| 5,035,692 A | 7/1991 | Lyon et al. |
| 5,041,128 A | 8/1991 | Korthoff |
| 5,044,540 A | 9/1991 | Dulebohn |
| 5,047,047 A | 9/1991 | Yoon |
| 5,053,047 A | 10/1991 | Yoon |
| 5,058,315 A | 10/1991 | Wagner |
| 5,062,563 A | 11/1991 | Green et al. |
| 5,067,959 A | 11/1991 | Korthoff |
| 5,078,731 A | 1/1992 | Hayhurst |
| 5,080,665 A | 1/1992 | Jarrett et al. |
| 5,084,063 A | 1/1992 | Korthoff |
| 5,089,009 A | 2/1992 | Green |
| 5,089,010 A | 2/1992 | Korthoff |
| 5,089,011 A | 2/1992 | Korthoff |
| 5,108,422 A | 4/1992 | Green et al. |
| 5,123,913 A | 6/1992 | Wilk et al. |
| 5,129,570 A | 7/1992 | Schulze et al. |
| 5,133,738 A | 7/1992 | Korthoff et al. |
| 5,139,514 A | 8/1992 | Korthoff et al. |
| 5,156,315 A | 10/1992 | Green et al. |
| 5,156,609 A | 10/1992 | Nakao et al. |
| 5,156,615 A | 10/1992 | Korthoff et al. |
| 5,158,566 A | 10/1992 | Pianetti |
| 5,158,567 A | 10/1992 | Green |
| 5,160,339 A | 11/1992 | Chen et al. |
| 5,176,306 A | 1/1993 | Heimerl et al. |
| 5,179,964 A | 1/1993 | Cook |
| 5,211,644 A | 5/1993 | VanBeek et al. |

(56) References Cited

U.S. PATENT DOCUMENTS

| | | | |
|---|---|---|---|
| 5,211,722 A | 5/1993 | Wagner | |
| 5,222,976 A | 6/1993 | Yoon | |
| 5,226,912 A | 7/1993 | Kaplan et al. | |
| 5,236,440 A | 8/1993 | Hlavacek | |
| 5,242,457 A | 9/1993 | Akopov et al. | |
| 5,257,713 A | 11/1993 | Green et al. | |
| 5,258,009 A | 11/1993 | Conners | |
| 5,258,010 A | 11/1993 | Green et al. | |
| 5,258,012 A | 11/1993 | Luscombe et al. | |
| 5,259,845 A | 11/1993 | Korthoff | |
| 5,263,973 A | 11/1993 | Cook | |
| 5,269,783 A | 12/1993 | Sander | |
| 5,269,792 A | 12/1993 | Kovac et al. | |
| 5,275,166 A | 1/1994 | Vaitekunas et al. | |
| 5,282,807 A | 2/1994 | Knoepfler | |
| 5,285,944 A | 2/1994 | Green et al. | |
| 5,292,326 A | 3/1994 | Green et al. | |
| 5,293,881 A | 3/1994 | Green et al. | |
| 5,297,714 A | 3/1994 | Kramer | |
| 5,304,204 A | 4/1994 | Bregen | |
| 5,306,281 A * | 4/1994 | Beurrier | 606/144 |
| 5,324,307 A | 6/1994 | Jarrett et al. | |
| 5,330,503 A | 7/1994 | Yoon | |
| 5,333,772 A | 8/1994 | Rothfuss et al. | |
| 5,337,937 A | 8/1994 | Remiszewski et al. | |
| 5,342,376 A | 8/1994 | Ruff | |
| 5,350,400 A | 9/1994 | Esposito et al. | |
| 5,356,424 A | 10/1994 | Buzerak et al. | |
| 5,364,003 A | 11/1994 | Williamson, IV | |
| 5,366,134 A | 11/1994 | Green et al. | |
| 5,389,102 A | 2/1995 | Green et al. | |
| 5,392,979 A | 2/1995 | Green et al. | |
| 5,398,861 A | 3/1995 | Green | |
| D357,316 S | 4/1995 | Green et al. | |
| 5,413,584 A | 5/1995 | Schulze | |
| 5,415,334 A | 5/1995 | Williamson, IV et al. | |
| 5,417,361 A | 5/1995 | Williamson, IV | |
| 5,423,856 A | 6/1995 | Green | |
| 5,456,400 A | 10/1995 | Shichman et al. | |
| 5,456,401 A | 10/1995 | Green et al. | |
| 5,478,003 A | 12/1995 | Green et al. | |
| 5,480,089 A | 1/1996 | Blewett | |
| 5,482,197 A | 1/1996 | Green et al. | |
| 5,484,095 A | 1/1996 | Greer et al. | |
| 5,489,058 A | 2/1996 | Plyley et al. | |
| 5,489,287 A | 2/1996 | Green et al. | |
| 5,499,990 A | 3/1996 | Schulken et al. | |
| 5,505,363 A | 4/1996 | Green et al. | |
| 5,509,596 A | 4/1996 | Green et al. | |
| 5,514,149 A | 5/1996 | Green et al. | |
| 5,542,594 A | 8/1996 | McKean et al. | |
| 5,544,802 A | 8/1996 | Crainich | |
| 5,549,619 A | 8/1996 | Peters et al. | |
| 5,551,622 A | 9/1996 | Yoon | |
| 5,558,266 A | 9/1996 | Green et al. | |
| 5,562,241 A | 10/1996 | Knodel et al. | |
| 5,571,285 A | 11/1996 | Chow et al. | |
| 5,573,541 A | 11/1996 | Green et al. | |
| 5,573,542 A | 11/1996 | Stevens | |
| 5,575,800 A | 11/1996 | Gordon | |
| 5,579,978 A | 12/1996 | Green et al. | |
| 5,584,859 A | 12/1996 | Brotz | |
| 5,591,178 A | 1/1997 | Green et al. | |
| 5,593,423 A | 1/1997 | Person et al. | |
| 5,618,311 A | 4/1997 | Gryskiewicz | |
| 5,645,567 A | 7/1997 | Crainich | |
| 5,655,698 A | 8/1997 | Yoon | |
| 5,658,312 A | 8/1997 | Green et al. | |
| 5,662,258 A | 9/1997 | Knodel et al. | |
| 5,662,655 A | 9/1997 | Laboureau et al. | |
| 5,667,527 A | 9/1997 | Cook | |
| 5,706,997 A | 1/1998 | Green et al. | |
| 5,722,981 A | 3/1998 | Stevens | |
| 5,725,538 A | 3/1998 | Green et al. | |
| 5,725,554 A | 3/1998 | Simon et al. | |
| 5,728,108 A | 3/1998 | Griffiths et al. | |
| 5,741,278 A | 4/1998 | Stevens | |
| 5,782,844 A | 7/1998 | Yoon et al. | |
| 5,792,152 A | 8/1998 | Klein et al. | |
| 5,794,834 A | 8/1998 | Hamblin et al. | |
| 5,816,471 A | 10/1998 | Plyley et al. | |
| 5,829,662 A | 11/1998 | Allen et al. | |
| 5,843,084 A | 12/1998 | Hart et al. | |
| 5,871,135 A | 2/1999 | Williamson, IV et al. | |
| 5,878,937 A | 3/1999 | Green et al. | |
| 5,902,311 A | 5/1999 | Andreas et al. | |
| 5,902,319 A | 5/1999 | Daley | |
| 5,908,149 A | 6/1999 | Welch et al. | |
| 5,908,427 A | 6/1999 | McKean et al. | |
| 5,921,994 A | 7/1999 | Andreas et al. | |
| 5,947,999 A | 9/1999 | Groiso | |
| 5,964,774 A | 10/1999 | McKean et al. | |
| 5,976,160 A | 11/1999 | Crainich | |
| 5,984,949 A | 11/1999 | Levin | |
| 5,993,476 A | 11/1999 | Groiso | |
| 6,036,699 A | 3/2000 | Andreas et al. | |
| 6,036,701 A | 3/2000 | Rosenman | |
| 6,039,753 A * | 3/2000 | Meislin | 606/213 |
| 6,045,560 A | 4/2000 | McKean et al. | |
| 6,083,242 A | 7/2000 | Cook | |
| 6,090,131 A | 7/2000 | Daley | |
| 6,120,526 A | 9/2000 | Daley | |
| 6,131,789 A | 10/2000 | Schulze et al. | |
| 6,136,010 A | 10/2000 | Modesitt et al. | |
| 6,149,658 A | 11/2000 | Gardiner et al. | |
| 6,159,224 A | 12/2000 | Yoon | |
| 6,241,747 B1 | 6/2001 | Ruff | |
| 6,250,532 B1 | 6/2001 | Green et al. | |
| 6,270,517 B1 | 8/2001 | Brotz | |
| 6,325,805 B1 | 12/2001 | Ogilvie et al. | |
| 6,387,104 B1 | 5/2002 | Pugsley, Jr. et al. | |
| 6,387,113 B1 | 5/2002 | Hawkins et al. | |
| 6,409,743 B1 | 6/2002 | Fenton, Jr. | |
| 6,423,088 B1 | 7/2002 | Fenton, Jr. | |
| 6,443,962 B1 * | 9/2002 | Gaber | 606/144 |
| 6,514,263 B1 | 2/2003 | Stefanchik et al. | |
| 6,530,933 B1 | 3/2003 | Yeung et al. | |
| 6,599,310 B2 | 7/2003 | Leung et al. | |
| 6,601,748 B1 | 8/2003 | Fung et al. | |
| 6,619,529 B2 | 9/2003 | Green et al. | |
| 6,626,916 B1 | 9/2003 | Yeung et al. | |
| 6,629,988 B2 | 10/2003 | Weadock | |
| 6,638,297 B1 | 10/2003 | Huitema | |
| 6,652,538 B2 | 11/2003 | Kayan et al. | |
| 6,666,872 B2 | 12/2003 | Barreiro et al. | |
| 6,726,705 B2 | 4/2004 | Peterson et al. | |
| 6,767,356 B2 | 7/2004 | Kanner et al. | |
| 6,773,437 B2 | 8/2004 | Ogilvie et al. | |
| 7,112,214 B2 | 9/2006 | Peterson et al. | |
| D532,107 S | 11/2006 | Peterson et al. | |
| 7,547,315 B2 | 6/2009 | Peterson et al. | |
| 8,100,939 B2 | 1/2012 | Peterson | |
| 2002/0007184 A1 | 1/2002 | Ogilvie et al. | |
| 2002/0019636 A1 | 2/2002 | Ogilvie et al. | |
| 2002/0133181 A1 | 9/2002 | Tong | |
| 2003/0028218 A1 | 2/2003 | Bauer | |
| 2003/0139746 A1 | 7/2003 | Groiso | |
| 2003/0233108 A1 * | 12/2003 | Gellman et al. | 606/144 |
| 2003/0236550 A1 | 12/2003 | Peterson et al. | |
| 2003/0236551 A1 | 12/2003 | Peterson | |
| 2004/0059377 A1 | 3/2004 | Peterson et al. | |
| 2004/0059378 A1 | 3/2004 | Peterson et al. | |
| 2005/0033317 A1 | 2/2005 | Ables | |
| 2005/0085857 A1 | 4/2005 | Peterson et al. | |
| 2005/0149064 A1 | 7/2005 | Peterson et al. | |
| 2005/0182444 A1 | 8/2005 | Peterson et al. | |
| 2006/0135988 A1 | 6/2006 | Peterson | |

FOREIGN PATENT DOCUMENTS

| | | |
|---|---|---|
| FR | 2549544 A3 | 1/1985 |
| JP | 5-504892 | 7/1993 |
| JP | H6-233772 | 8/1994 |
| JP | 7124166 A | 5/1995 |

(56) References Cited

FOREIGN PATENT DOCUMENTS

| | | |
|---|---|---|
| JP | 2000217829 A | 8/2000 |
| WO | WO 0057796 A1 | 10/2000 |
| WO | WO 0067644 A1 | 11/2000 |

OTHER PUBLICATIONS

Suturtek Incorporated, http://wvvw.suturtek.com/productInfo/, Jan. 31, 2007, p. 1 of 1, North Chelmsford, Massachusetts.

* cited by examiner

FIG. 44
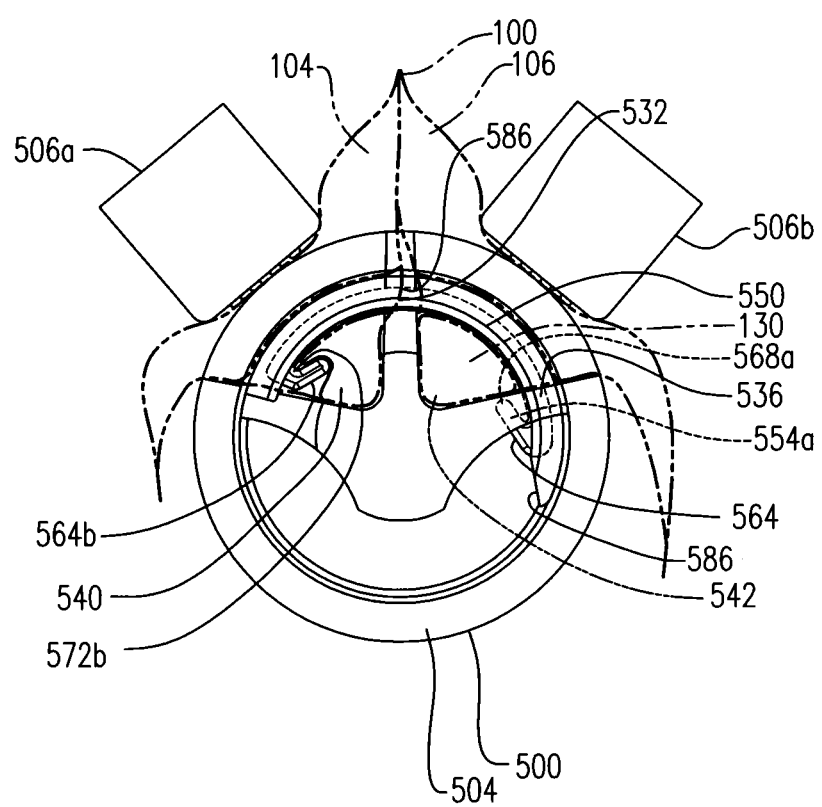
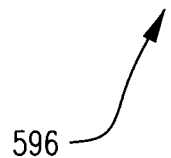

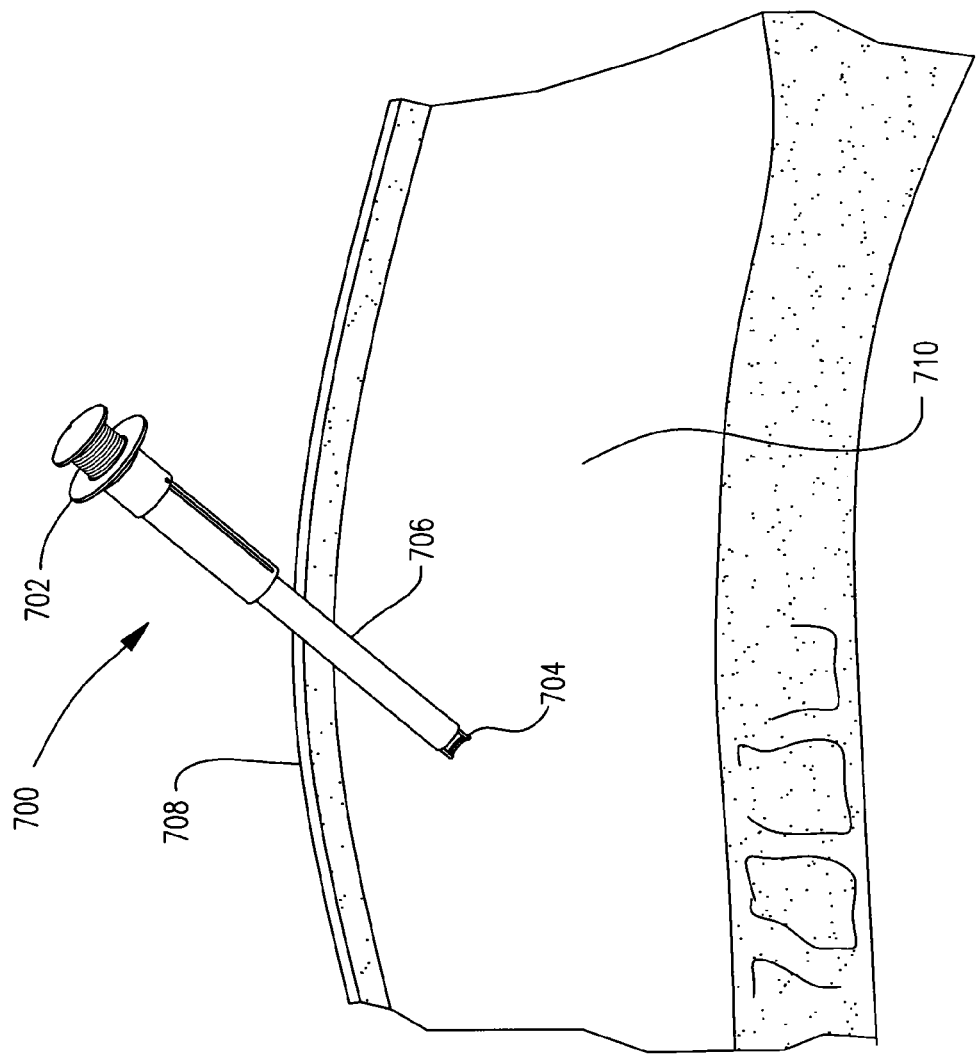

MECHANICAL METHOD AND APPARATUS FOR SEQUENTIAL TISSUE FASTENING

RELATED APPLICATION

This application is a division of application Ser. No. 11/487,951 filed Jul. 17, 2006, now U.S. Pat. No. 8,100,939 which claims the benefit of U.S. Provisional Application No. 60/699,460 filed Jul. 15, 2005, each of which is hereby fully incorporated herein by reference.

FIELD OF THE INVENTION

The present invention relates generally to the field of surgical instruments such as surgical staplers, clip applicators and sutureless closure devices. More particularly, the present invention relates to a mechanical method and apparatus for fastening tissue by rotatably, sequentially securing opposed sides of a tissue wound.

BACKGROUND OF THE INVENTION

When an opening in tissue is created either through an intentional incision or an accidental wound or laceration, biological healing of the opening commences through the proximity of the opposed living tissue surfaces. If the opening is very large or if its location subjects the wound to continual movement, a physician will seek to forcibly hold the sides of the opening in close proximity so as to promote the healing process.

In the case of skin tissue, for example, healing occurs best when the opposing dermal layers of the skin tissue are held in proximity with each other. Human skin tissue is comprised of three distinct layers of tissue. The epidermal layer, also known as the epidermis, is the outermost layer and includes non-living tissue cells. The dermal layer, or dermis, is the middle layer directly below the epidermal layer and comprises the living tissue of the skin that is the strongest of the three layers. The subcutaneous, or hypodermis layer is the bottom layer of skin tissue and includes less connective tissue making this the weakest layer of skin tissue.

The most prevalent method for forcibly closing a tissue opening is through the use of a suture or "stitches." As early as the second century, the Greeks were using sutures to physically close skin openings. In its simplest form, a suture is simply a length of material that is attached to a tissue-piercing device, such as a needle, and looped through the opposing sides of an opening. The suture is then pulled tight and the loop closes causing the opposing sides of the tissue to come into close physical proximity. The suture loop is held tight by the tying of a knot or some other locking mechanism. The first sutures were made of animal gut. Eventually other natural suture materials including leather, horsehair, flax, cotton and silk came into use.

As the sciences of medical and materials technology have advanced over the course of the past century, new bioabsorbable materials have been developed to further improve upon the basic suturing concept. Examples of more recent improvements to the suturing process include enhancements to the suturing apparatus as shown, for example, in U.S. Pat. Nos. 2,439,383, 2,959,172 and 3,344,790, as well as advances in sutures and suture materials as shown, for example, in U.S. Pat. Nos. 3,123,077, 3,297,033, 3,636,956, 3,792,010 4,027,676 and 4,047,533.

While traditional suturing remains a popular method of effectuating closure of skin openings, the use of staples and staplers as a skin closure technique has become increasingly popular, especially in surgical settings where the opening is created through a purposeful incision. In these settings, the incision tends to make a clean, straight cut with the opposing sides of the incision having consistent and non-jagged surfaces. Typically, stapling of a skin opening, for example, is accomplished by manually approximating the opposing sides of the skin opening and then positioning the stapler so that a staple will span the opening. The stapler is then manipulated such that the staple is driven into the skin with one leg being driven into each side of the skin and the cross-member of the staple extending across the opening external to the skin surface. Generally, the legs of the staple are driven into an anvil causing the staple to deform so as to retain the skin tissue in a compressed manner within the staple. This process can be repeated along the length of the opening such that the entire incision is held closed during the healing process.

Much work has been devoted to improving upon the basic stapling process. Developments have gone in a variety of directions and include work devoted to the stapling apparatus as shown, for example, in U.S. Pat. Nos. 3,082,426, 3,643,851, 4,410,125, 4,493,322, 4,592,498, 4,618,086, 4,776,506, 4,915,100, 5,044,540, 5,129,570, 5,285,944, 5,392,979, 5,489,058, 5,551,622, 5,662,258, 5,794,834, 5,816,471, 6,131,789 and 6,250,532. In addition to the stapling apparatus, developments have also been made in the staple design as shown, for example, in U.S. Pat. Nos. 2,351,608, 2,526,902, 2,881,762, 3,757,629, 4,014,492, 4,261,244, 4,317,451, 4,407,286, 4,428,376, 4,485,816, 4,505,273, 4,526,174, 4,570,623, 4,719,917, 4,741,337, 5,007,921, 5,158,567, 5,258,009, 5,297,714, 5,324,307, 5,413,584, 5,505,363 and 5,571,285.

While suturing and stapling techniques continue to provide an effective manner of effectuating skin closure, there remains a series of inherent disadvantages in using either of these techniques. The standard technique for both suturing and stapling includes puncturing both the epidermis and dermis. This can result in a wound closure causing patient discomfort and having an unaesthetically pleasing appearance on the surface of the skin. The presence of the fastener exposed through the skin surface provides an opportunity for infection and for accidentally catching the fastener and tearing the wound open. In the case of non-absorbable fasteners, further action by a medical professional is necessary in order to remove the fastener once biological healing is complete.

In order to overcome these limitations, practitioners have developed a number of specialized suturing techniques where the suture is passed only through the dermis effectively positioning the suture below the skin surface, or in a subcuticular fashion. A surgeon has the choice of placing individual or interrupted sutures along the length of an opening. Another suturing option is for the surgeon to use a single strand of suture material to place a plurality of continuing suture loops or running sutures along the length of an opening. While the presence of the suture below the surface can improve the aesthetic nature of the closure, it requires greater skill and technique to accomplish effectively and takes longer than conventional external suturing.

While there has been active development of dermal layer suturing techniques, little has been done in the area of staples and staplers for use in connection with the dermal layer. In a series of patents issued to Green et al., including U.S. Pat. Nos. 5,292,326, 5,389,102, 5,489,287 and 5,573,541, a subcuticular stapling method and apparatus are disclosed that were ultimately commercialized as the U.S. Surgical SQS Subcuticular Stapling Apparatus. The Green et al. patents describe a stapling technique employing a handheld apparatus with jaws to proximate, interdigitate and overlap opposing sides of dermal layer tissue along the length of a skin opening. The apparatus then drives a single spike through the interdigitated and overlapped dermal layers of the opposing skin surfaces in order to secure both sides of the dermal tissue on the single spike. Although this technique reduced the time required to effectuate a subcuticular skin closure, the SQS device was not commercially successful in part because it was difficult to achieve a secure uniform closure and the resulting closure produced an undesirable wave-like closure with gaps that sometimes did not heal effectively.

A novel approach to fastening dermal tissue using bioabsorbable fasteners is disclosed and described in U.S. Pat. No. 6,726,705, as well as in U.S. Publ. Nos. US2003-0236551 A1, US2004-0059377 A1 and US2004-0059378 A1 to Peterson et al, all of which are commonly assigned to the assignee of the present application and all of which are incorporated by reference in their entirety. In one embodiment, this approach to tissue fastening utilizes a first apparatus to manipulate opposed sides of tissue to form target tissue zones followed by a second apparatus that effects a simultaneous bilateral insertion of a tissue fastener to retain opposed dermal layers across an incision or wound in close approximation to facilitate healing. By maintaining contact of the dermal layers through the healing process, the healing process is enhanced which results in less chance of infection, faster recovery and improved aesthetic appearance. In addition, no subsequent medical follow-up is necessary to remove fasteners as is typically necessary with non-absorbable fasteners.

While the tissue fastening methods and apparatus taught by Peterson et al. provide many advantages, there are opportunities to improve upon the principles taught by Peterson et al. with respect to tissue fastening applications. For example, it would be desirable to provide for a fastening apparatus providing for increased simplicity in manufacturing and implementation.

SUMMARY OF THE INVENTION

The present invention is a mechanical system for rotatably, sequentially securing opposed sides of a tissue wound. An applicator apparatus includes an insertion head portion positioned proximate a tissue wound. Utilizing a tissue manipulator, a first side of tissue is positioned within a first receiving portion on the insertion head. A rotatable drive mechanism rotatably inserts a first cleat portion of a fastener through a portion of the first side of tissue. The tissue manipulator releases the first side of tissue and manipulates a second side of tissue such that it is positioned within a second receiving portion on the insertion head. The rotatable drive mechanism rotatably inserts the first cleat portion of the fastener though a portion of the second side of tissue while substantially simultaneously capturing the first side of tissue with a trailing second cleat portion of the fastener. Following capture of the both the first and second tissue sides with the fastener, the rotatable drive mechanism is reversibly rotated such that the insertion head can be removed from the tissue wound while the fastener retainably approximates the first and second tissue sides so as accomplish the wound closure.

In one aspect, the present application is directed to an apparatus for sequentially, rotatably inserting a fastener into the dermal layer on opposed sides of a tissue wound.

In another aspect, the present application is directed to a fastener adapted for rotatable insertion into the dermal layer of opposed sides of a tissue wound.

In another aspect, the present invention is directed to methods for closing tissue wounds through rotatable, sequentially positioning of a tissue fastener across the tissue wound.

In another aspect, the present invention is directed to a laproscopic tissue fastening device for joining tissue wounds through rotatable, sequential positioning of a laproscopic tissue fastener.

BRIEF DESCRIPTION OF THE DRAWINGS

FIG. 39a is a perspective view of an alternative embodiment of an insertion member and fastener of the tissue fastening device of FIG. 37a.

FIG. 44 is an end view of the fastening end of the tissue fastening device of FIG. 37 during a fourth fastening step for closing a skin wound.

FIG. 51 is a perspective view of an embodiment of a minimally invasive tissue fastening device.

DETAILED DESCRIPTION OF THE EMBODIMENTS

Figure 1:
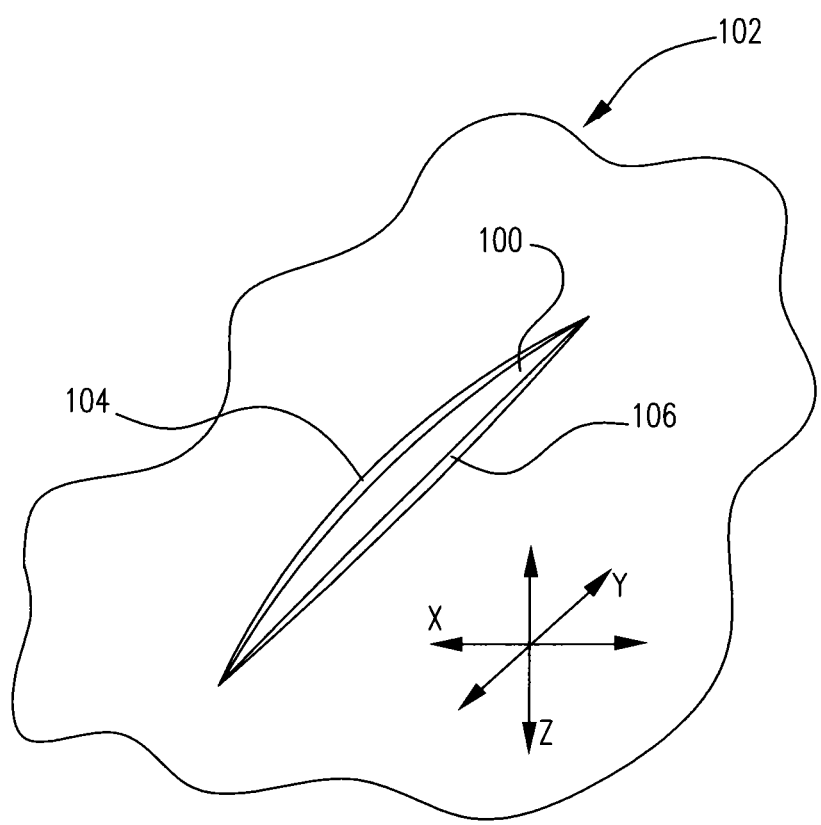
FIG. 1 is a perspective view of a representative tissue opening in a skin surface.
Figure 2:
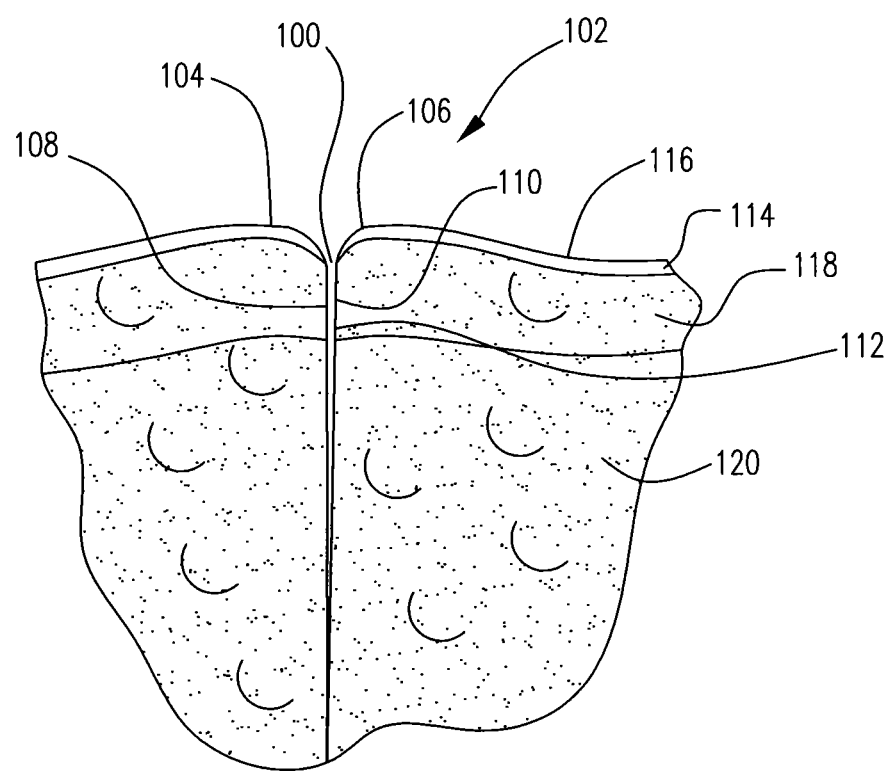
FIG. 2 is a section view of the representative tissue opening of FIG. 1.

In FIGS. 1 and 2, there is shown a depiction of a typical opening 100 in the surface of skin 102, such as may be made, for example, by a surgical incision or a wound. Opening 100 defines a first side 104 and a second side 106 on opposed sides of the opening 100. First side 104 and second side 106 can comprise a substantially parallel arrangement as illustrated in FIG. 1, or alternatively, first side 104 and second side 106 comprise substantially non-parallel portions such as commonly associated with wounds as opposed to surgical incisions. As illustrated in FIG. 1, for purposes of describing the present invention, opening 100 may be described as having a length or longitudinal orientation parallel to the y-y axis, a width orientation parallel to the x-x axis, and a depth orientation parallel to the z-z axis. The x-y-z axis, for purposes of one embodiment of the present invention, is defined with respect to an external tissue surface, which in the case of skin 102 is the outer surface. References to a vertical and horizontal planar orientation in connection with the present invention are made with respect to the external tissue surface at the site of the opening in question. As described herein, opening 100 can have a length from about 8 mm, which can reflect surgical procedures such as, for example, a mole resection, to about 60 cm, which can reflect surgical procedures such as, for example, an abdominoplasty.

As illustrated in FIG. 2, in one embodiment, a first vertical inner surface 108 associated with first side 104 and a second vertical inner surface 110 associated with second side 106 can be visualized as meeting along a generally vertical interface 112. It will be understood that in the case of an opening that extends over a curved tissue surface, the corresponding horizontal and vertical surfaces associated with the opening will be defined with respect to such curved tissue surface. It also will be understood that the vertical interface 112 may be vertical in only one orientation with respect to the tissue surface, such as in the case when an angled incision has formed the opening 100.

Figure 3:
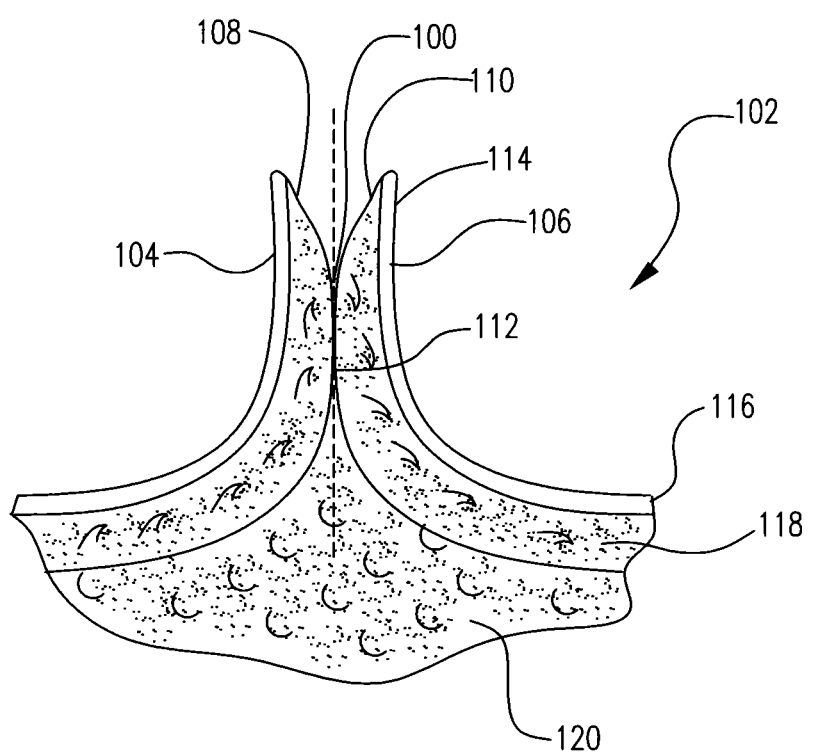
FIG. 3 is a section view of the representative tissue opening of FIG. 1 in a substantially everted disposition.

As illustrated in the sectional view of FIGS. 2 and 3, human skin 102 generally has three discrete layers. These layers comprise an epidermal layer 114 of mostly non-living tissue having an exterior surface 116, a dermal layer 118 of mostly living tissue, and a subcutaneous tissue layer 120. Although certain representative embodiments of the present invention will be described with respect to human skin tissue 102, it will be understood that the present invention is applicable to closure of openings in other types of tissue having generally defined surfaces with membranes, layers or wall such as, for example, fascia, membranes, organs, vessels, vasculature, vascular pedicles, skin grafts, bladder and other biocompatible materials with generally defined surfaces also having membranes, layers or walls such as, for example, artificial skin, artificial membranes and synthetic mesh.

It has long been known that the most rapid healing of a skin opening 100 with a minimum of scarring occurs when vertical inner surfaces 108, 110 of the living dermal layer 118 at each side of the vertical interface 112 of skin opening 100 are brought together and held in close contact in what is referred to as an everted position as is shown in exaggerated fashion in FIG. 3. To the extent that the primarily non-living material of epidermal layer 114 can be excluded from the healing opening, the rapidity and level of scar tissue formed during the healing process will be minimized.

Figure 5:
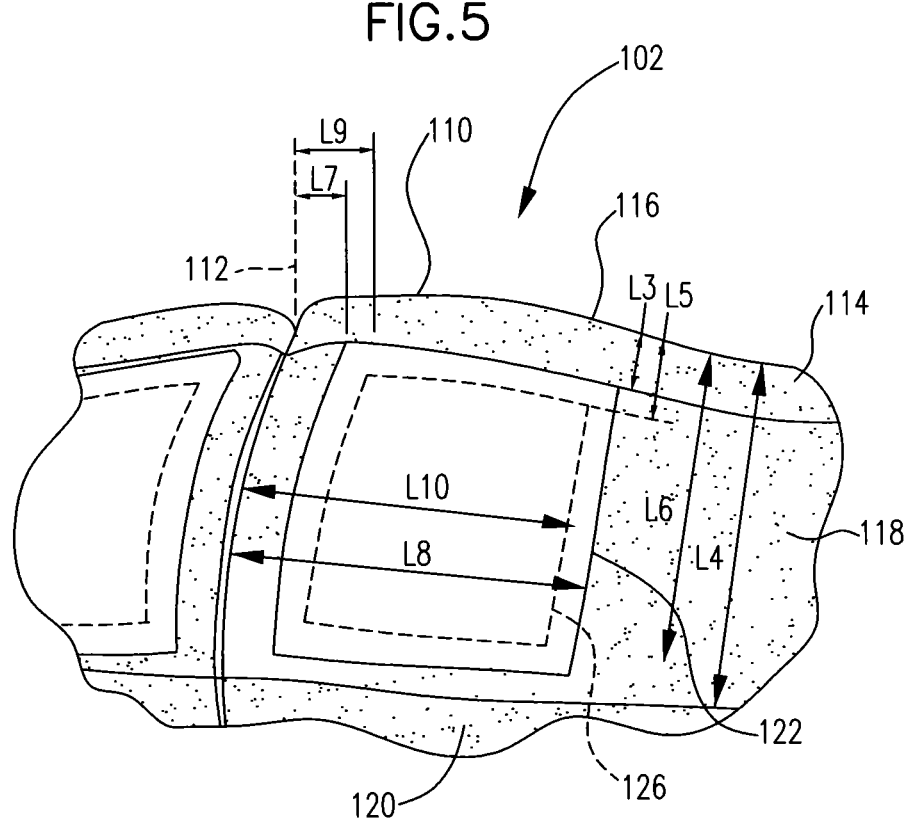
FIG. 5 is a top view of a representative wound closure accomplished using a prior art surgical stapling method.
Figure 4:
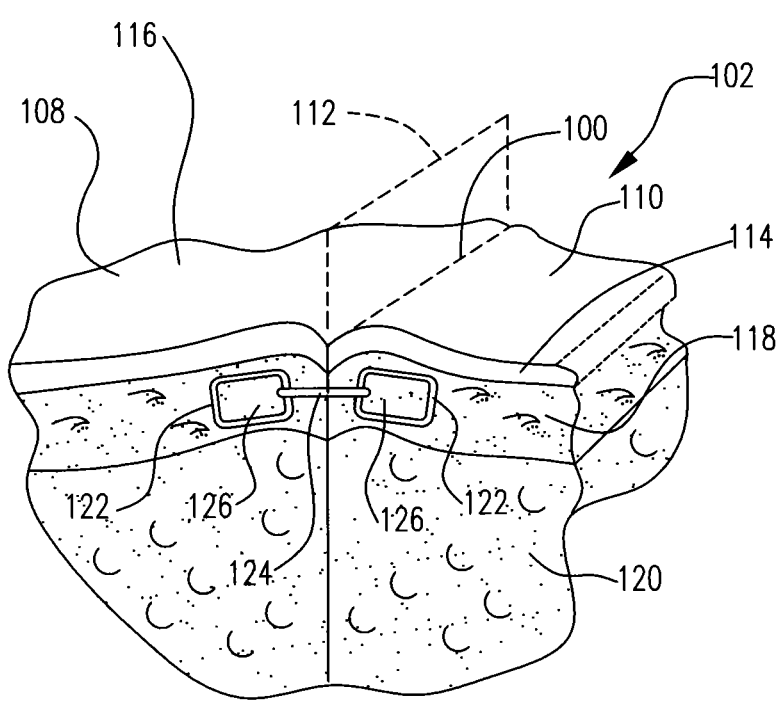
FIG. 4 is a top view of a representative wound closure accomplished using a prior art subcuticular stitching method.

With respect to skin opening 100 as illustrated in FIGS. 4 and 5, there exists an optimal target tissue zone 122 on each side of vertical interface 112 for placement of a fastener 124 in order to achieve optimal dermal contact for healing. As described in the previously referenced and incorporated Peterson et al. patent documents, one method by which these target tissue zones 122 can be presented and accessed is through a bilateral capture and fastening process. With respect to the present disclosure, a method for rotabably, sequentially presenting and accessing these same target tissue zones via a generally circular path of travel is defined. In addition, the present rotatatable, sequential methods and apparatus disclosed herein permit the path of travel to and through the target tissue zones to be accomplished at a variety of angles and orientations making placement of the fastener 124 convenient to the medical professional. In addition, the rotatable, sequential nature of the presently disclosed apparatus and systems provide for an easily scalable system allowing for easy adaptation of system dimensionality for a variety of surgical procedures including different type of tissue having generally define surfaces.

As illustrated in FIGS. 4 and 5, target tissue zone 122 for a skin closure lies within the dermal layer 118, and can be visualized as a rectangular cross-sectional area when the tissue is in a relaxed condition. In addition, within each target tissue zone 122, there exists a most preferred area 126 for tissue engagement. In the depth orientation, target tissue zone 122 lays between a distance L3 of about 0.1 mm below the exterior surface 116 of epidermal layer 114, and a distance L4 up to 2.0 mm below the exterior surface 116. The most preferred area 126 lies between a distance L5 of about 0.2 mm and a distance L6 of about 0.8 mm below the exterior surface 116. In the width orientation, target tissue zone 122 lies between a distance L7 of about 1.0 mm and a distance L8 of about 20.0 mm from vertical interface 112. Most preferred area 126 lies between a distance L9 of about 2.0 mm and a distance L10 of about 8.0 mm from vertical interface 112. Because the target tissue zone 122 is not visible to an operator, a tissue manipulator assembly and rotatable applicator assembly are preferably designed to consistently and repeatedly enable the operator to position the target tissue zone 122 for deployment of a fastener 124 as will be subsequently described.

Figure 6:
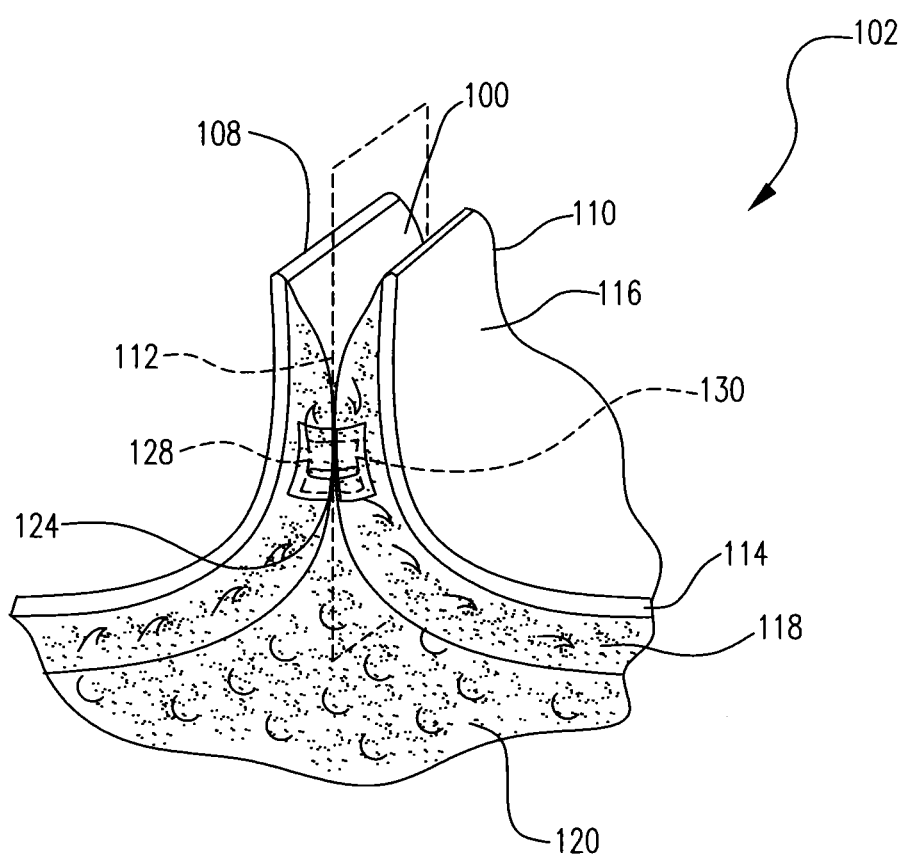
FIG. 6 is a top view of a representative wound closure accomplished using a prior art subcuticular, rod-like fastener method.

As illustrated in FIG. 6, the advantages of the various embodiments of the present invention are accomplished by an apparatus and method that rotatably, sequentially engage the target tissue zones 122, hereafter referred to as a first target tissue zone 128 associated with first side 108 and a second target tissue zone 130 associated with second side 110, on each side of a skin opening 100 with fastener 124 that is preferably made of a bioabsorbable material. The location, geometry and orientation of the fastener and the dermal layers in relation to the mechanical apparatus of the present invention are all important considerations to obtaining the most optimal contact and compression of the dermal layer for efficacious closing of the opening in this embodiment. While the skin opening 100 will be described in connection with an opening in a single piece of tissue, it will be understood that the opening 100 could also be between two separate and otherwise unconnected pieces of tissue, or even between a piece of tissue and a piece of biocompatible material to be secured to that piece of tissue. In addition, the methods and systems of the present invention are applicable to a wide variety of sizes and configurations for skin opening 100, such as, for example, the lengthy, purposeful incisions associated with surgical procedures such as removing excess skin after bariatric surgery or for very small openings associated with procedures such as a mole resection.

Figure 7:
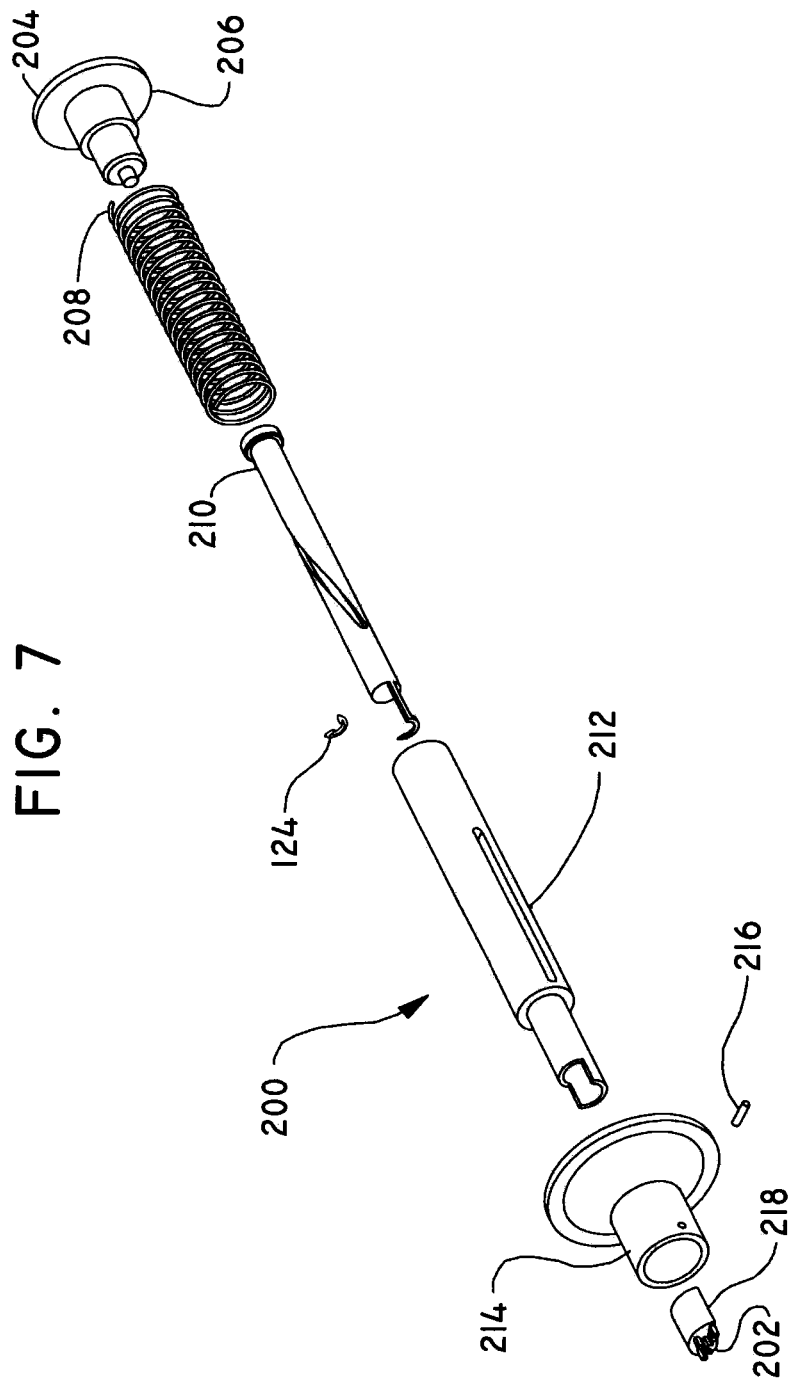
FIG. 7 is an exploded, perspective view of an embodiment of a tissue closure device.
Figure 8:
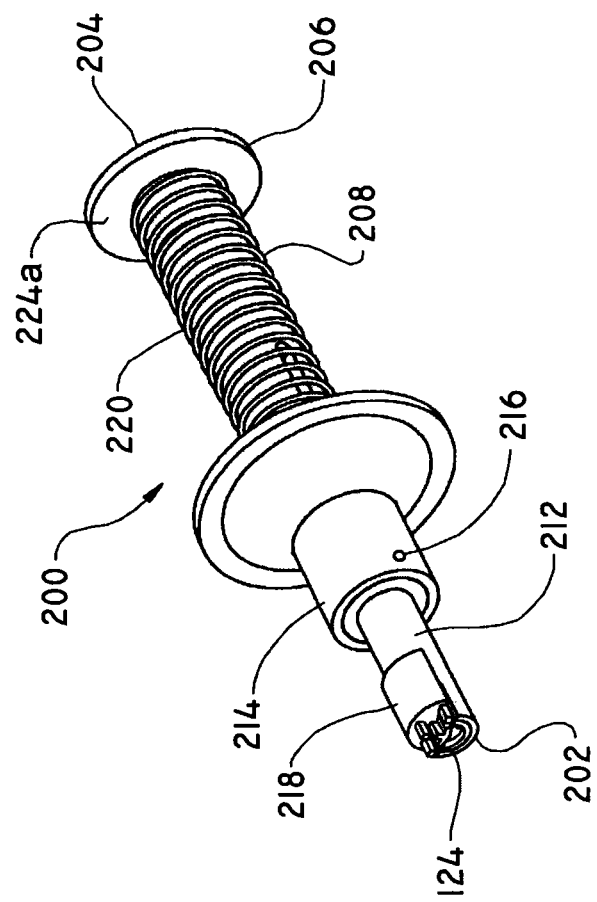
FIG. 8 is a perspective view of the tissue closure device of FIG. 7 in a pre-fastener deployment configuration.
Figure 9:
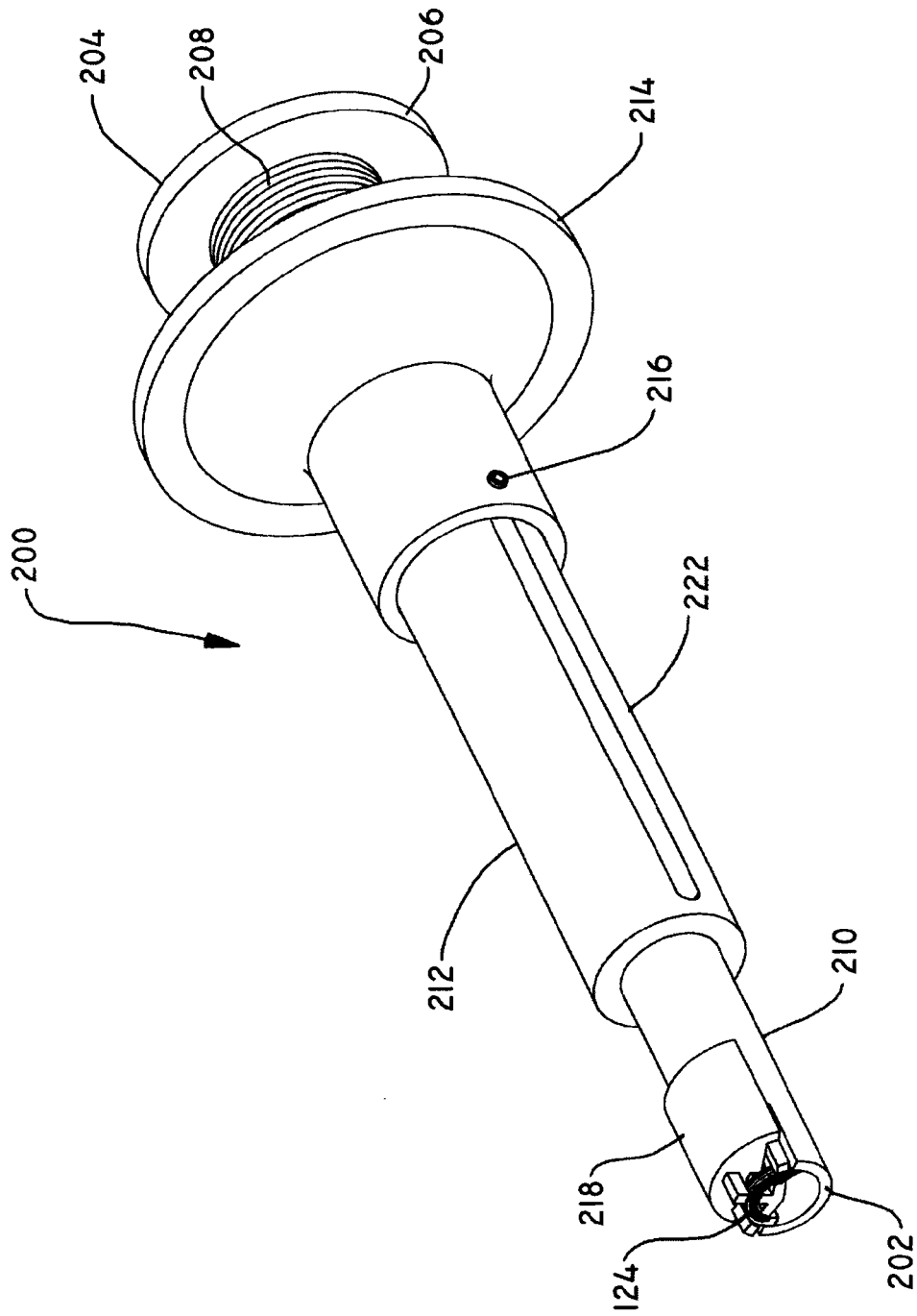
FIG. 9 is a perspective view of the tissue closure device of FIG. 7 in a post-fastener deployment configuration.

A representative embodiment of a tissue fastening device 200 of the present invention is illustrated in FIGS. 7, 8 and 9. Tissue fastening device 200 is generally defined by a proximal fastening end 202 and a distal biasing end 204, with the terms proximal and distal reflecting relative positioning with respect to tissue opening 100 during use of the tissue fastening device 200 to close tissue opening 100. Tissue fastening device 200 can comprise a biasing member 206, a spring member 208, an insertion member 210, fastener 124, a body member 212, a gripping member 214, a retention pin 216 and a tissue definition member 218. Tissue fastening device 200 can be fabricated of medically acceptable materials including metals such as, for example, stainless steel or medical grade polymers. As depicted in FIG. 8, tissue fastening device 200 is depicted in a pre-fastener deployment configuration 220 while in FIG. 9, tissue fastening device 200 is depicted in a post-fastener deployment configuration 222.

Figure 10:
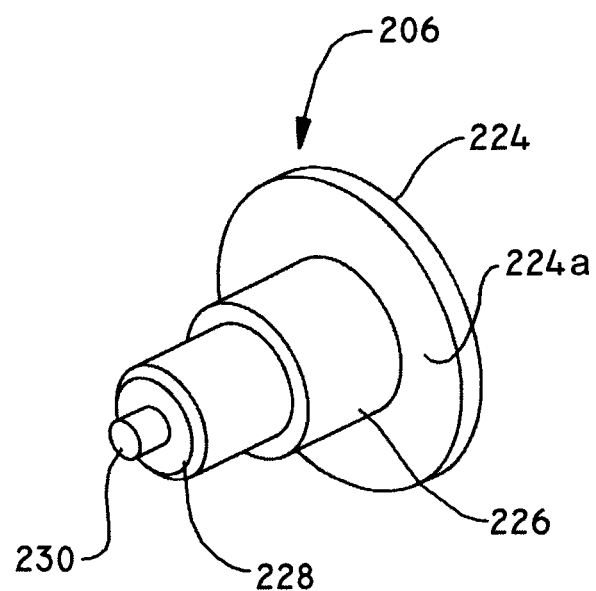
FIG. 10 is a perspective view of a biasing member used with the tissue closure device of FIG. 7.

Biasing member 206 is illustrated in more detail in FIG. 10. Biasing member 206 generally comprises a biasing surface 224 having an underside 224a, a biasing body 226 and a biasing interface 228. Biasing interface 228 can comprise a flat configuration or alternatively, a biasing projection 230.

Figure 11:
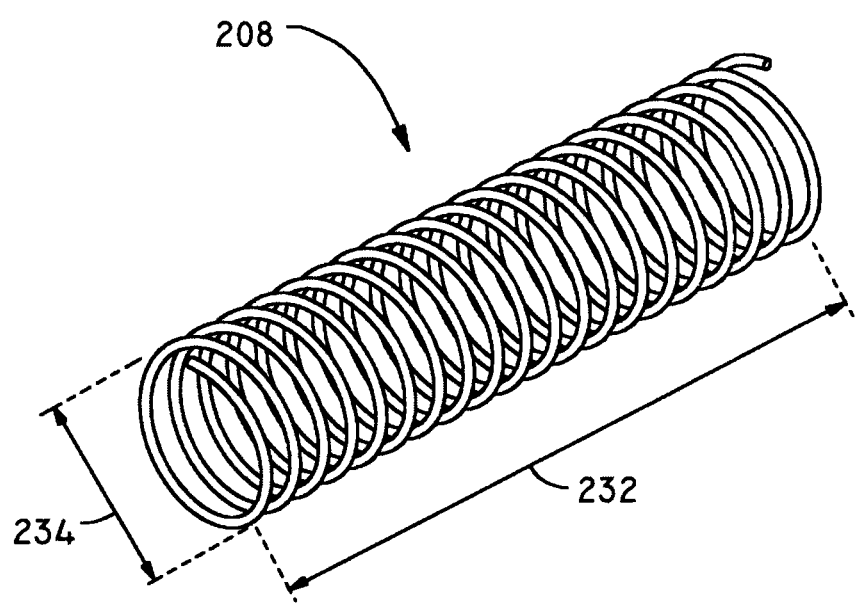
FIG. 11 is a perspective view of a spring member used with the tissue closure device of FIG. 7.

Spring member 208, as illustrated in FIG. 11, can comprise a metal or polymer-based spring having a suitable spring tension for use in a hand-operated instrument, for example an instrument capable of hand squeezing and initiation such as tissue fastening device 200. Spring member 208 defines a spring length 232 and a spring diameter 234. An appropriate spring diameter 234 can be selected to as to fully surround the biasing body 226 so as to directly interface with the underside 224a of biasing surface 224, as illustrated in FIG. 8.

Figure 12:
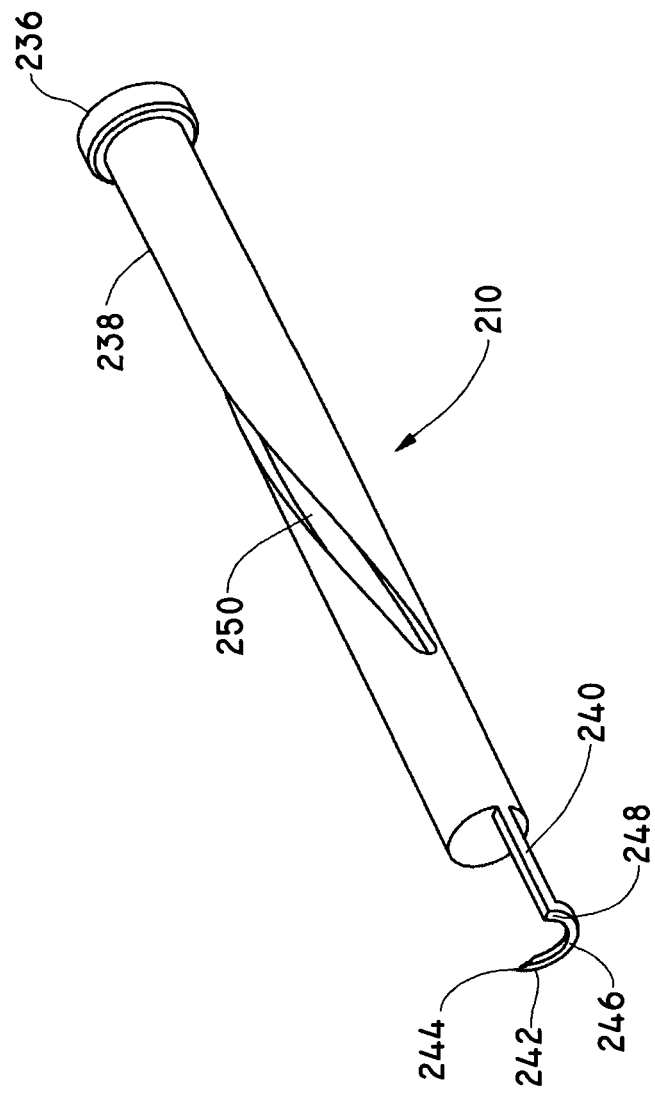
FIG. 12 is a perspective view of an insertion member used with the tissue closure device of FIG. 7.
Figure 13:
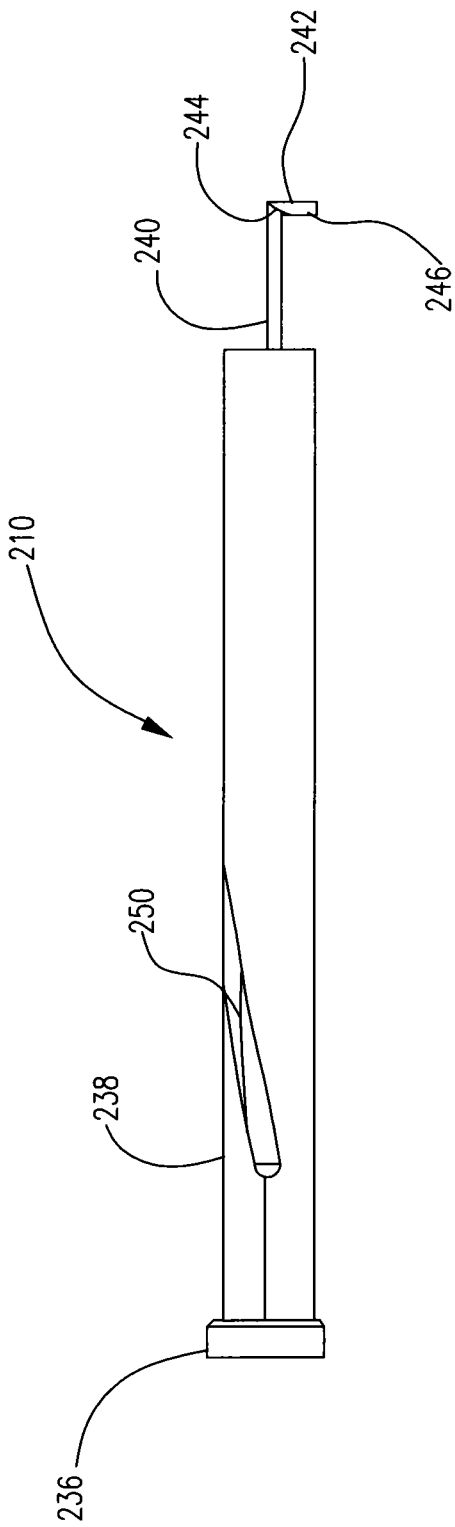
FIG. 13 is a side view of the insertion member of FIG. 12.
Figure 14:
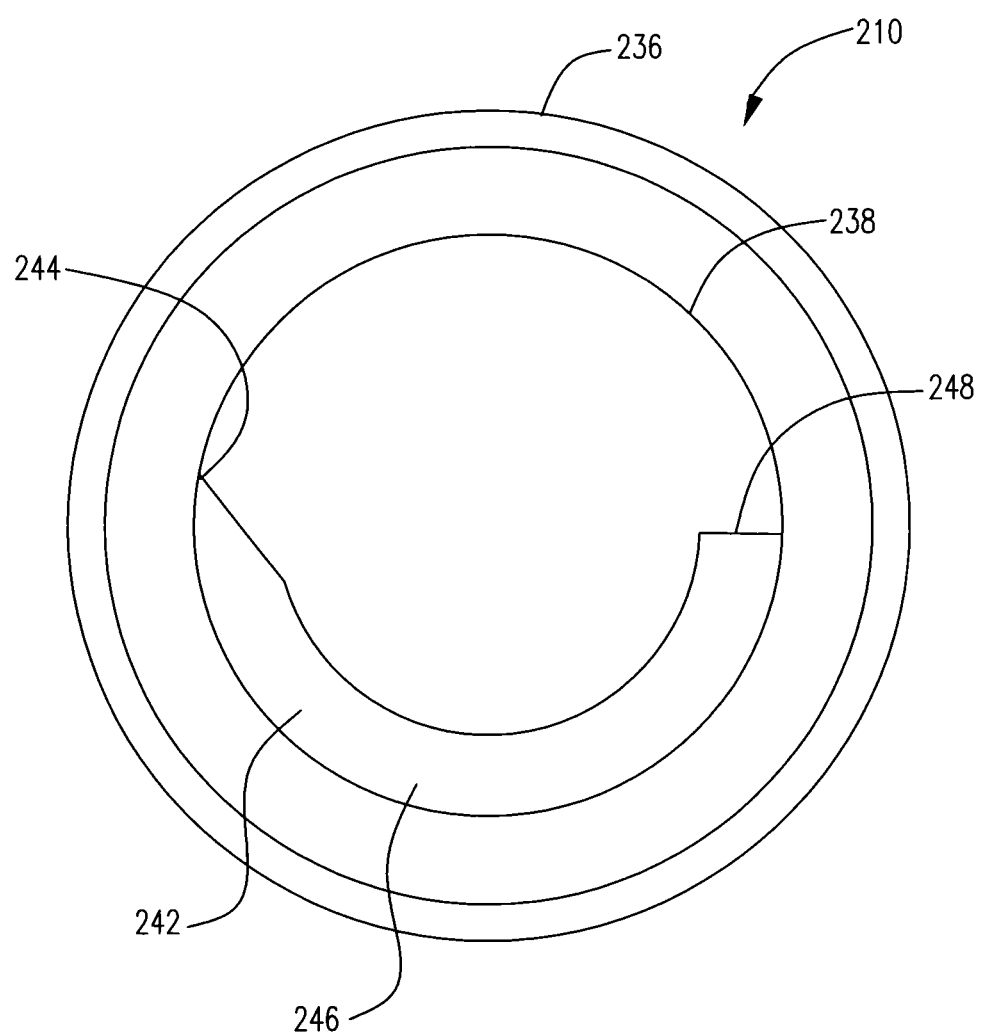
FIG. 14 is an end view of the insertion member of FIG. 12.

Insertion member 210 as illustrated in FIGS. 12, 13 and 14 can comprise an engagement surface 236, an insertion body 238, an extension member 240 and a penetrator 242. Insertion body 238 can in some representative embodiments comprise a generally cylindrical orientation and may comprise a solid body or alternatively, a hollow body, depending upon criteria such as material selection, component fabrication methods and the number of fastener 124 to be stored and/or deployed by the tissue fastening device 200. In some representative embodiments, extension member 240 and penetrator 242 can be integrally formed as a single component. Penetrator 242 generally comprises a generally falcate or sickle-shaped configuration defined by piercing end 244, a penetrator body 246 and a penetrator distal end 248 abutting and/or operably connected to the extension member 240. Insertion body 238 can comprise an external drive mechanism such as, for example, an external thread 250 or "rifling" so as to translate linear movement of insertion body 238 into rotatable movement of the penetrator 242. The external dive mechanism can in some embodiments comprise a groove and/or channel for receiving interfacing with an external member.

Figure 15:
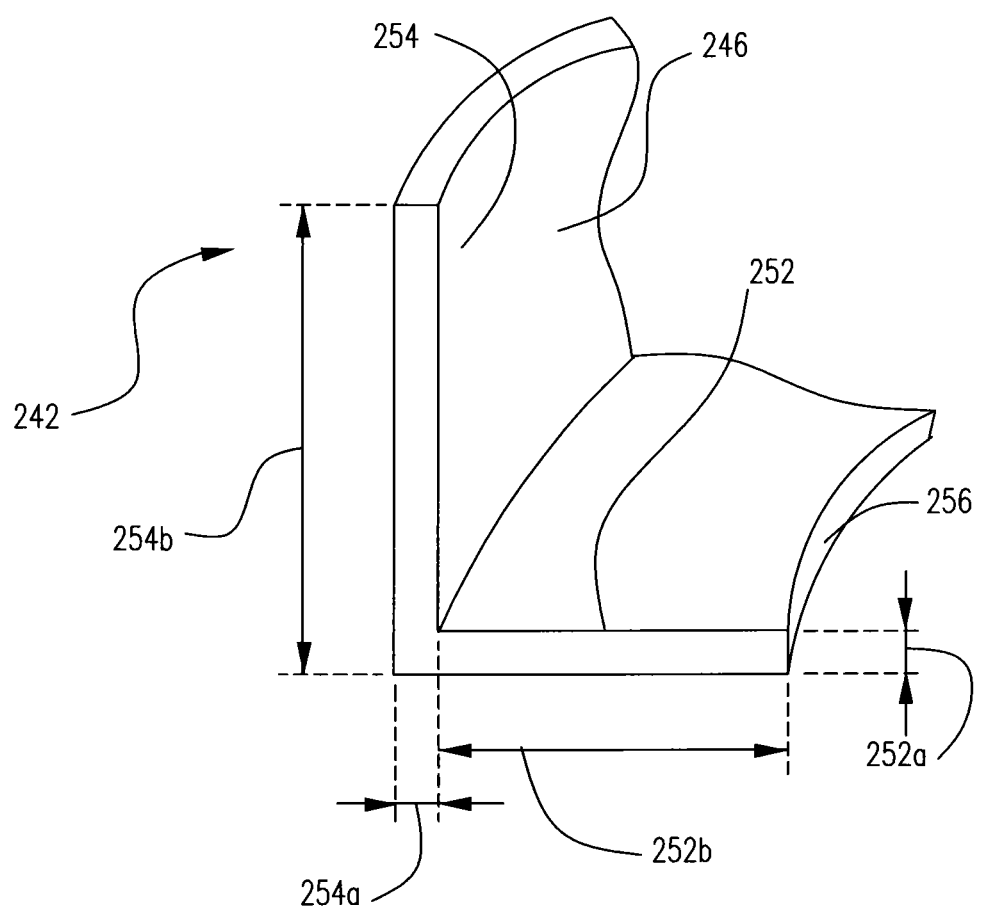
FIG. 15 is a section view of a penetrator portion of the insertion member of FIG. 12.
Figure 16:
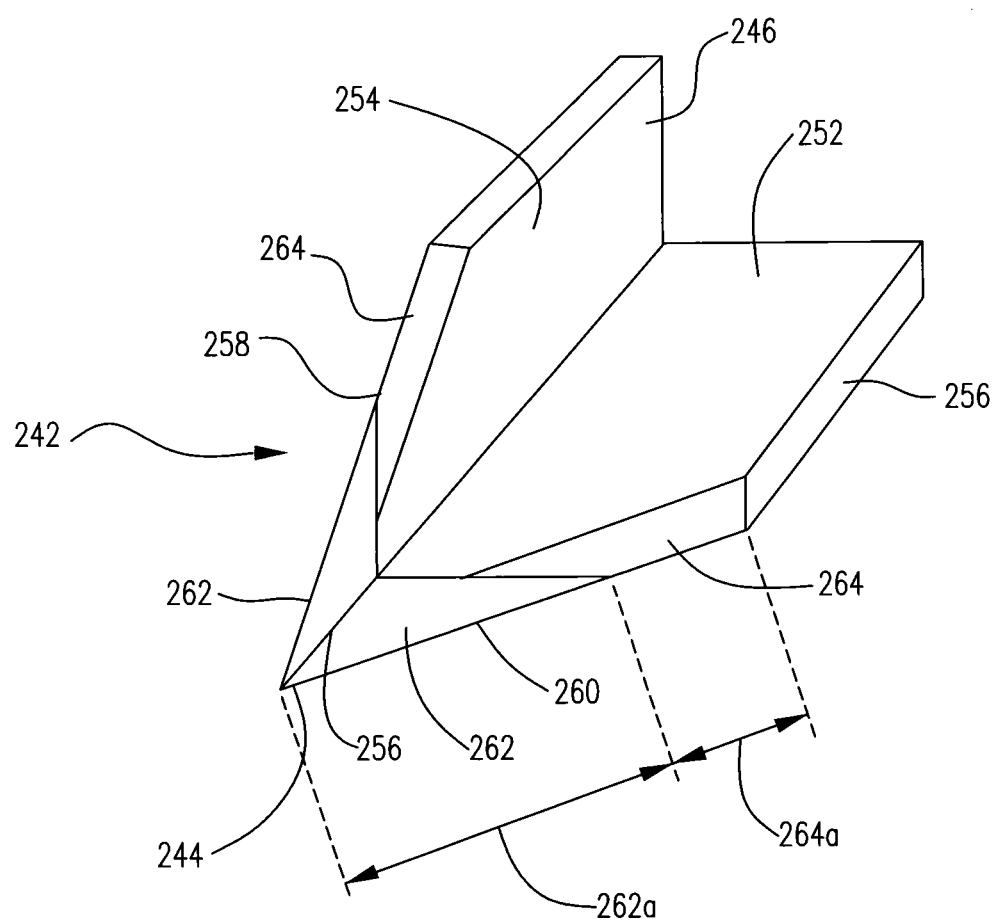
FIG. 16 is a detailed view of an embodiment of a penetrator piercing end.

Penetrator 242 is more clearly illustrated in detailed FIGS. 15 and 16. For example, penetrator body 246 is more clearly illustrated in section view in FIG. 15 as having a bottom penetrator surface 252 defined between a radial exterior wall surface 254 and a radial inner surface 256. Bottom penetrator surface 252 can comprise a bottom wall thickness 252a while radial exterior wall surface 254 can comprise a radial exterior wall thickness 254a. Bottom penetrator surface 252 comprises a bottom surface width 252b while radial exterior wall surface 254 comprises a radial exterior wall height 254b. Piercing end 244 as illustrated in FIG. 16 can comprise a dual-face penetrator 256 having a vertical cutting surface 258 and a horizontal cutting surface 260. Both the vertical cutting surface 258 and horizontal cutting surface 260 can comprise a first cutting facet 262 with a first facet length 262a and a second cutting facet 264 with a second facet length 264a. In some presently contemplated embodiments, first face length 262a can comprise anywhere from about ½ to about ⅔ of the individual lengths of vertical cutting surface 258 and horizontal cutting surface 260.

Figure 17:
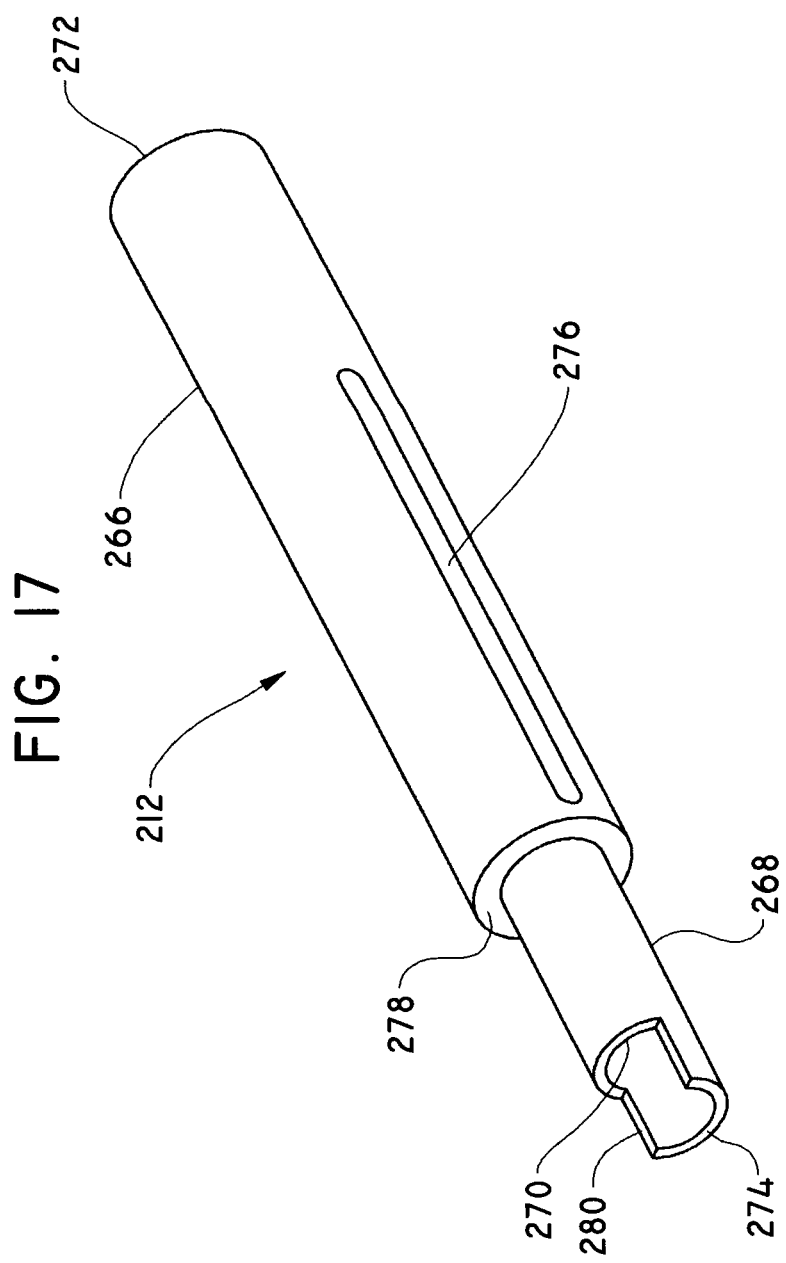
FIG. 17 is a perspective view of a body member used with the closure device of FIG. 7.
Figure 18:
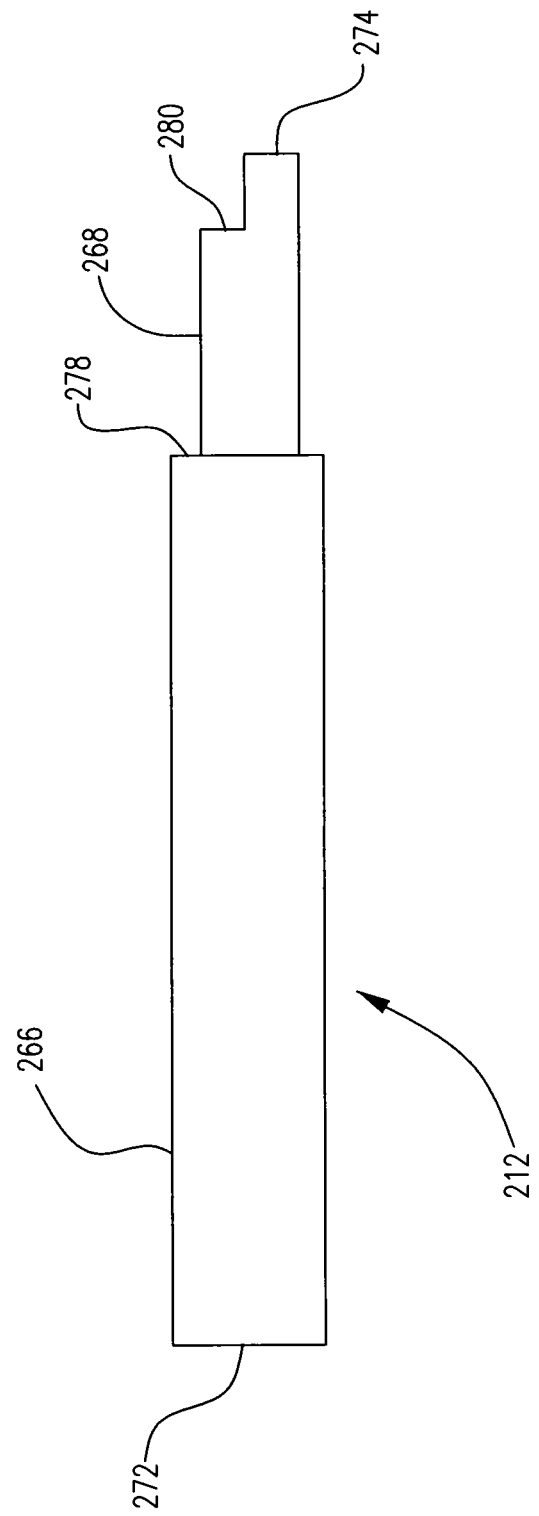
FIG. 18 is a side view of the body member of FIG. 17.
Figure 19:
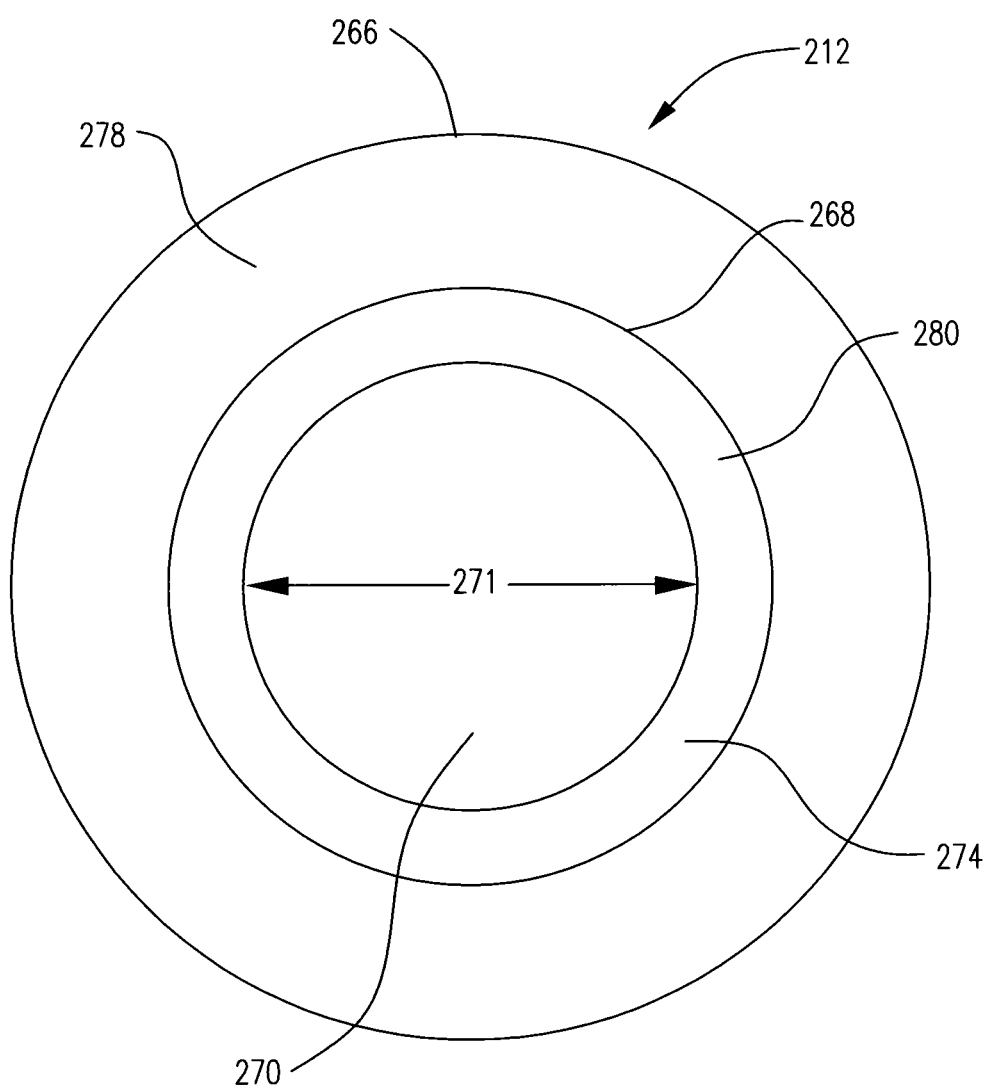
FIG. 19 is an end view of the body member of FIG. 17.

As illustrated in FIGS. 17, 18 and 19, body member 212 generally comprises a first body portion 266 and a second body portion 268. Body member 212 has a generally cylindrical configuration with a hollow interior 270 extending between a first body end 272 and a second body end 274. Hollow interior 270 defines an internal body diameter 271 sized so as to allow placement of insertion member 210 within hollow interior 270. First body portion 266 can comprise an exterior channel 276 extending from the exterior of first body portion 266 into the hollow interior 270. First body portion 266 and second body portion 268 are distinguished by a body flange 278. Second body portion 268 comprise an exposed portion 280 proximate the second body end 274, which generally corresponds to proximal fastening end 202.

Figure 20:
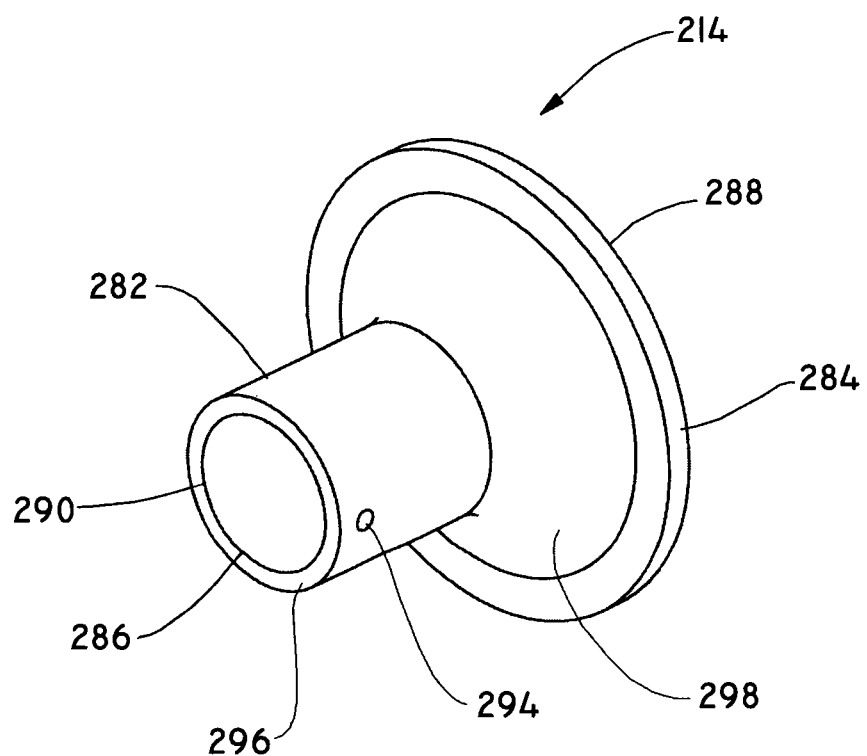
FIG. 20 is a perspective view of a gripping member used with the closure device of FIG. 7.
Figure 21:
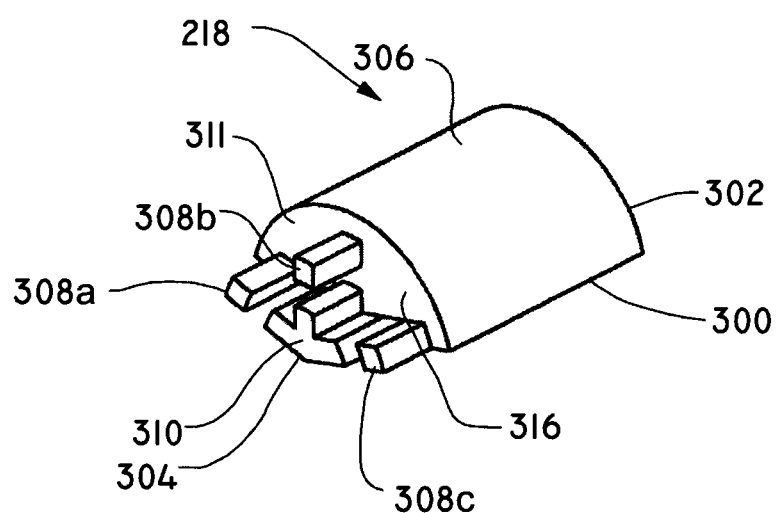
FIG. 21 is a perspective view of a tissue definition member used with the closure device of FIG. 7.
Figure 22:
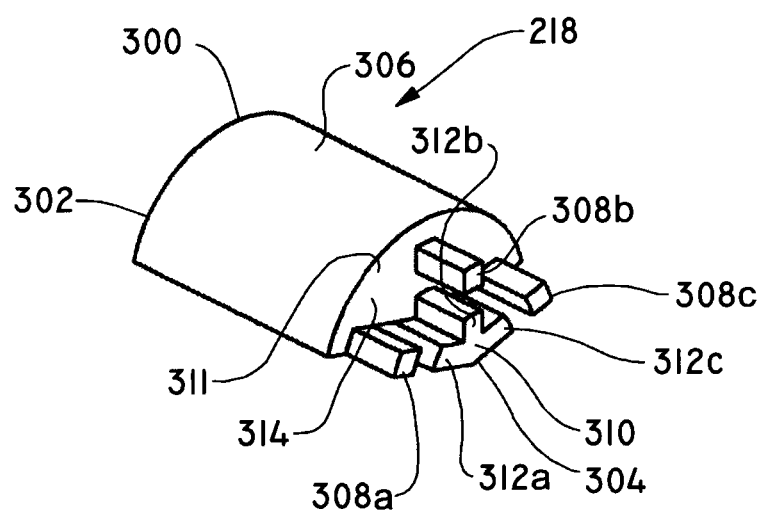
FIG. 22 is a perspective view of the tissue definition member of FIG. 21.
Figure 23:
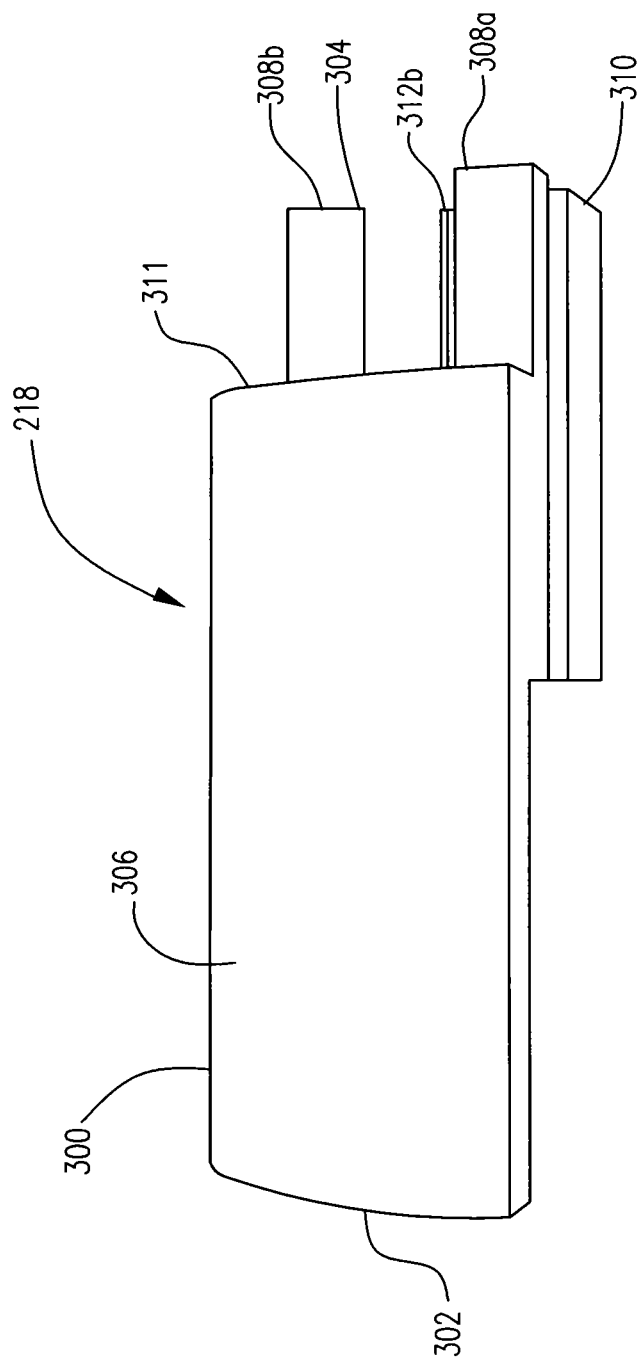
FIG. 23 is a side view of the tissue definition member of FIG. 21.
Figure 24:
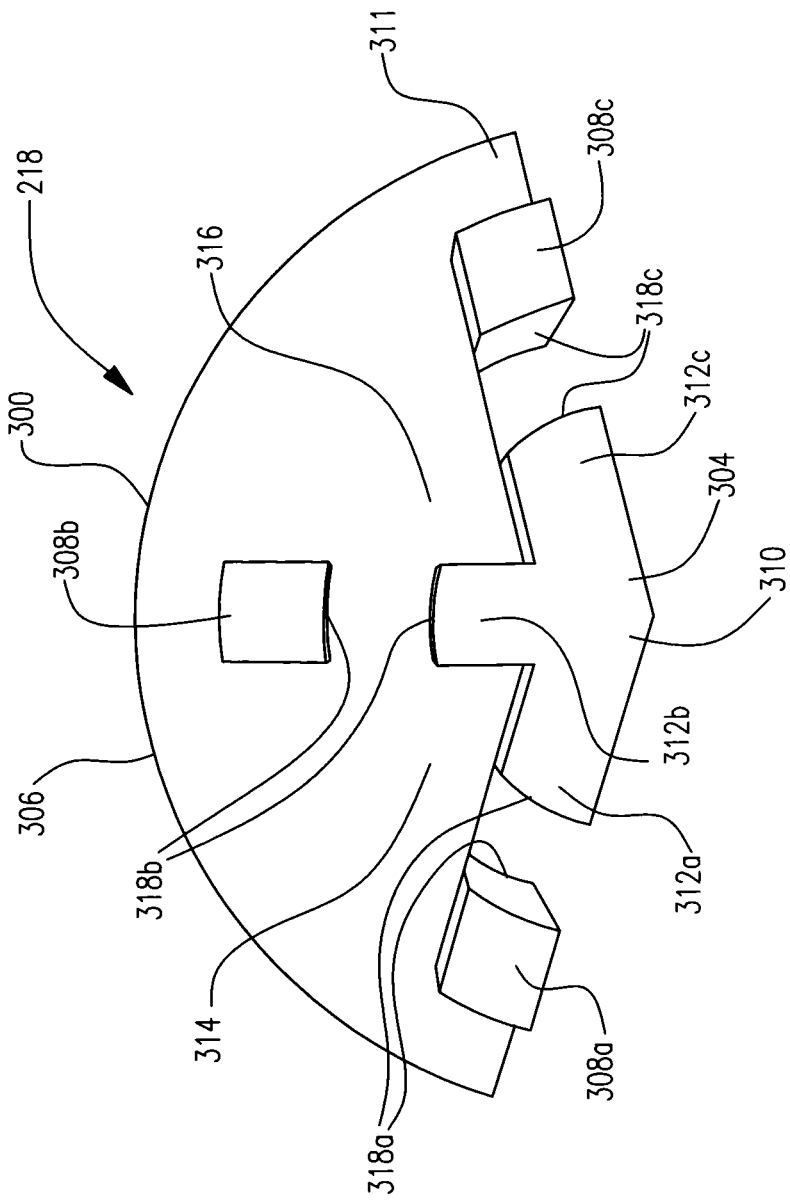
FIG. 24 is an end view of the tissue definition member of FIG. 21.

Gripping member 214, as illustrated in FIG. 20, generally comprises a hollow, cylindrical gripping body 282 and a flanged body portion 284. An interior portion 286 of the gripping member 214 extends between a first gripping end 288 and a second gripping end 290. Interior portion 286 comprises a gripping member interior diameter 292 generally sized such that body member 212, and more specifically first body portion 266 can be accommodated within interior portion 286. A gripping aperture 294 extends through a gripping body wall 296 of the cylindrical gripping body 282. Flanged body portion 284 defines a gripping surface 298.

Figure 25:
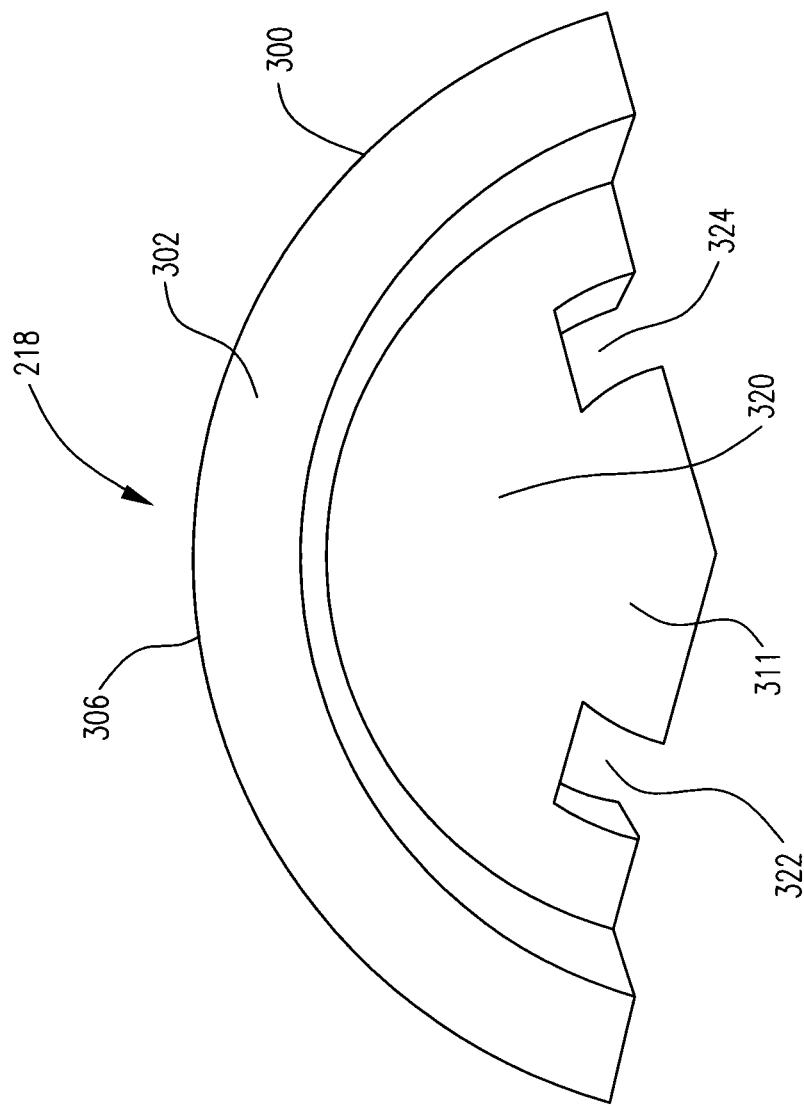
FIG. 25 is an end view of the tissue definition member of FIG. 21.
Figure 26:
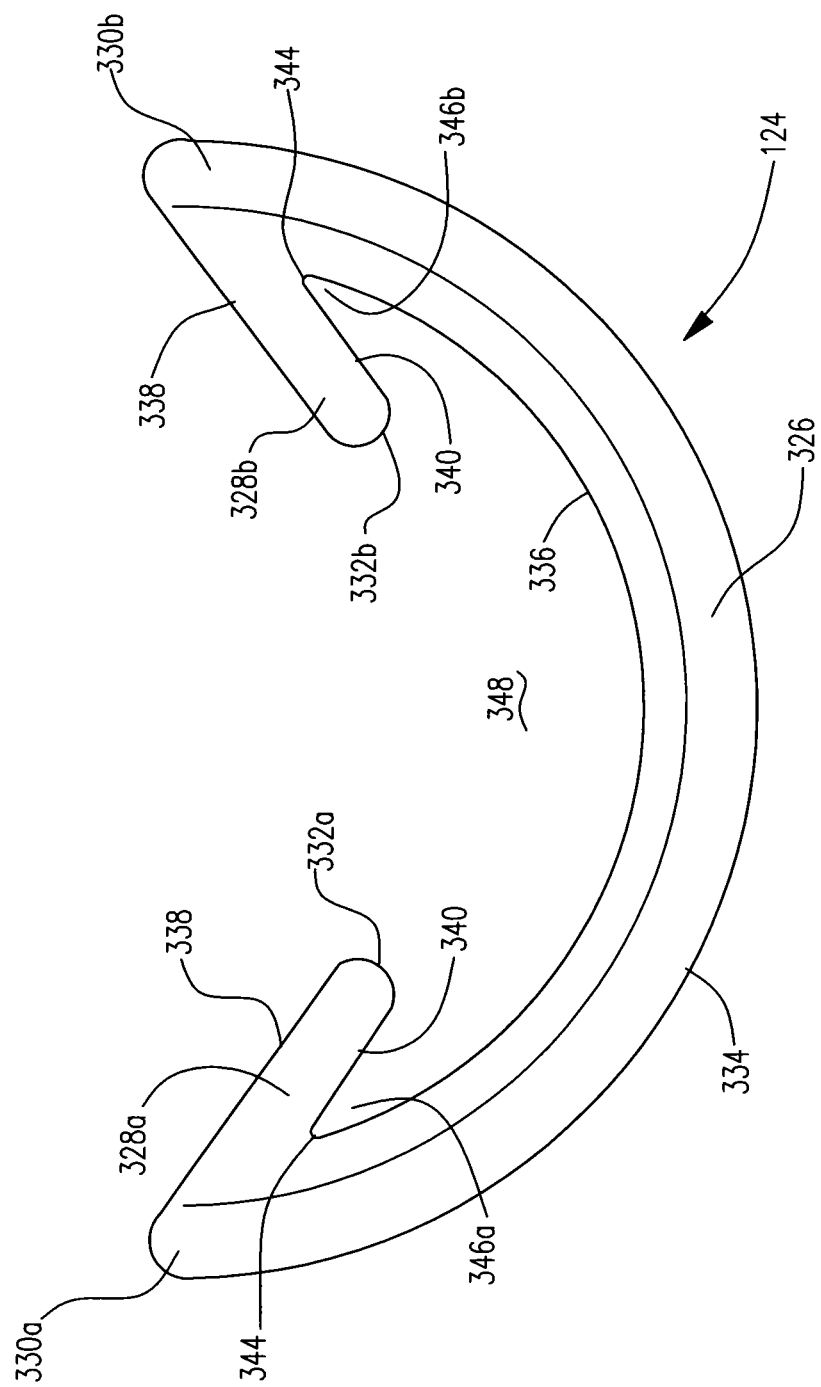
FIG. 26 is a top view of an embodiment of a fastener for use with the closure device of FIG. 7.

As illustrated in FIGS. 21, 22, 23, 24 and 25, tissue definition member 218 generally comprises a tissue definition body member 300 having a first definition member end 302 and a second definition member end 304, wherein the second definition member end 304 generally corresponds to proximal fastening end 202. Tissue definition body member 300 defines a generally arcuate perimeter body surface 306 sized and shaped to generally conform to exposed portion 280 of the body member 212. Second definition member end 304 comprises a first projecting block 308a, a second projecting block 308b, a third projecting block 308c and a central projecting member 310 all projecting outward from an end wall 311. Central projecting member 310 comprises a first projecting portion 312a, a second projecting portion 312b and a third projecting portion 312c. A first tissue capture area 314 is defined generally as the area bounded within first projecting block 308a, second projecting block 308b, first projecting portion 312a and second projecting portion 312b. A second tissue capture area 316 is defined generally as the area bound within second projecting block 308b, third projecting block 308c, second projecting portion 312b and third projecting portion 312c. A first insertion gap 318a is defined between first projecting block 308a and first projecting portion 312a. A second insertion gap 318b is defined between second projecting block 308b and second projecting portion 312b. A third insertion gap 318c is defined between third projecting block 308c and third projecting portion 312c. As illustrated in FIG. 25, tissue definition body member 300 further comprises an arcuate interior space 320 that generally matches and conforms to the size and shape of exposed portion 280. End wall 311 defines a first opening 322 corresponding to first insertion gap 318a and a second opening 324 corresponding to third insertion gap 318c.

A representative embodiment of fastener 124 is illustrated in FIGS. 26, 27, 28, 29a and 29b. Fastener 124 is comprised of a generally bioabsorbable polymer selected to maintain effective retention strength for a period of at least 5 to 21 days within the body, and optimally at least 14 days before eventually being fully absorbed within the human body. Most preferably, bioabsorbable polymer comprises a blended bioabsorbable copolymer comprised of 63% polylactide and 37% polygycolide, commonly referred to as PLGA. While the PLGA copolymer is used in one representative embodiment, other bioabsorbable polymers such as, for example, a lactide/glycolide copolymer, a poly(dl-lactide), a poly(l-lactide), a polyglycolide, a poly(dioxanone), a poly(glycolide-co-trimethylene carbonate), a poly(l-lactide-co-glycolide), a poly(dl-lactide-co-glycolide), a poly(l-lactide-co-dl-lactide), a poly(glycolide-co-trimethylene carbonate-co-dioxanone), collagen, and elastin, either individually, in blends or as copolymers, sharing similar traits including absorption traits, injection molding traits and polymer creep traits could be used as well. Similar to other polymers, the PLGA copolymer used in one representative embodiment exhibits viscoelastic properties in which the entangled molecules under stress tend to slide past one another, creating a viscoelastic creep.

Figure 27:
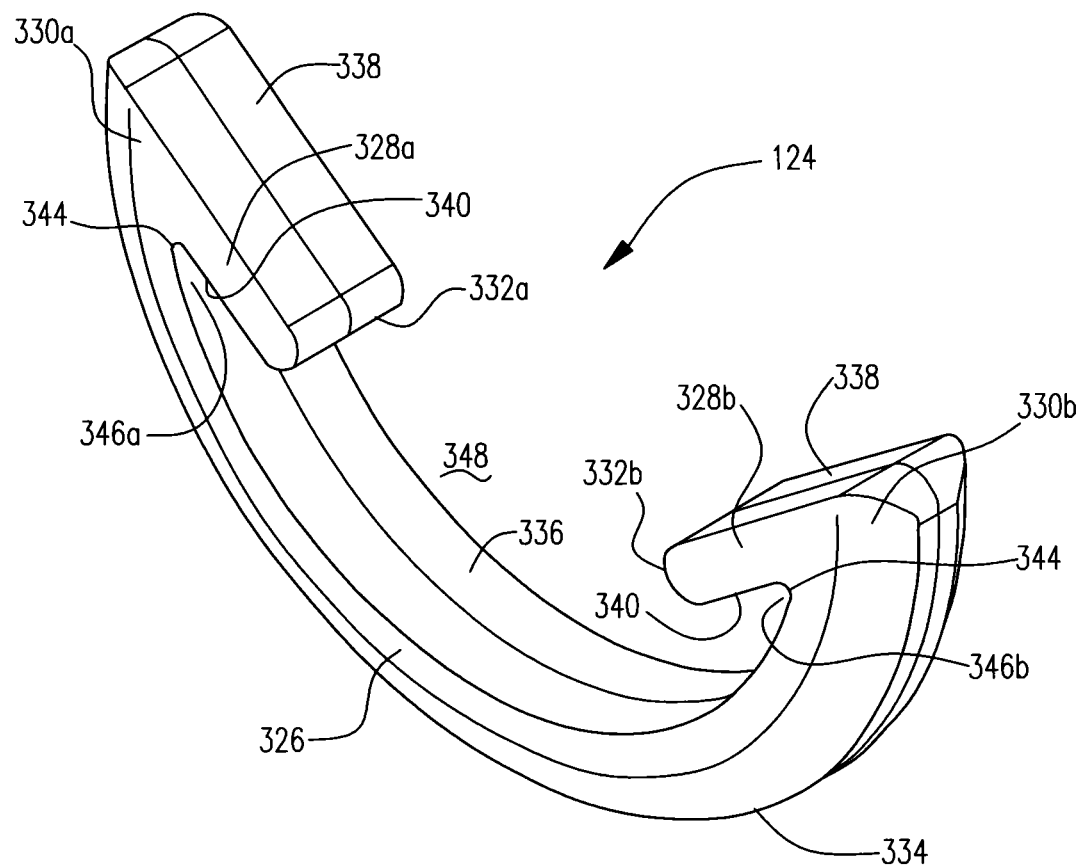
FIG. 27 is a perspective view of the fastener of FIG. 26.

Generally, fastener 124 comprises an arcuate body portion 326 operably connecting a pair of internally projecting cleats 328a, 328b at elbow portions 330a, 330b. Elbow portions 330a, 330b each preferably include a rounded cleat tip 332a, 332b. Arcuate body portion 326 can comprise a generally constant radius between the internally projecting cleats 328a, 328b defining an arc in range of about 125° to about 165°. Arcuate body portion 326 is generally defined by an arcuate exterior, perimeter surface 334 and an arcuate interior surface 336. The arcuate shape of interior surface 336 functions to even out and focus fastener loading forces and reduces potential rocking of fastener 124 during tissue retention. Fastener 124 can have a generally constant cross-sectional appearance between elbow portions 330a, 330b. In order to facilitate removal of fastener 124 from a molding process, fastener 124 can comprise a plurality of distinct segments and surfaces as illustrated in FIGS. 27 and 28.

Internally projecting cleats 328a, 328b are generally defined by an outwardly facing cleat surface 338, an inwardly facing cleat surface 340 and rounded cleat tips 332a, 332b. Each inwardly facing cleat surface 340 connects to the interior surface 336 at a cleat base 344 so as to define a pair of durable tissue retention zones 346a, 346b. In combination, interior surface 336 and the inwardly facing cleat surfaces 340 define an initial tissue capture zone 348.

Figure 28:
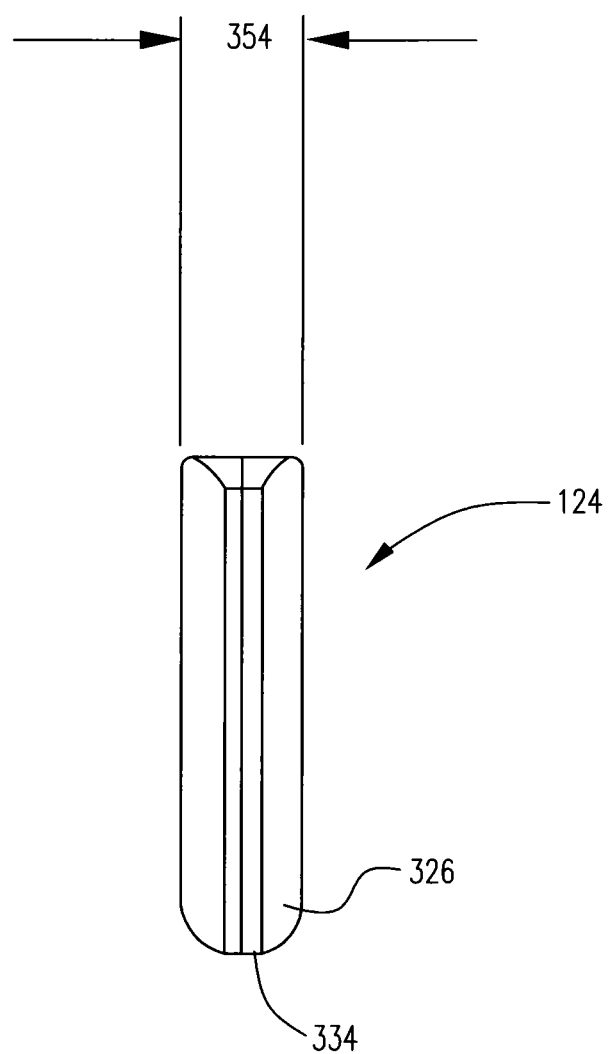
FIG. 28 is an end view of the fastener of FIG. 26.
Figure 29A:
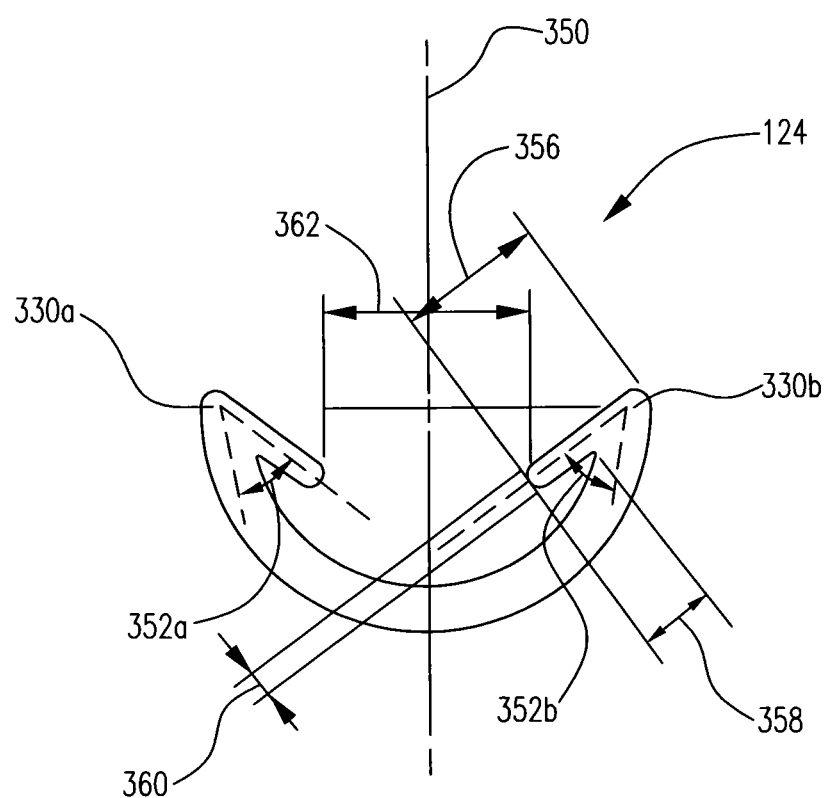
FIG. 29a is a top view of the fastener of FIG. 26.
Figure 29B:
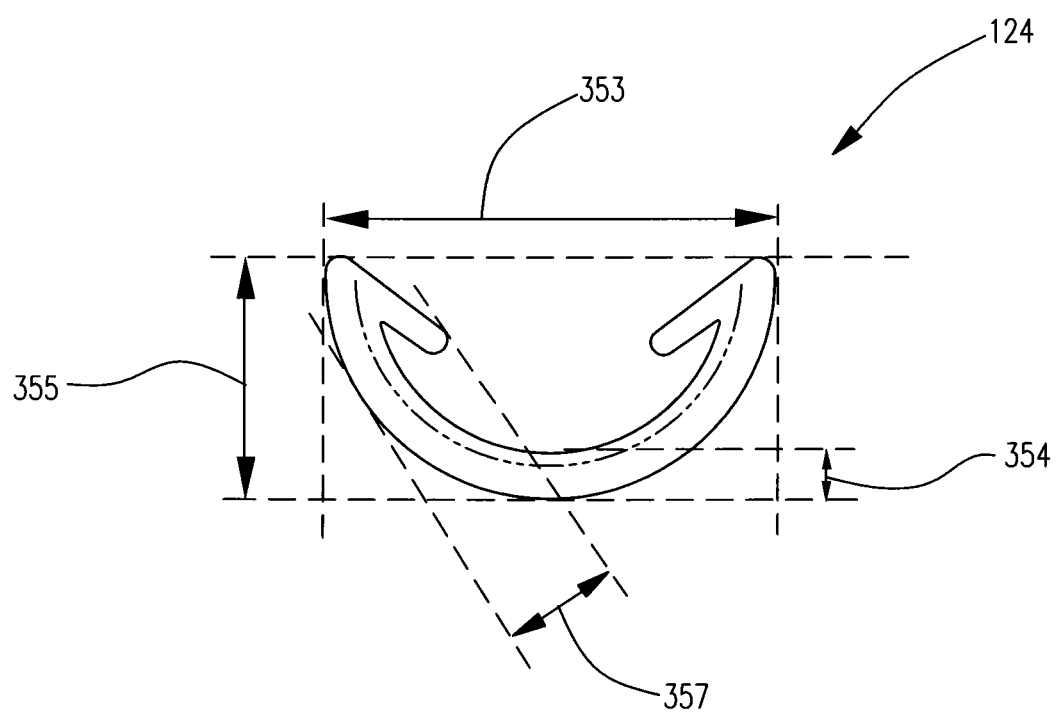
FIG. 29b is a top view of the fastener of FIG. 26.

The features of one embodiment of fastener 124 are further illustrated in FIGS. 28, 29a and 29b. These features can include an effective fastener center line 350 about which internally projecting cleans 328a, 328b can be symmetrically oriented. The intersection of arcuate body portion 326 with internally projecting cleats 328a, 328b creates internal elbow angles 352a, 352b relative to fastener 124. Elbow portions 330a, 330b are generally defined as the areas proximate the corresponding elbow angle 352a, 352b. Other features can include a fastener length 353, a body width 354, a fastener height 355, a outwardly facing cleat surface length 356, a cleat cross-sectional width 357 measured transversely to the arcuate body portion 326, an inwardly facing cleat surface length 358, a cleat width 360 and a cleat gap 362. Fastener length 353 can comprise a variety of length preferably not exceeding 22 mm in length. Similarly, fastener height 355 can comprise a variety of lengths with the preferable limitation that a ratio of fastener length 353 to fastener height 355 exceeds 2:1. Body width 354 can comprise a variety of widths preferably not exceeding 4 mm of cross-sectional width. Cleat cross-sectional width 357 can comprise a variety of widths with the preferable limitation that cleat cross-sectional width 357 exceeds the body width 354 by at least 50%. Cleat gap 362 preferably has a gap length from about 1 mm to about 12 mm.

After fastener 124 has been employed to retain and/or fasten tissue, stresses placed on the fastener 124 at elbow portions 330a, 330b can cause the arcuate body portion 326 to dynamically transition from the generally constant radius arc to a more linear disposition. After this dynamic transition, the ratio of fastener length 353 to fastener height 355 may increase by at least 10%.

Due to the expense of the bioabsorbable polymer resins used in fabricating fastener 124, it is preferable to avoid unnecessary waste during the molding process. In order to reduce waste, fastener 124 can be preferably formed using a micromolding injection molding process. Micromolding injection molding is typically used when the molding shot size is less than 1 gram. Using an appropriate micromolding injection system, for example a Battenfeld Microsystem M50, resin waste can be significantly reduced during production of a fastener 124 in accordance with the present invention. In addition, a micromolding injection system has other processing advantages such as allowing high injection speeds to promote dimensional stability, low residence times at elevated temperatures and integrated part handling capabilities.

Tissue fastening device 200 is generally assembled as illustrated in FIGS. 7, 8 and 9. Insertion member 210 is positioned with respect to body member 212 such that penetrator 242 can be slidably inserted from first body portion 266, through hollow interior 270 such that penetrator 242 resides proximate exposed portion 280. Gripping member 214 is placed over first body portion 266 of body member 212 and retention pin 216 is slidably inserted through gripping aperture 294 such that retention pin 216 retentively engages the exterior channel 276 on body member 212 as well as threaded channel 250 on the insertion member 210. When fully inserted, retention pin 216 operatively couples gripping member 214, insertion member 210 and body member 212.

Figure 30:
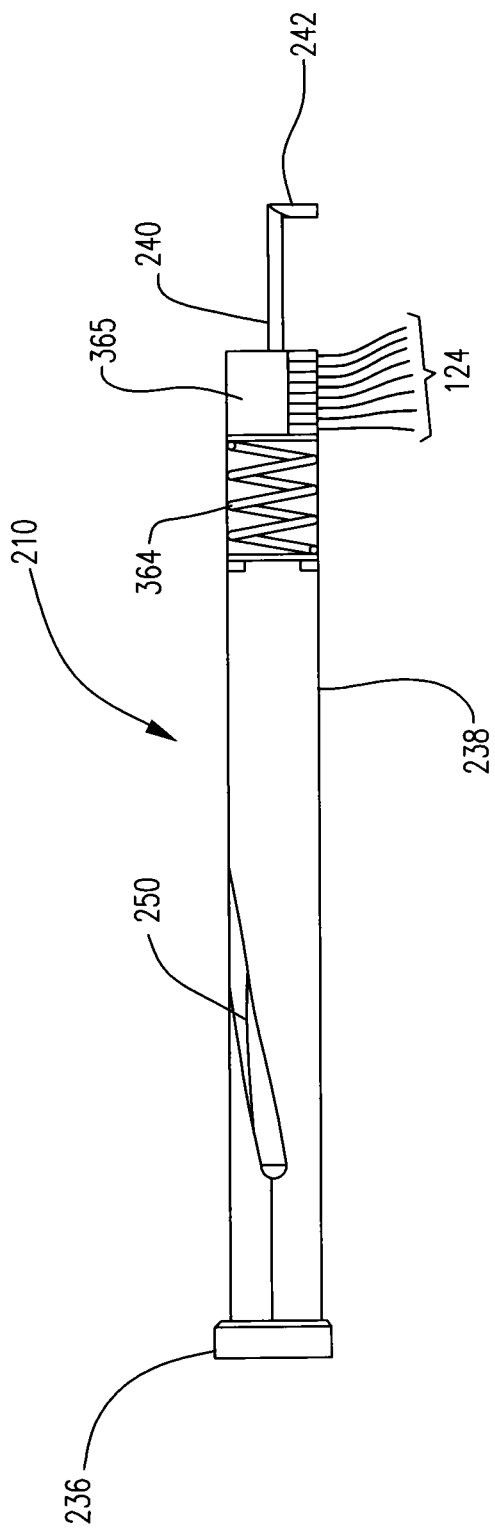
FIG. 30 is a partially hidden side view of an embodiment of an insertion member having a plurality of staged fasteners.
Figure 32:
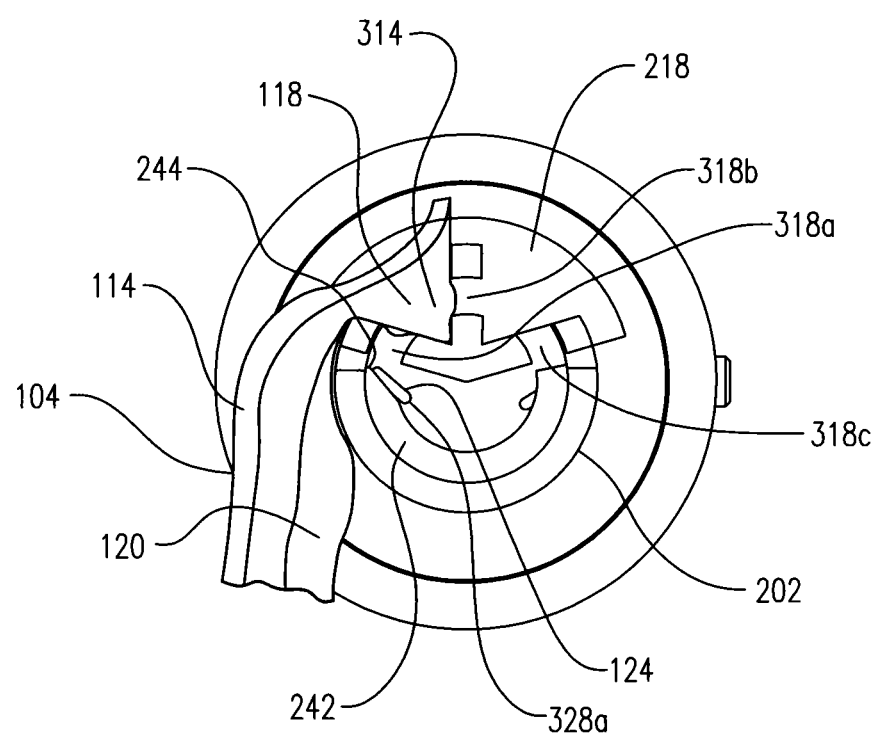
FIG. 32 is partially sectioned, end view of a tissue closure device with a first side of tissue positioned for capture and piercing.

Next, fastener 124 can be positioned and mounted with respect to penetrator 242 as illustrated in FIG. 32. As depicted in FIGS. 7, 8 and 9, tissue fastening device 200 can comprise a single fastener 124 for use in closing small tissue wounds such as, for example, skin biopsies and mole resections and various small-scale dermatology procedures. Alternatively, tissue fastening device can comprise a plurality of fasteners 124 arranged in a stacked configuration within an at least partially hollow version of insertion member 210 as shown in hidden view in FIG. 30. Insertion member 210 can comprise an advancing member 364 such as, for example, a spring, mounted within a hollow portion 365 to sequentially advance individual fasteners 124 into a mounting arrangement with respect to penetrator 242. By staging multiple fasteners 124 within insertion member 210, tissue fastening device 200 can be utilized to close larger wounds such as, for example, surgical incisions requiring more than one fastener 124 to accomplish successful wound closure.

After one or more fasteners 124 have been loaded, tissue definition member 218 can be operably mounted to exposed portion 280 such as, for example, with an adhesive or snap-fit arrangement. To complete assembly of tissue fastening device 200, spring member 208 is positioned over first body portion 266 of body member 212 such spring member 208 interfaces with the flanged body portion 284 of gripping member 214. Finally, biasing member 206 is operatively coupled to first body portion 266 of body member 212 such that biasing projection 230 abuts the engagement surface 236.

Figure 31:
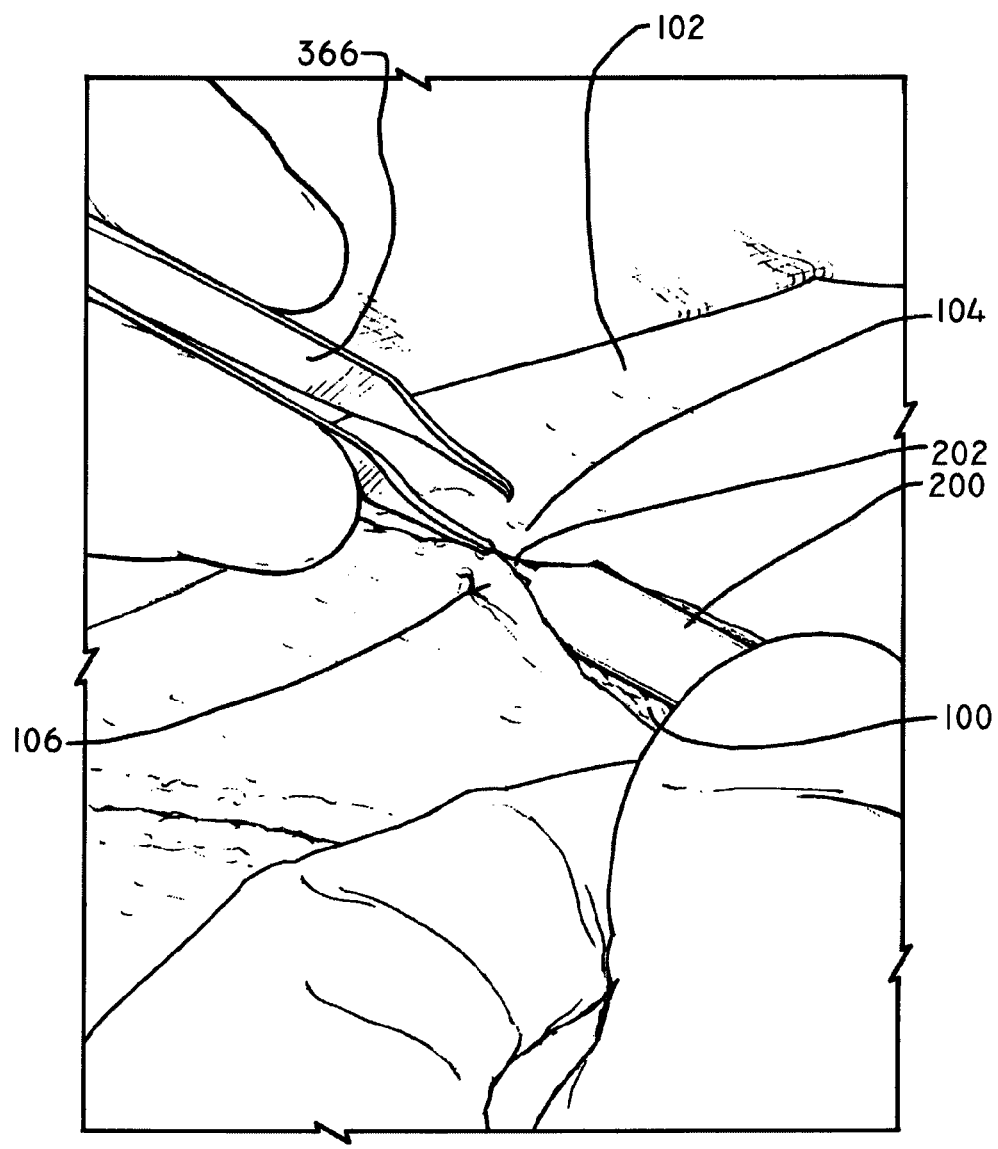
FIG. 31 is a top view of a skin wound being approximated with respect to an embodiment of a tissue closure device.

In use in one embodiment, tissue fastening device 200 can be utilized by dermatologists, physicians, clinicians and other medical personnel to accomplish a variety of skin closures including intentional, surgical incisions as well as accidental cuts, tears or piercings. Generally, a first step in effectuating wound closure with tissue fastening device 200 is to position proximal fastening end 202 proximate the wound as illustrated in FIG. 31. Tissue fastening device 200 should be in a pre-firing orientation, for example pre-fastener deployment configuration 220 as illustrated in FIG. 8. In some instances, proximal fastening end 202 can be positioned within the wound below the surface of skin 102 or alternatively, proximal fastening end 202 can be positioned above the surface of skin 102 wherein a user can manipulate first side 104 and second side 106 with a suitable grasping member 366 to lift skin 102 to the tissue fastening instrument 200 and achieve an everted disposition as illustrated in FIG. 3. Grasping member 366 can comprise a traditional forceps or a sequential tissue forceps as disclosed in United States Patent Publication No. 2006/0135988A1, which is herein incorporated by reference in its entirety.

Depending upon various wound characteristics such as, for example, body location, tissue type, wound tension, body type, patient age and similar variables, first side 104 and second side 106 can be simultaneously positioned with respect to proximal fastening end 202 or alternatively, a first side 104 be positioned and captured with fastener 124, as describe below, followed by capture and fastening of a second side 106. Sequential capture, as opposed to simultaneous fastening, of first side 104 and second side 106 may be especially applicable to large wounds or high tension wounds wherein simultaneously capturing, positioning and retaining tissue is made increasingly difficult.

First side 104 is gripped and stretched by grasping member 366 such that first side 104 resembles the stretched configuration illustrated in FIG. 3. Once stretched, first side 104 is positioned with respect to tissue definition member 218 such that dermal layer 118 substantially occupies and fills first tissue capture area 314 as illustrated in FIG. 32. Because of the stretched configuration of first side 104, epidermal layer 114 and subcutaneous tissue layer 120 are kept substantially out of and preferably entirely absent from first tissue capture are 314. If any of the first projecting block 308a, second projecting block 308b and/or central projecting member 310 include retaining projections 325, the retaining projections 325 further assist to capture and retain the dermal layer 118 within the first tissue capture area 314.

Figure 33:
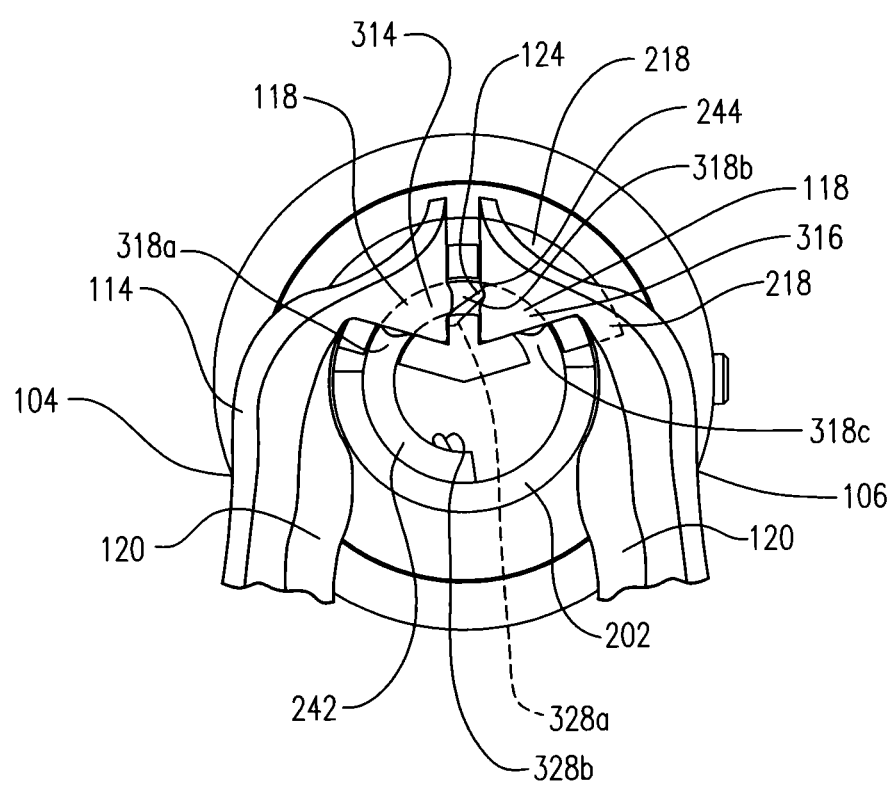
FIG. 33 is a partially sectioned, end view of a tissue closure device with a first side of tissue being pierced and also having a second side of tissue positioned for subsequent capture and piercing.
Figure 33A:
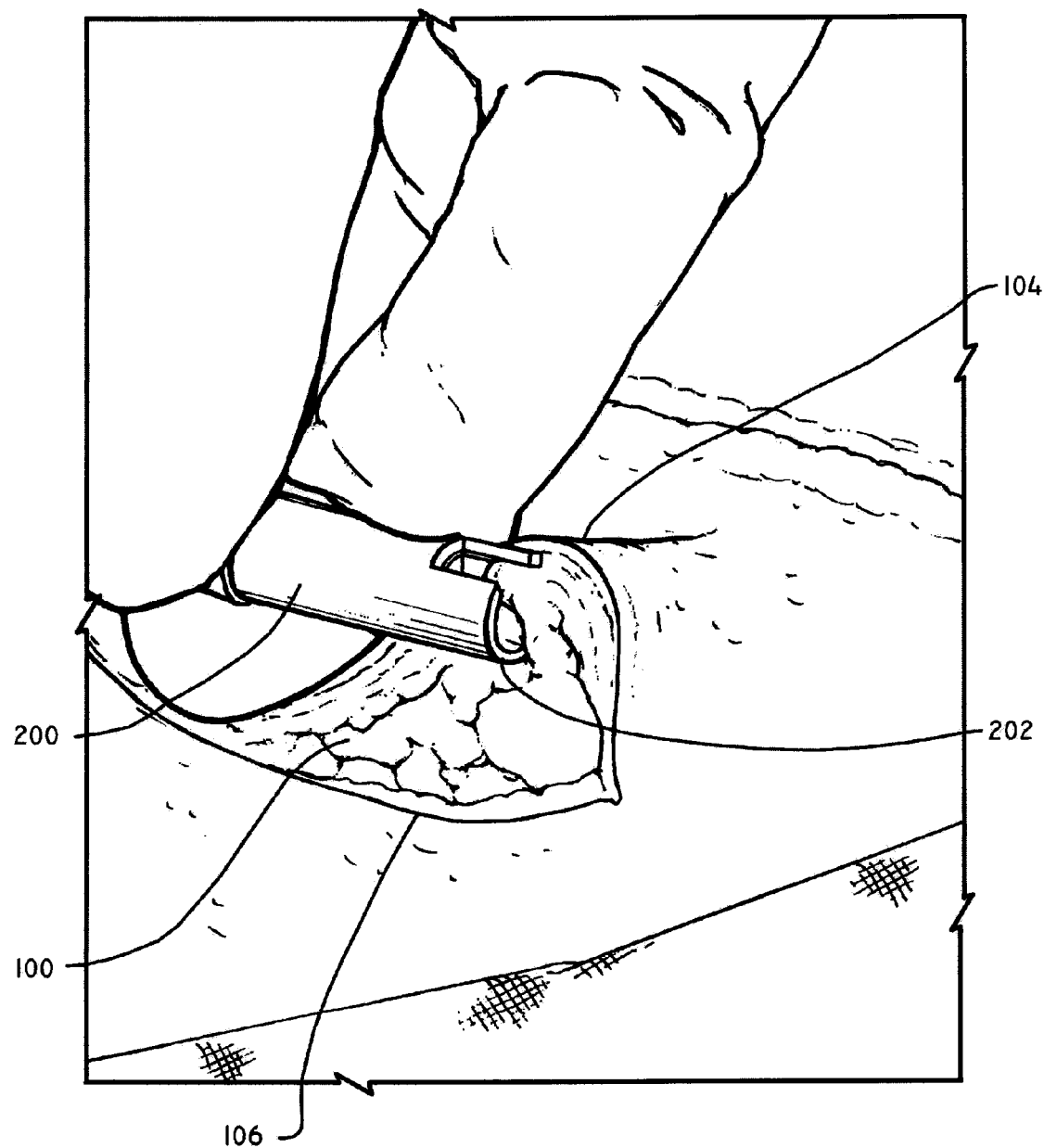
FIG. 33a is a top view of skin wound with a first tissue side being captured and pierced.

Once the dermal layer 118 of first side 104 is positioned within first tissue capture area 314, a medical professional such as, for example, a doctor or nurse squeezes together biasing member 206 and gripping member 214. This squeezing action causes retention pin 216 to begin traversing the threaded channel 250, thus imparting a rotational spin to insertion member 210. As insertion member 210 spins, rotational motion is imparted to penetrator 242 such that piercing end 244 is rotatably directed through first insertion gap 318a. Continued squeezing together of the biasing member 206 and gripping member 214 directs piercing end 244 through the first tissue capture are 314, which simultaneously results in piercing end 244 piercing and passing through the dermal layer 118 of first side 104 as illustrated in FIG. 33. As penetrator 242 rotatably traverses the first tissue capture area 314, fastener 124 is carried through the pierced opening such that internally projecting cleat 328a passes though dermal layer 118 of first side 104. As internally projecting cleat 328a has a cross-section substantially greater than penetrator 242, the elastic tissue of dermal layer 118 is required to stretch around and over inwardly projecting cleat 328a. As piercing end 244 approaches second insertion gap 318b, first side 104 can be released by grasping member 366 as first side 104 is now fully retained by penetrator 242 and fastener 124 as illustrated in FIG. 33a.

Next, second side 106 is gripped and stretched by grasping member 366 such that second side 106 resembles the stretched configuration illustrated in FIG. 3. Once stretched, second side 106 is positioned with respect to tissue definition member 218 such that dermal layer 118 substantially occupies and fills second tissue capture area 316 as illustrated in FIG. 33. For similar reasons as previously discussed with respect to first side 104, epidermal layer 114 and subcutaneous tissue layer 120 are kept substantially out of and preferably entirely absent from second tissue capture are 316. If any of the second projecting block 308b, third projecting block 308c and/or central projecting member 310 include retaining projections 325, the retaining projections 325 further assist to capture and retain the dermal layer 118 within the second tissue capture area 316.

Figure 34:
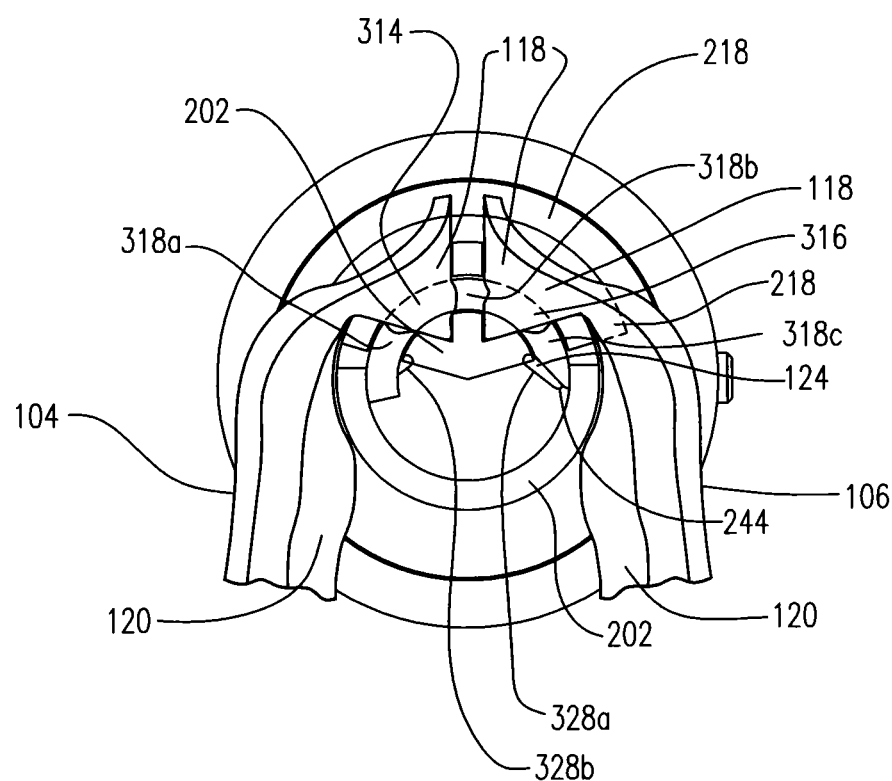
FIG. 34 is a partially sectioned, end view of a tissue closure device with both first and second sides of tissue being pierced and having a fastener positioned therein.

After positioning second side 106, the medical professional continues with the squeezing together of biasing member 206 and gripping member 214. As discussed previously, this squeezing action causes insertion member 210 to spin such that penetrator 242 is rotatably advanced into the second tissue capture area 316. As discussed previously with respect to first side 104, piercing end 244 pierces and passes through the dermal layer 118 of second side 106. As penetrator 242 rotatably traverses the second tissue capture area 316, fastener 124 is carried through the pierced opening such that internally projecting cleat 328a passes though dermal layer 118 of first side 104 as illustrated in FIG. 34. At the same time, projecting cleat 328b rotatably follows into the first tissue capture area 314 wherein the dermal layer 118 is generally piled into and retained within the durable tissue retention zone 346b as projecting cleat 328b has a cross-section substantially larger than the opening pierced by penetrator 242. As biasing member 206 and gripping member 214 are squeezed to their closest orientation, piercing end 244 exits dermal layer 118 of second side 106 through the third insertion gap 318c. As inwardly projecting cleat 328a passes through the third insertion gap 318c, the elastic tissue of dermal layer 118 is required to stretch around and over inwardly projecting cleat 328a whereby second side 106 is elastically captured within durable tissue retention zone 346a.

Figure 35:
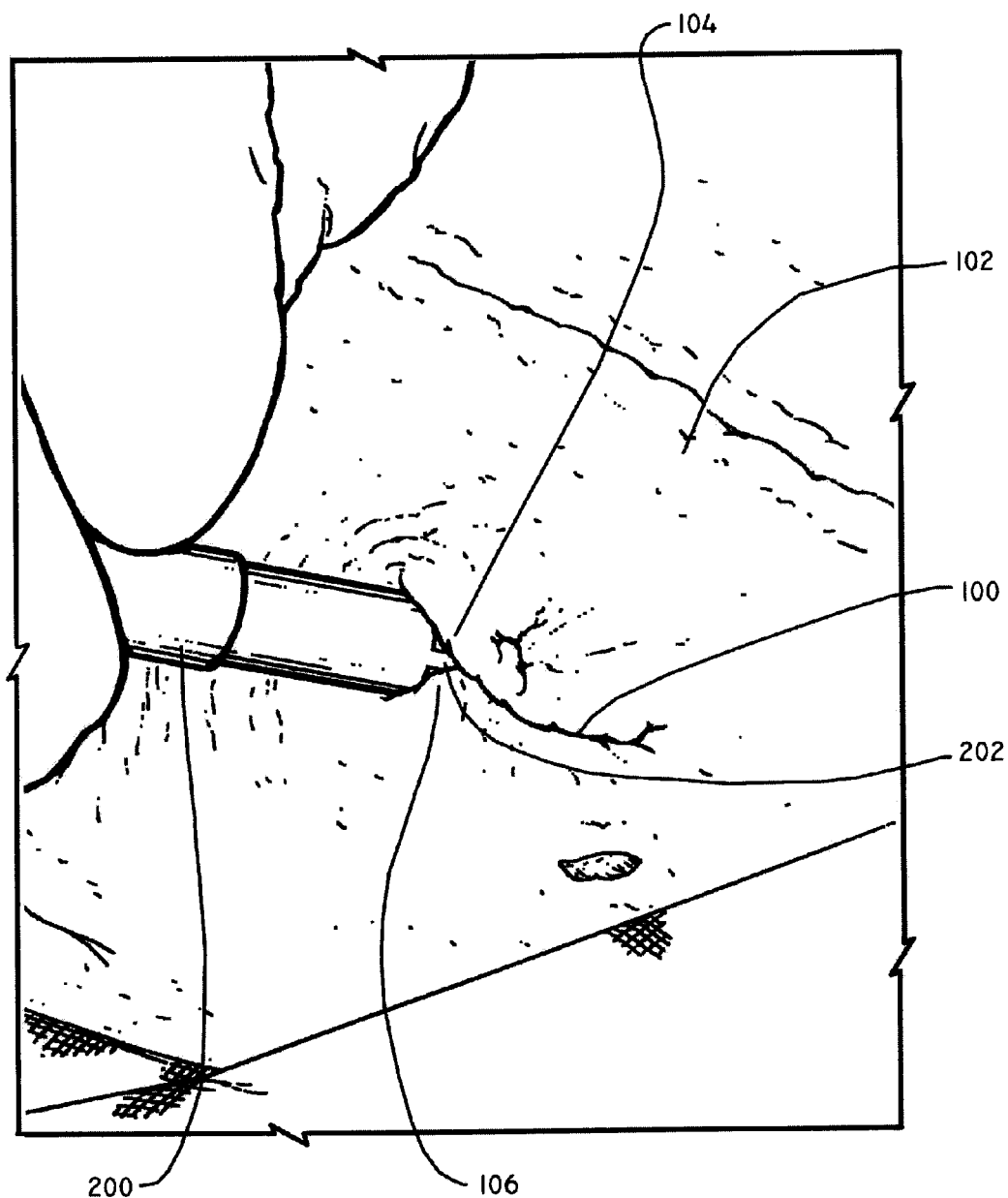
FIG. 35 is a top view of a partially closed skin wound wherein a portion of the skin wound has been closed with fasteners deployed from a tissue closure device and with the tissue closure device deploying an additional fastener to further effectuate closure of the skin wound.

Generally, biasing member 206 and gripping member 214 reach an orientation, for example, in the post-fastener deployment configuration 222 shown in FIG. 9, where further squeezing together is impossible and/or prevented. This orientation generally corresponds to the point in time where piercing end 244 and inwardly projecting cleat 328a have passed through the third insertion gap 318c. During the squeezing of biasing member 206 and gripping member 214, spring member 208 has been compressed. At this point, the medical professional releases the gripping member 214 causing spring member 208 to rebound and direct gripping member 214 and biasing member 206 apart. The rebound of spring member 208 causes retention pin 216 to begin reversibly traversing the threaded channel 250, thus imparting a reverse rotational spin to insertion member 210. As insertion member 210 spins in an opposite direction, this opposite rotational motion is imparted to penetrator 242 such that piercing end 244 is rotatably sequentially withdrawn though third insertion gap 318c, second tissue capture area 316, second insertion gap 318b, first tissue capture area 314 and first insertion gap 318a. While penetrator 242 is rotatably withdrawn, fastener 124 remains positioned within the dermal layers 118 of first side 104 and second side 106 as the increased cross-sectional areas of projecting cleats 328a, 328b prevent fastener 124 from being rotatably withdrawn. As such, first side 104 and second side 106 remain in a retained, proximate orientation as illustrated in FIG. 35 due to the tissue captured within the durable tissue retention zones 346a, 346. The proximal fastening end 202 is then removed from the opening 100. For wounds requiring more than one fastener 124 to effectuate closure, tissue fastening device 200 can be advanced to the next preferred fastening location wherein the process can be repeated for insertion of additional fasteners 124.

Figure 36:
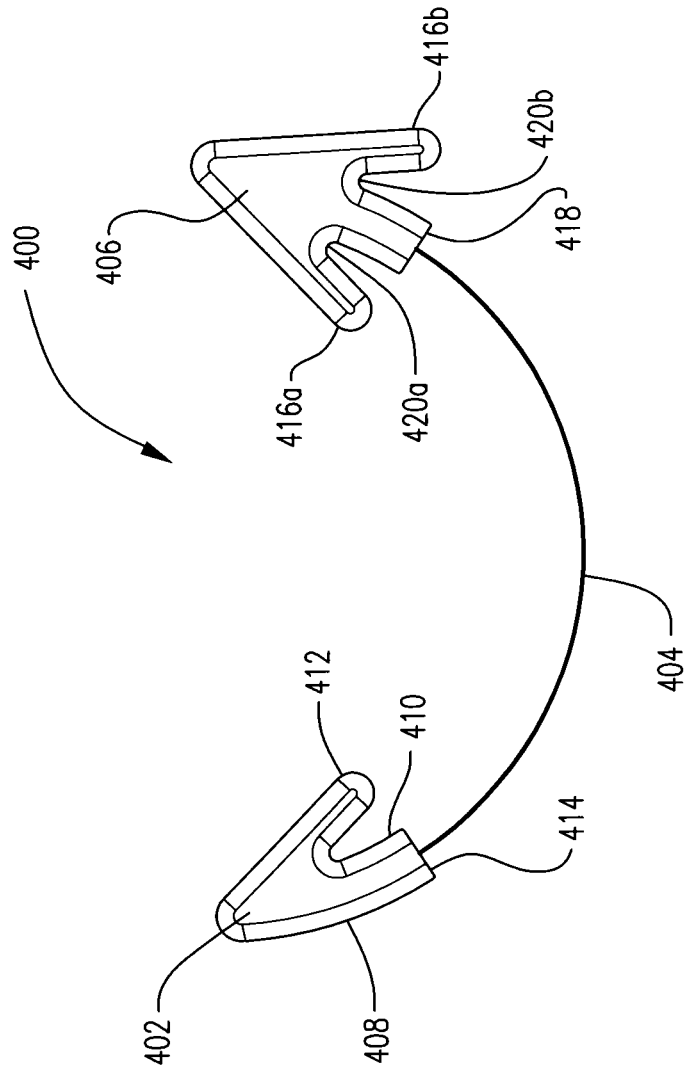
FIG. 36 is a top view of an embodiment of a fastener for use with a tissue closure device.

In addition to previously described fastener 124, tissue fastening device 200 can utilize alternative fastener designs such as, for example, a fastener 400 as illustrated in FIG. 36. Fastener 400 can comprise a leading body portion 402, a suture body portion 404 and a trailing body portion 406. Leading body portion 402 can comprise an outer wall 408, an inner wall 410, an inwardly projecting cleat 412 and a leading attachment wall 414. Suture body portion 404 generally comprises a non rigid suture material such as, for example, materials commonly used in suturing and/or stitching wounds closed. Trailing body portion 406 can comprise a pair of anchoring cleats 416a, 416b and a trailing attachment wall 418. Fastener 400 can be fabricated of similar bioabsorbable materials as previously described with respect to fastener 124. When fastener 400 is utilized for wound closure using the method previously described with respect to tissue fastening device 200, leading body portion 402 functions substantially similar to internally projecting cleat 328a while the anchoring cleats 416a, 416b essentially perform a dual anchoring function by simultaneously retaining tissue within a pair of anchoring tissue retention zones 420a, 420b.

As will be recognized by one of skill in the art, suitable fasteners for use with the presently disclosed methods and apparatus may comprise a variety of configurations, especially with respect to trailing portions of the fastener. Generally speaking, suitable fasteners will comprise a trailing anchoring mechanism for effectuating tissue capture and retention, such as internally projecting cleat 328b and anchoring cleats 416a, 416b. In addition, suitable fasteners will include a suitable connecting element such as arcuate body portion 326 and suture body portion 404, for effectively connecting leading portions of the fastener such as internally projecting cleat 328a and leading body portion 402 during insertion and over the period of time required for healing of skin opening 100.

Figure 37:
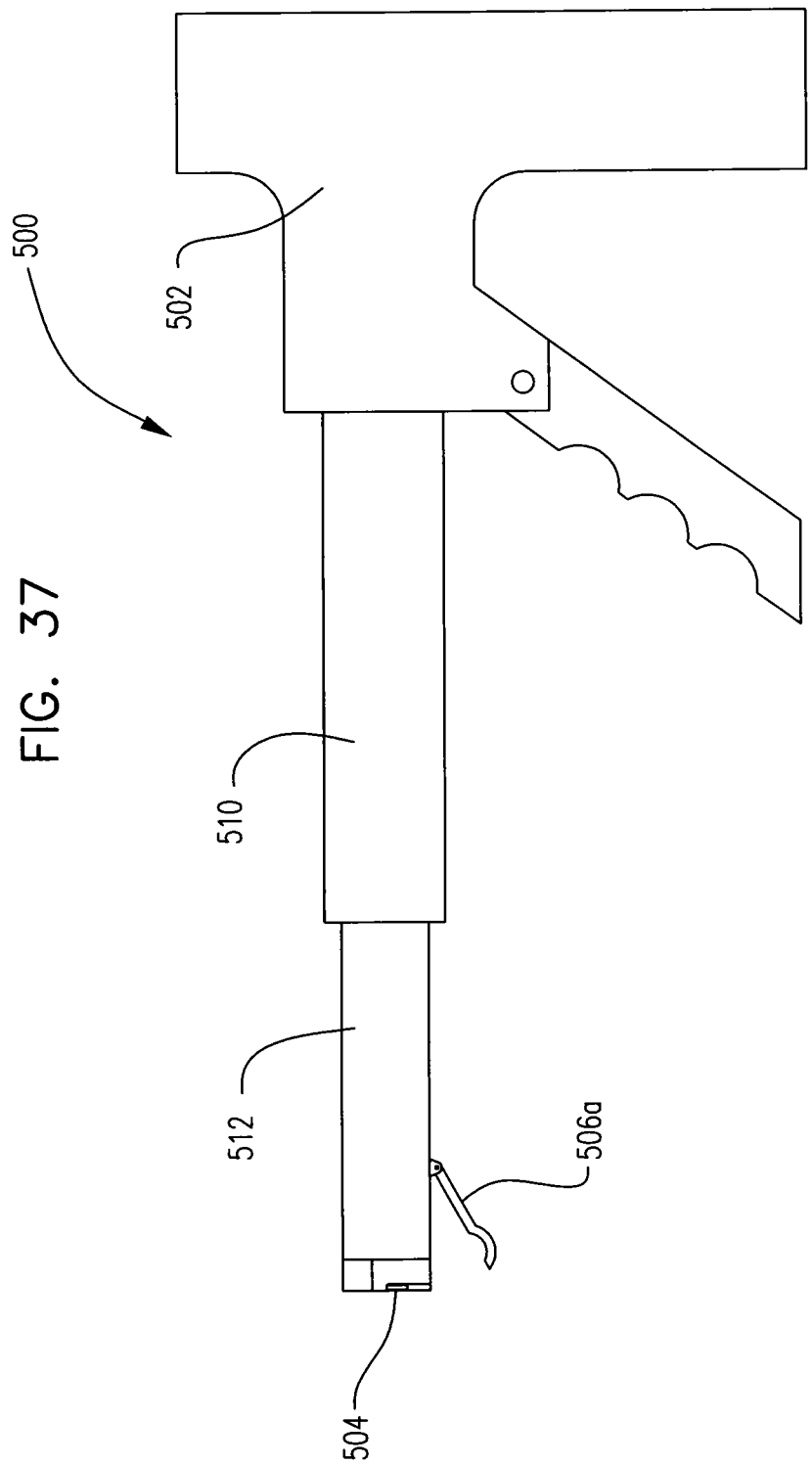
FIG. 37 is a side view of an embodiment of a tissue fastening device.
Figure 38:
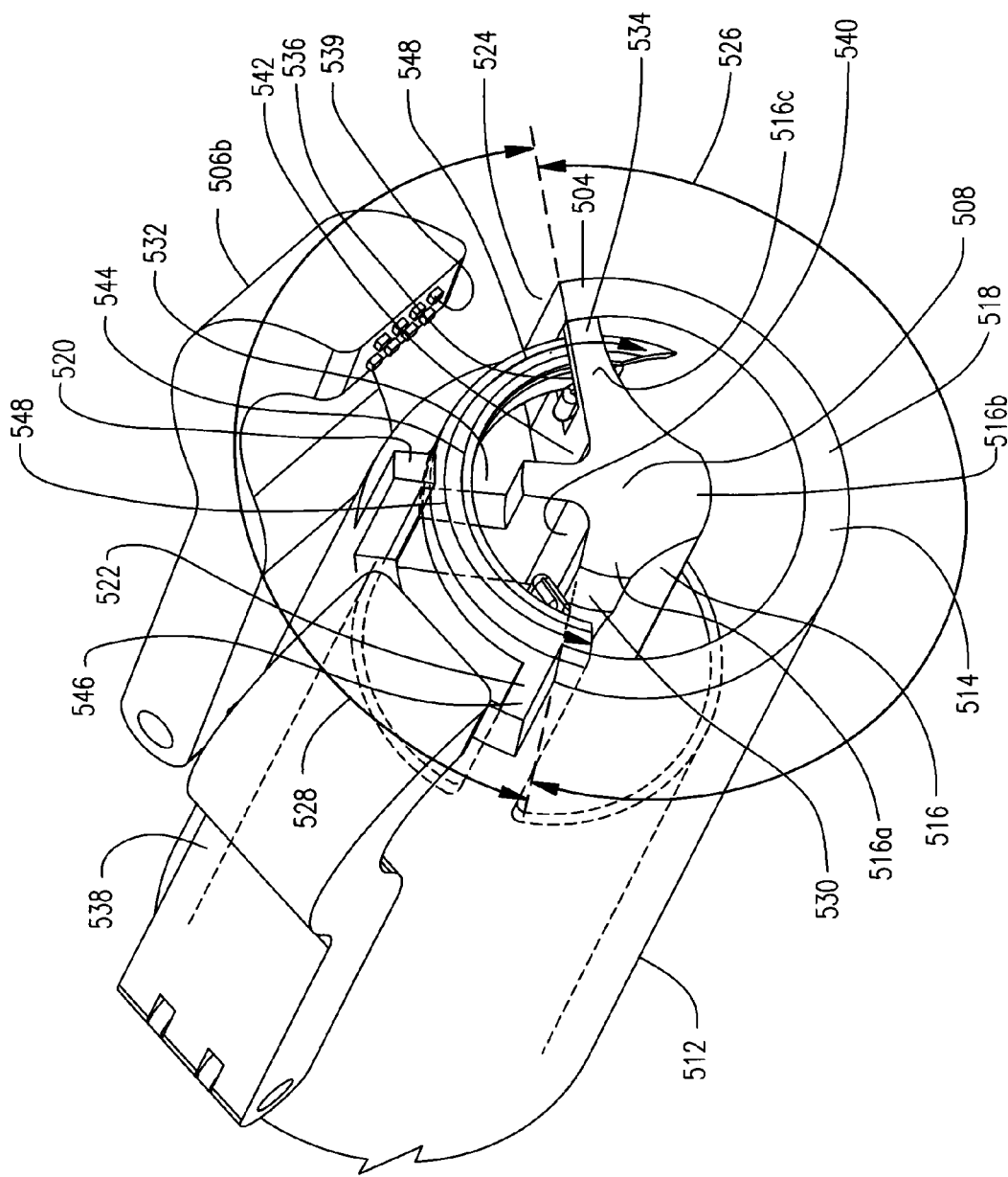
FIG. 38 is a perspective, end view of a fastening end of the tissue fastening device of FIG. 37.

Another representative embodiment of a tissue fastening device 500 of the present invention is illustrated in FIGS. 37 and 38. Tissue fastening device 500 can comprise generally similar features and components as tissue fastening device 200 so as to accomplish similar tissue capture and closure results. Tissue fastening device 500 can include a trigger style biasing end 502 for manipulating a fastening end 504. Tissue fastening device 500 can further comprise a pair of pivoting tissue capture members 506a, 506b for capturing and positioning tissue to be fastened within a tissue definition member 508. The tissue capture members 506a, 506b can be sequentially actuated during use through squeezing of the trigger style biasing end 502 or alternatively, by biasing a first body portion 510 over a second body portion 512 so as to force the approximation of the tissue capture members 506a, 506b with the tissue definition member 508.

As shown in FIG. 38, fastening end 504 is generally defined by an exterior body wall 514 and the tissue definition member 508. Tissue definition member 508 generally comprises a central projecting member 516 having a first projecting arm 516a, a second projecting arm 516b and a third projecting arm 516c. Exterior body wall 514 comprises a non-interrupted wall 518 and a wall separator 520. Cooperatively the non-interrupted wall 518 and wall separator 520 define a first wall gap 522 and a second wall gap 524. Non-interrupted wall 518 defines a wall arc 526 exceeding at least 180° while a tissue interface arc 528 defined by the first wall gap 522, second wall gap 524 and wall separator 520 is less than 180°. A first insertion gap 530 is defined between the non-interrupted wall 518 and the first projecting arm 516a. A second insertion gap 532 is defined between the wall separator 520 and the second projecting arm 516b. Third projecting arm 516c includes a gap cover 534 extending to the non-interrupted wall 518 so as to define an enclosed third insertion gap 536.

Figure 38A:
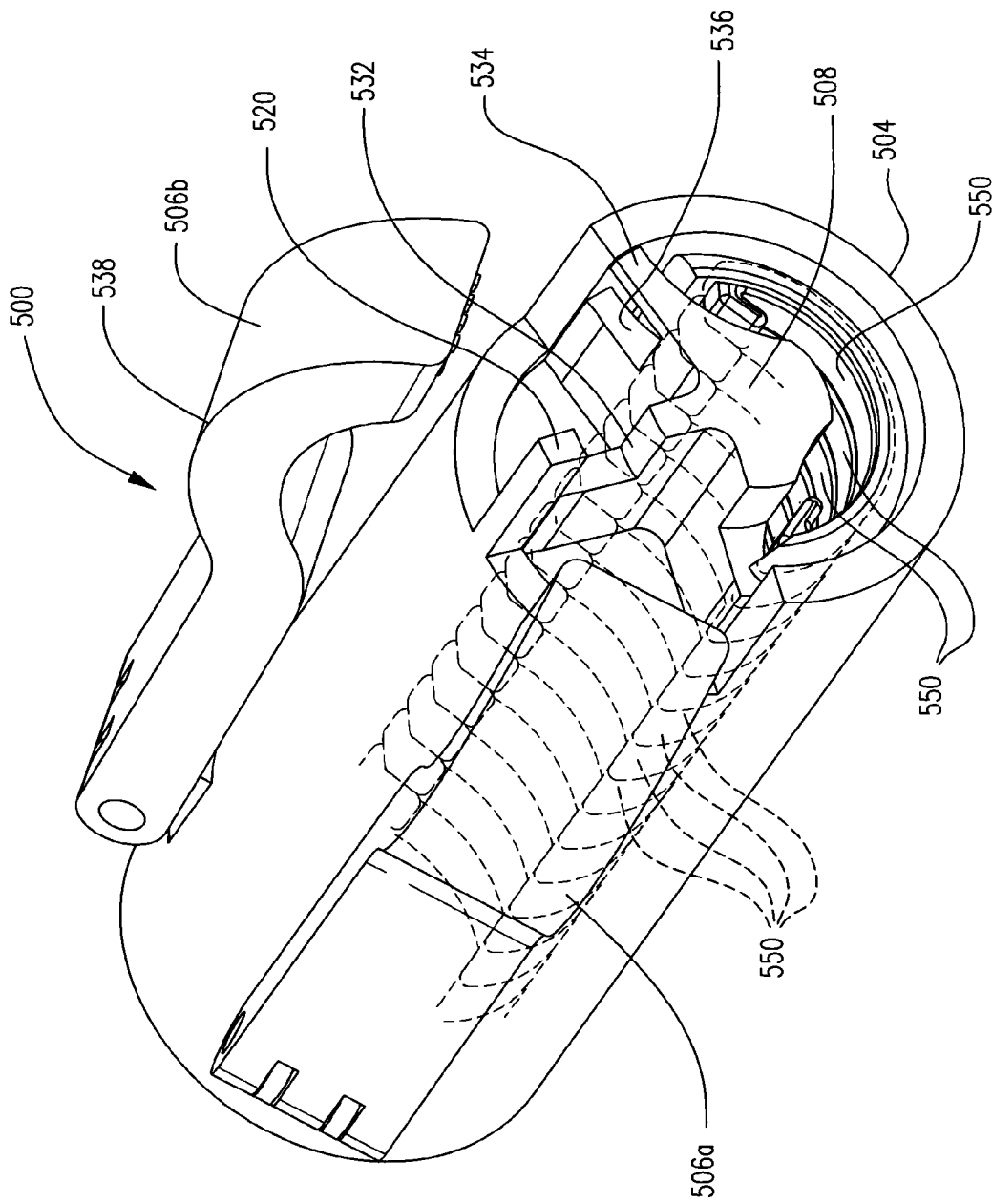
FIG. 38a is a perspective, end view of the fastening end of the tissue fastening device of FIG. 37 including a plurality of staged fasteners.

As depicted in FIGS. 38 and 38a, the tissue capture members 506a, 506b are illustrated in a substantially closed, tissue capturing disposition 538. Tissue capture members 506a, 506b can include one or more tissue gripping members 539 to promote tissue capture and retention during a fastening procedure. Tissue gripping members 539 can comprise a variety of configuration including, for example, barbs, projecting cubes, pyramids, rounded bumps and castles. In tissue capturing disposition 538, a first tissue capture area 540 is defined in the area bounded by the first insertion gap 530, the second insertion gap 532, tissue capture member 506a, first projecting arm 516a and second projecting arm 516b while a second tissue capture area 542 is defined in the area bounded by the second insertion gap 532, the enclosed third insertion gap 536, tissue capture member 506b, the second projecting arm 516b and the enclosed third insertion gap 536.

Figure 39:
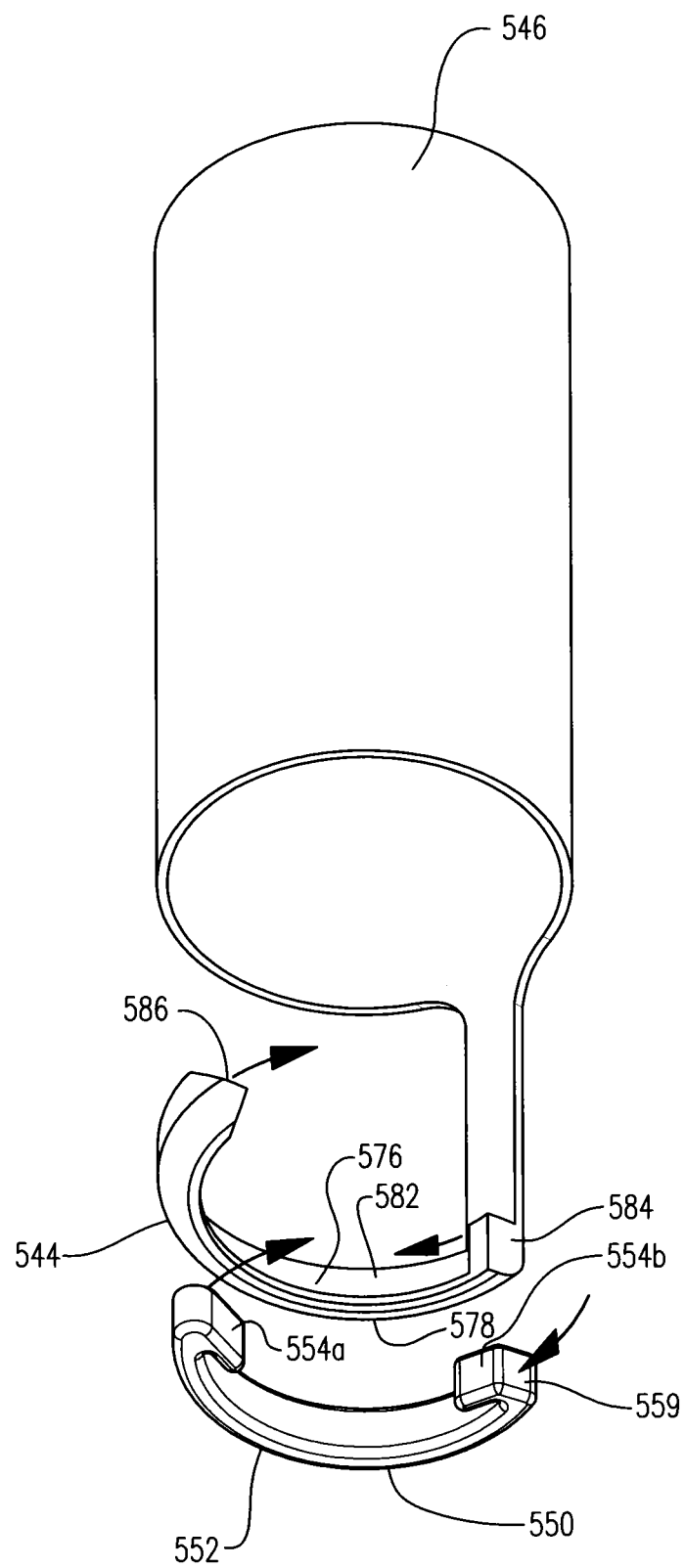
FIG. 39 is an exploded, perspective view of an insertion member and fastener of the tissue fastening device of FIG. 37.

With further reference to FIGS. 38 and 39, fastening end 504 of the tissue fastening device 500 further comprises a penetrator 544 operably attached to an insertion member 546. Both penetrator 544 and insertion member 546 can substantially resemble penetrator 242 and insertion member 210 as previously described with reference to tissue fastening device 200. Insertion member 546 is operably adapted to rotate within the exterior body wall 514 such that penetrator 544 is rotatably movable through a fastener insertion path 548 corresponding generally to the tissue interface arc 528 as will be described in detail below.

Figure 40:
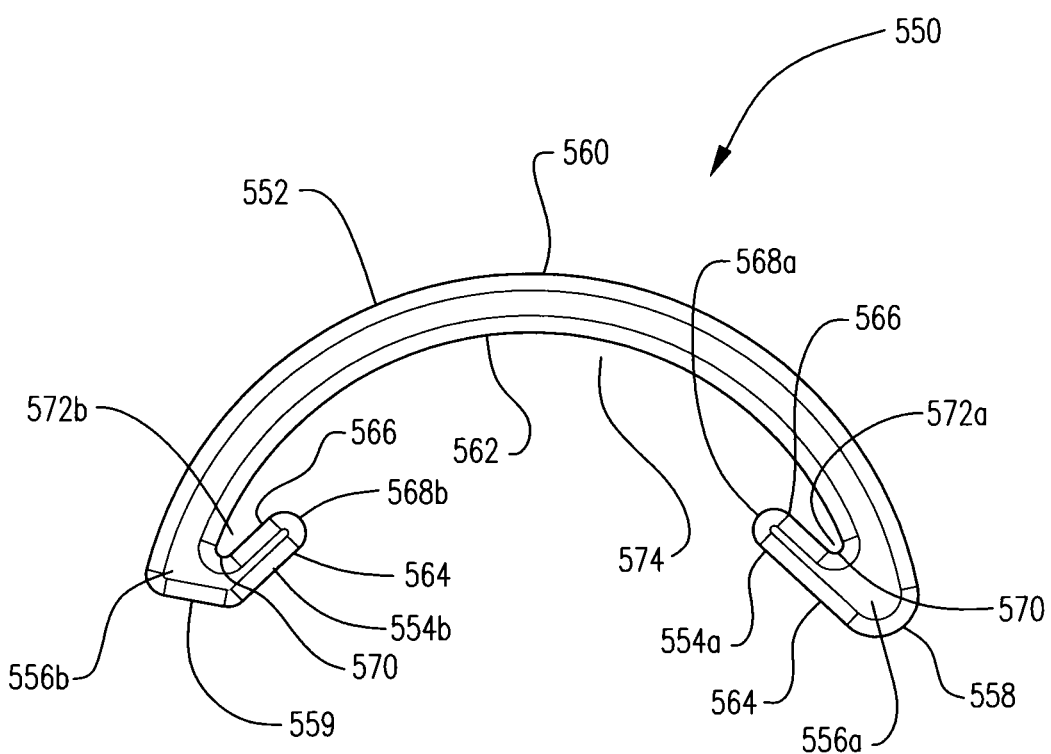
FIG. 40 is a top view of the fastener of FIG. 39.

Referring to FIGS. 39 and 40, an embodiment of a fastener 550 for use with penetrator 544 is illustrated. Fastener 550 can comprise similar components and fabrication techniques so as to provide fastener 550 with similar bioabsorption and dynamic transitioning capabilities as previously described with respect to fastener 124. While fastener 550 is generally described as comprising a bioabsorbable polymer such as, for example, the polymer and copolymer blends previously described with respect to fastener 124, it may be advantageous in certain surgical applications to utilize non-bioabsorbable materials such as, for example, stainless steel, nitinol and other medical grade alloys to fabricate fastener 550.

Generally, fastener 550 comprises an arcuate body portion 552 operably connecting a pair of internally projecting cleats 554a, 554b at elbow portions 556a, 556b. Elbow portion 556a can include a rounded elbow tip 558 while elbow portion 556b includes a fastener biasing surface 559. Arcuate body portion 552 can comprise a generally constant radius between the internally projecting cleats 554, 554b defining a fastener arc in the range of about 125° to about 165°. Arcuate body portion 552 is generally defined by an arcuate exterior, perimeter surface 560 and an arcuate interior surface 562. The arcuate shape of interior surface 562 functions to even out and focus fastener loading forces and reduces potential rocking of fastener 550 during tissue retention. Fastener 550 can have a generally constant cross-sectional appearance between elbow portions 556a, 556b. Internally projecting cleats 554a, 554b are generally defined by an outwardly facing cleat surface 564, an inwardly facing cleat surface 566 and rounded cleat tips 568a, 568b. Each inwardly facing cleat surface 566 connects to the interior surface 562 at a cleat base 570 so as to define a pair of durable tissue retention zones 572a, 572b. In combination, interior surface 562 and the inwardly facing cleat surfaces 566 define an initial tissue capture zone 574. Additional dimensional features of fastener 550 can substantially resemble fastener 124 as previously described including an effective fastener center line, elbow angles, fastener length, body width, fastener height, outwardly facing cleat surface length, cleat cross-sectional width, inwardly facing cleat surface length, cleat width and cleat gap.

Figure 40A:
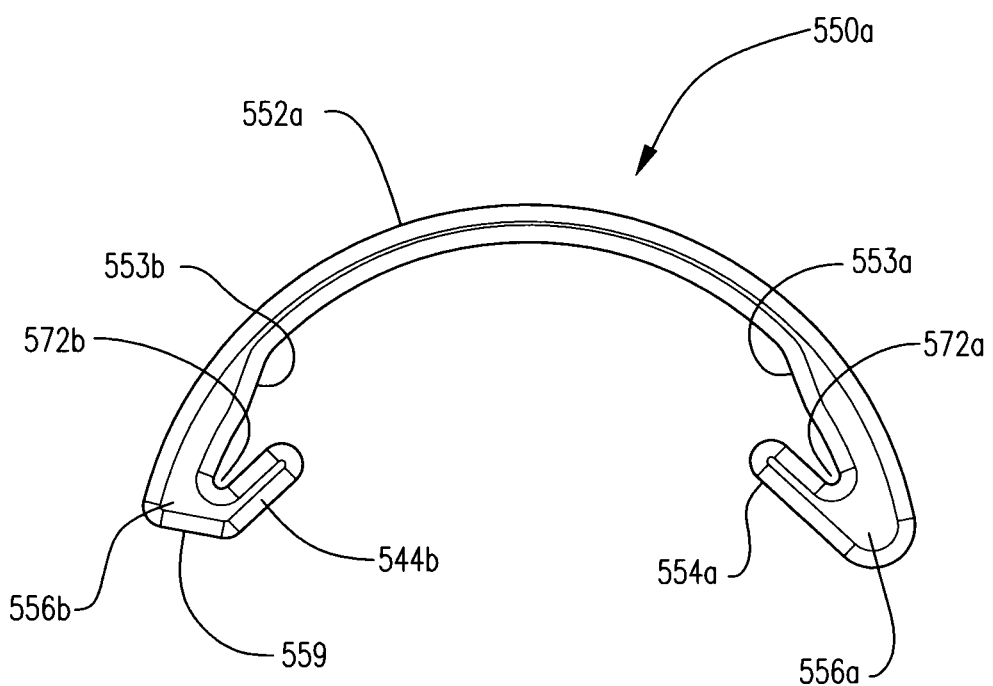
FIG. 40a is a top view an embodiment of a fastener for use with the tissue fastening device of FIG. 37 having a reduced thickness arcuate body portion.

As illustrated in FIG. 40a, an embodiment of a fastener 550a for use with the penetrator 544 can substantially resemble fastener 550 with the exception of a reduced thickness arcuate body portion 552a operably connecting internally projecting cleats 554a, 554b at elbow portions 556a, 556b. Internally projecting cleats 554a, 554b and elbow portions 556a, 556b have increased thicknesses allowing the fastener 550a to retain strength in areas such as, for example, the durable tissue retention zones 572a, 572b, that are most effected by wound stress during healing. The reduced sectional profile of reduced thickness arcuate body portion 552a transitions to the increased profile of the elbow portions 556a, 556b at a pair of transition zones 553a, 553b. As reduced thickness arcuate body portion 552 has a reduced cross-sectional profile, less bioabsorbable material is required during fabrication. Reducing the amount of bioabsorbable material in fastener 550a can significantly reduce the cost of manufacturing each fastener 550a while at the same time being less irritating to captured tissue. In addition, reducing the cross-sectional profile of reduced thickness arcuate body portion 552 can be advantageous as fastener 550a is generally more flexible than fastener 550, allowing fastener 550a to more readily adapt to tissue stress and quickly assume a tensile mode.

Figure 39A:
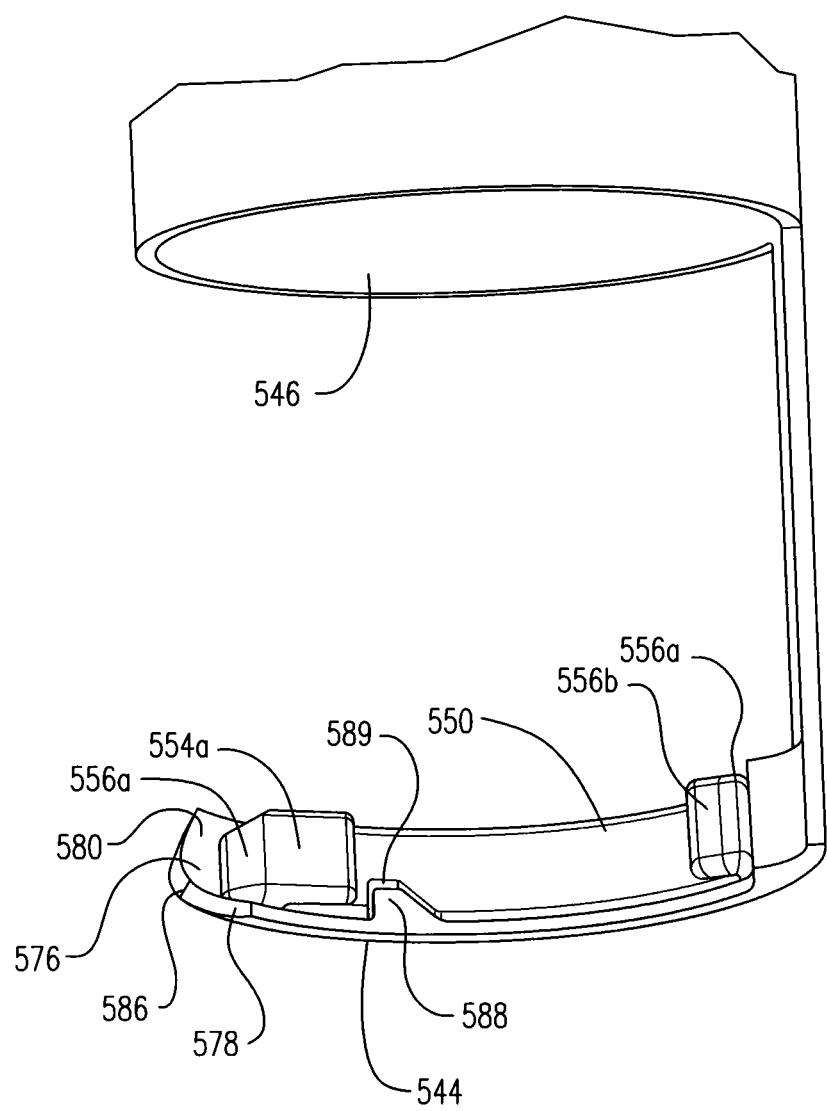

Referring again to FIG. 39, fastener 550 generally resides within a fastener holding portion 576 on the penetrator 544 defined by a bottom penetrator surface 578, a radial exterior wall surface 580, a radial inner surface 582 and a biasing wall 584. Fastener 550 is positioned within the fastener holding portion 576 such that the arcuate body portion 552 lies against the bottom penetrator surface 578 and the radial exterior wall surface 580 with the elbow portion 556a proximate a penetrator piercing end 586 and the fastener biasing surface 559 positioned against the biasing wall 584. Through the interface of biasing wall 584 and the fastener biasing surface 559, fastener 550 is forcibly carried with penetrator 544 as insertion member 546 rotates with respect to fastening end 504 such that fastener 550 is carried through the fastener insertion path 548. In addition to or alternatively to using the interaction of biasing wall 584 and fastener biasing surface 559 to carry fastener 550, penetrator 544 can comprise a projecting member 588 within the fastener holding portion 576 for engaging a notched section 589 on the fastener 550 so as to carry fastener 550 with the penetrator 544 as illustrated in FIG. 39a. The interaction of projecting member 588 and notched section 589 can provide an additional benefit of properly aligning the fastener 550 within the fastener holding portion 576, which may be especially useful when tissue fastening device 500 comprises a plurality of staged fasteners 550.

Use of tissue fastening device 500 for closure of a tissue wound is illustrated sequentially in FIGS. 41-47. As presently discussed, tissue fastening device 500 is described with reference to closure of a skin wound for illustrative purposes though it will be understood that tissue fastening device 500 is similarly applicable to a variety of related tissue closure and/or joining applications. Due to the rotatable insertion nature of fastener 550, fastening end 504 can be positioned in a wide range of angular orientations with respect to the opening 100 allowing fastener 550 to access the target tissue zones 122 in a variety of angular orientations with respect to the exterior surface 116 of the skin tissue 102.

Figure 41:
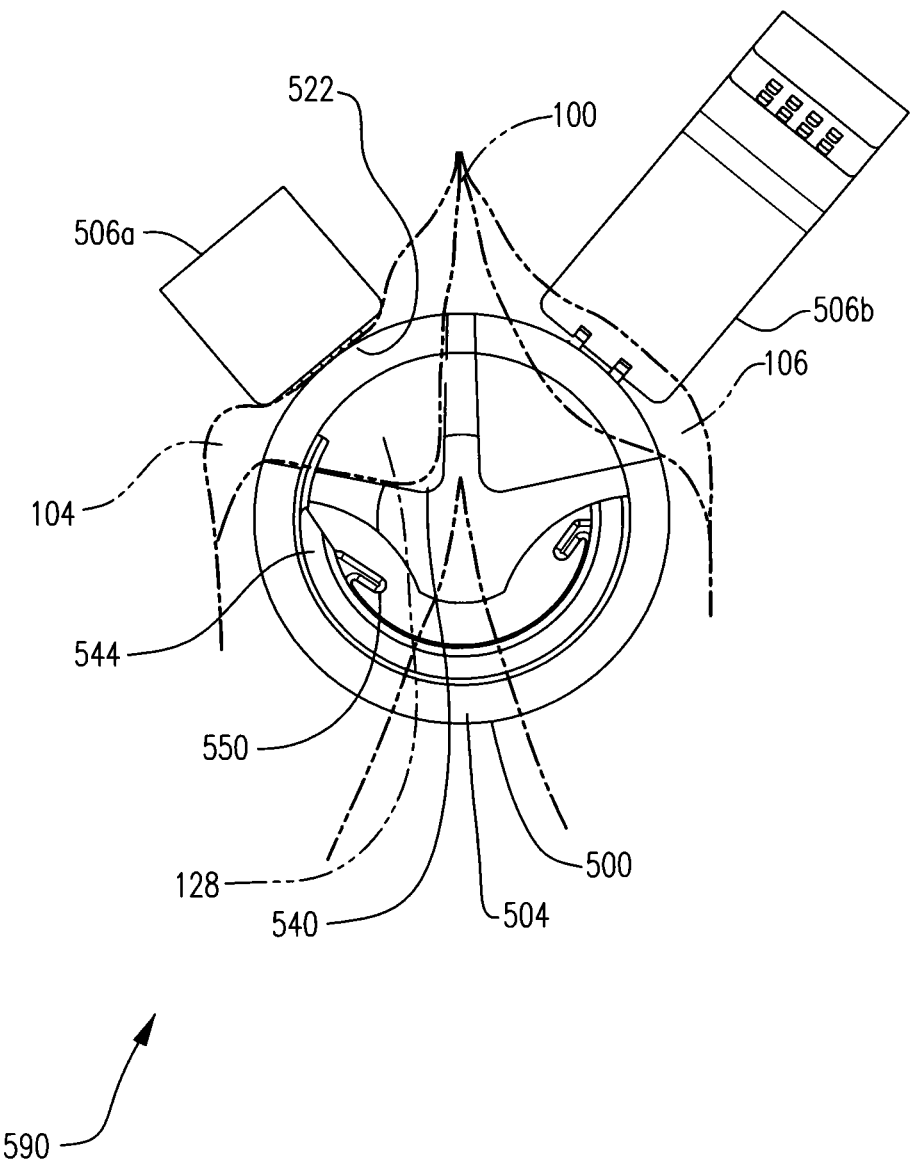
FIG. 41 is an end view of the fastening end of the tissue fastening device of FIG. 37 during a first fastening step for closing a skin wound.

Referring to FIG. 41, a first fastening step 590 generally comprises positioning fastening end 504 within opening 100. Using the trigger style biasing end 502, the tissue capture member 506a is biased closed such that it resides proximate the first wall gap 522. As tissue capture member 506a approaches the first wall gap 522, first side 104 is grasped and squeezed such that the first target tissue zone 128 is presented, retained and defined within the first tissue capture area 540. As first side 104 is captured within first tissue capture area 540, penetrator 544 and fastener 550 remain positioned fully within the wall arc 526.

Figure 42:
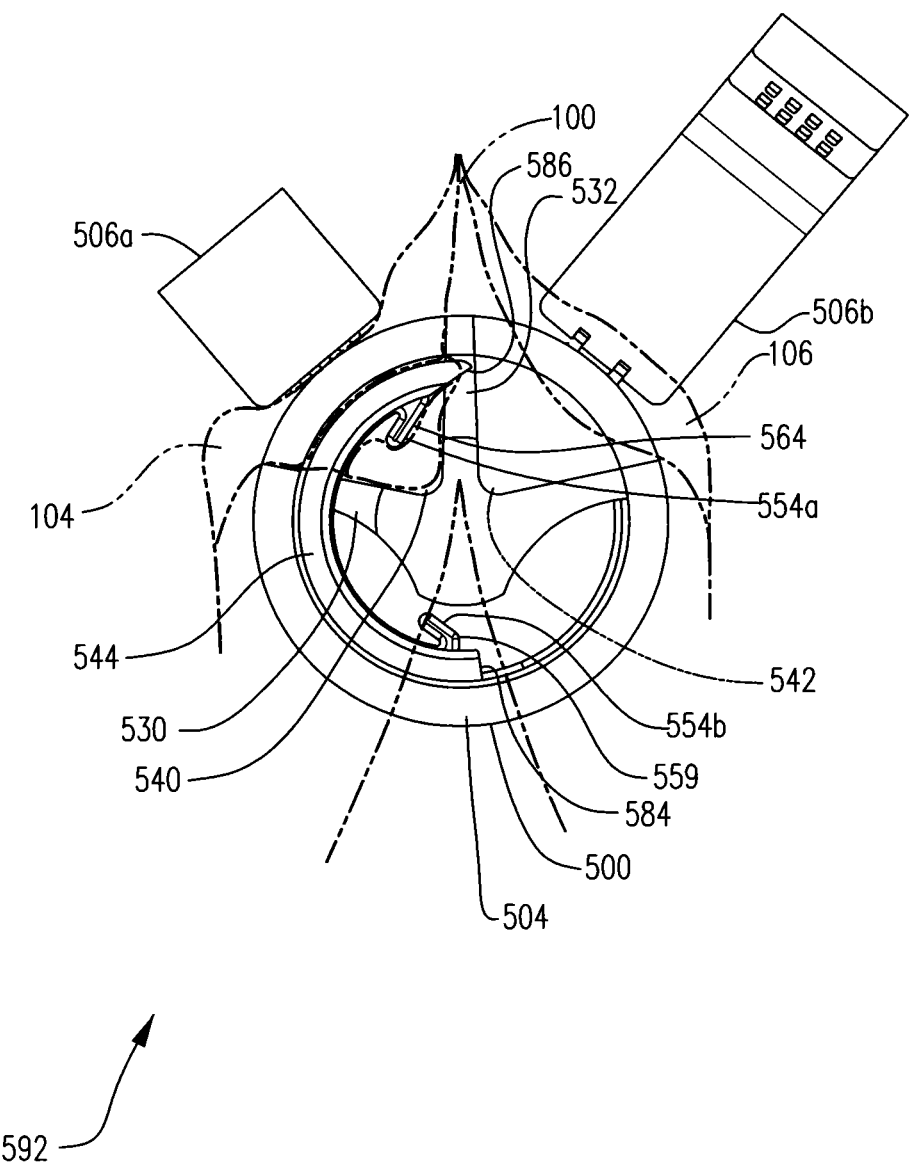
FIG. 42 is an end view of the fastening end of the tissue fastening device of FIG. 37 during a second fastening step for closing a skin wound.

Following the positioning of the first side 104 within the first tissue capture area 540, further biasing of the trigger style biasing end 502 initiates rotation of the insertion member 546 and correspondingly, penetrator 544 such that piercing end 586 rotates through the first insertion gap 530 and commences rotational travel along the tissue interface arc 528 during a second fastening step 592 as illustrated in FIG. 42. As piercing end 586 rotates along the tissue interface arc 528, the piercing end 586 cuts through the dermal layer 118 of captured first side 104. As piercing end 586 rotatably traverses the first tissue capture area 540, internally projecting cleat 554a is carried through the dermal layer 118. As the cross-sectional width of the internally projecting cleat 554a exceeds the cross-sectional width of the piercing end 586 and the penetrator 544, the first side 104 essentially piles up along the outwardly facing cleat surface 564 until the internally projecting cleat 554a approaches and enters the second insertion gap 532 wherein the first side 104, still captured and retained by tissue capture member 506a is elastically stretched and pulled over the internally projecting cleat 554a such that the arcuate body portion 552 of fastener 550 resides within a pierced opening of the first side 104.

Figure 43:
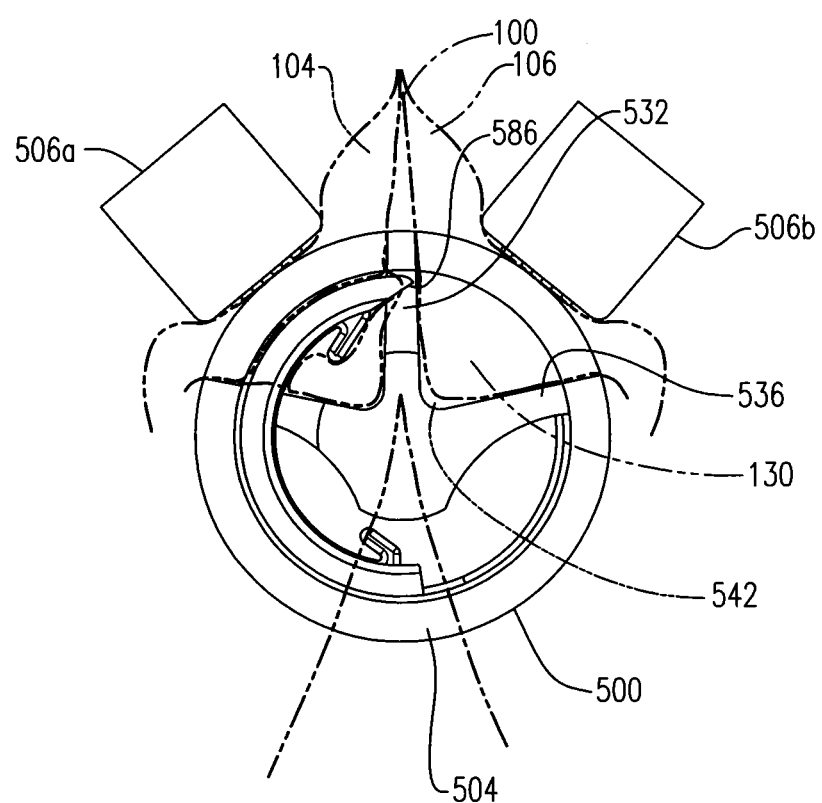
FIG. 43 is an end view of the fastening end of the tissue fastening device of FIG. 37 during a third fastening step for closing a skin wound.

Once piercing end 586 reaches the second insertion gap 532, further biasing of the trigger style biasing end 502 causes tissue capture member 506b to close such that it resides proximate the second wall gap 524 in a third fastening step 594 as illustrated in FIG. 43. As tissue capture member 506b approaches the second wall gap 524, second side 106 is grasped and squeezed such that the second target tissue zone 130 is presented, retained and defined within the second tissue capture area 542. As second side 106 is captured within second tissue capture area 542, piercing end 586 remains positioned within the second insertion gap 532 so as to not interfere with the capture of second side 106.

Figure 44A:
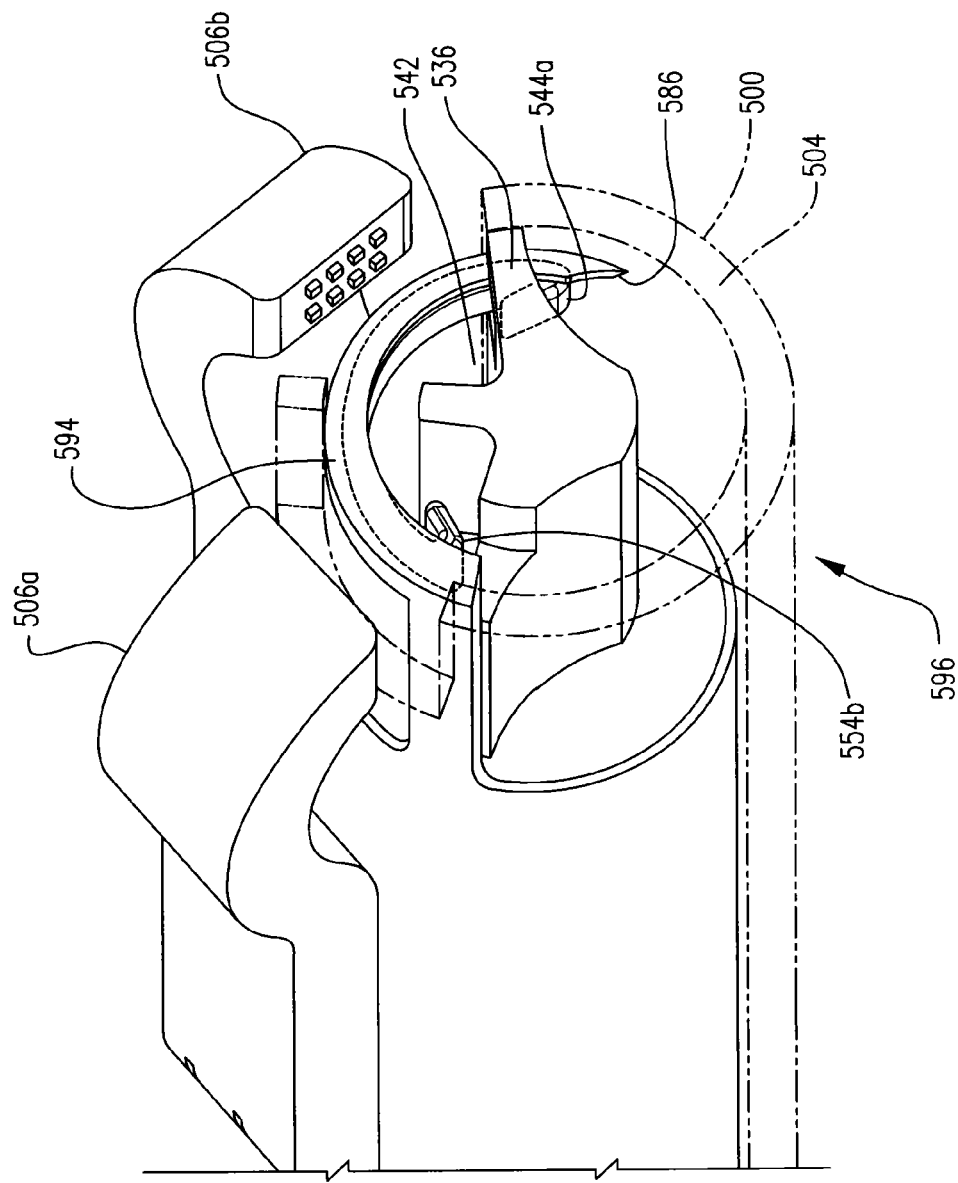
FIG. 44a is a perspective end view of the fastening end of the tissue fastening device of FIG. 37 during the fourth fastening step of FIG. 44.

Once the second target tissue zone 130 is defined within the second tissue capture area 542, further biasing of the trigger style biasing end 502 causes piercing end 586 to commence rotational travel through the second tissue capture area 542 during a fourth fastening step 596 as illustrated in FIGS. 44 and 44a. As piercing end 586 rotates along the tissue interface arc 528, the piercing end 586 cuts through the dermal layer 118 of captured second side 106. As the internally projecting cleat 554a is carried through the second tissue capture area 542, the second side 106 piles up along the outwardly facing cleat surface 564 until the internally projecting cleat 554a approaches and enters the enclosed third insertion gap 536. As piercing end 586 and consequently, the internally projecting cleat 564a enter the enclosed third insertion gap 536, the piercing end 586 and internally projecting cleat 564a leave the tissue interface arc 528 and enter the wall arc 526. As internally projecting cleat 564a begins traversing the wall arc 526, rounded cleat tip 568a enters the enclosed third insertion gap 536 such that the second side 106 which has been piled along the outwardly facing cleat surface 564 is elastically stretched and forced over the internally projecting cleat 564a by the enclosed third insertion gap 536. At the same time that internally projecting cleat 564a traverses the second tissue capture area 542, internally projecting cleat 564b is advanced into the first tissue capture area 540 wherein the internally projecting cleat 564b essentially acts as an anchor and captures first side 104 within the durable tissue retention zone 572b. As first side 104 is in an elastically stretched condition due to its initial capture by internally projecting cleat 564a, first side 104 is elastically retained within the durable tissue retention zone 572b and cannot escape capture by the internally projecting cleat 564b.

Figure 45:
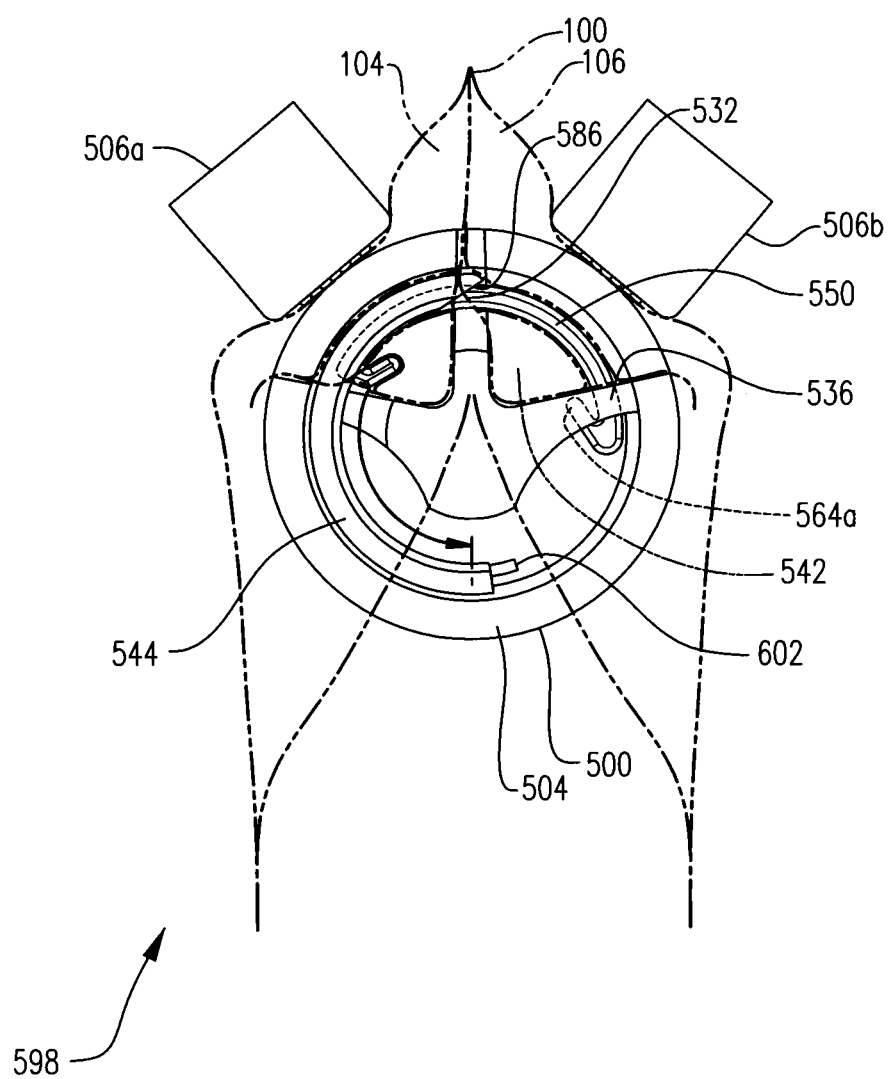
FIG. 45 is an end view of the fastening end of the tissue fastening device of FIG. 37 during a fifth fastening step for closing a skin wound with a first internally projecting cleat located within a third insertion gap.
Figure 45A:
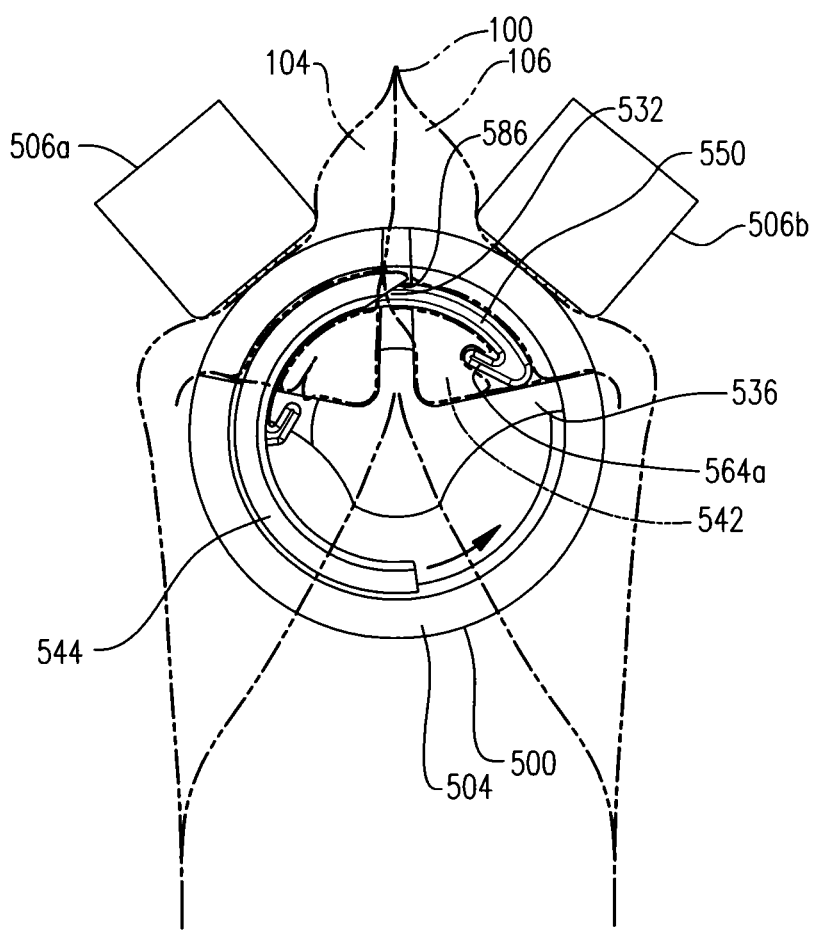
FIG. 45a is an end view of the fastening end of the tissue fastening device of FIG. 37 during a fifth fastening step for closing a skin wound with a first internally projecting cleat located with a second tissue capture zone.

Once the piercing end 586 and internally projecting cleat 564a have passed fully into the enclosed third insertion gap 536 and the second side 106 has been elastically stretched over the internally projecting cleat 564a, the trigger style biasing end 502 can be released so as to initiate a reverse rotation of the insertion member 546, and consequently, the penetrator 544 in a fifth fastening step 598 as illustrated in FIGS. 45 and 45a. Penetrator 544 is rotatably withdrawn through the tissue interface arc 528 such that piercing end 586 resides within the second insertion gap 532. As piercing end 586 is withdrawn through the second tissue capture area 542, fastener 550 is preferably slightly withdrawn as depicted in FIG. 45a such that the internally projecting cleat 564a exits the enclosed third insertion gap 536. However, in some closure and attachment locations, fastener 550 may remain essentially stationary such that internally projecting cleat 564a continues to reside within enclosed third insertion gap 536 as shown in FIG. 45 even as the penetrator 544 is rotatably withdrawn.

Figure 46:
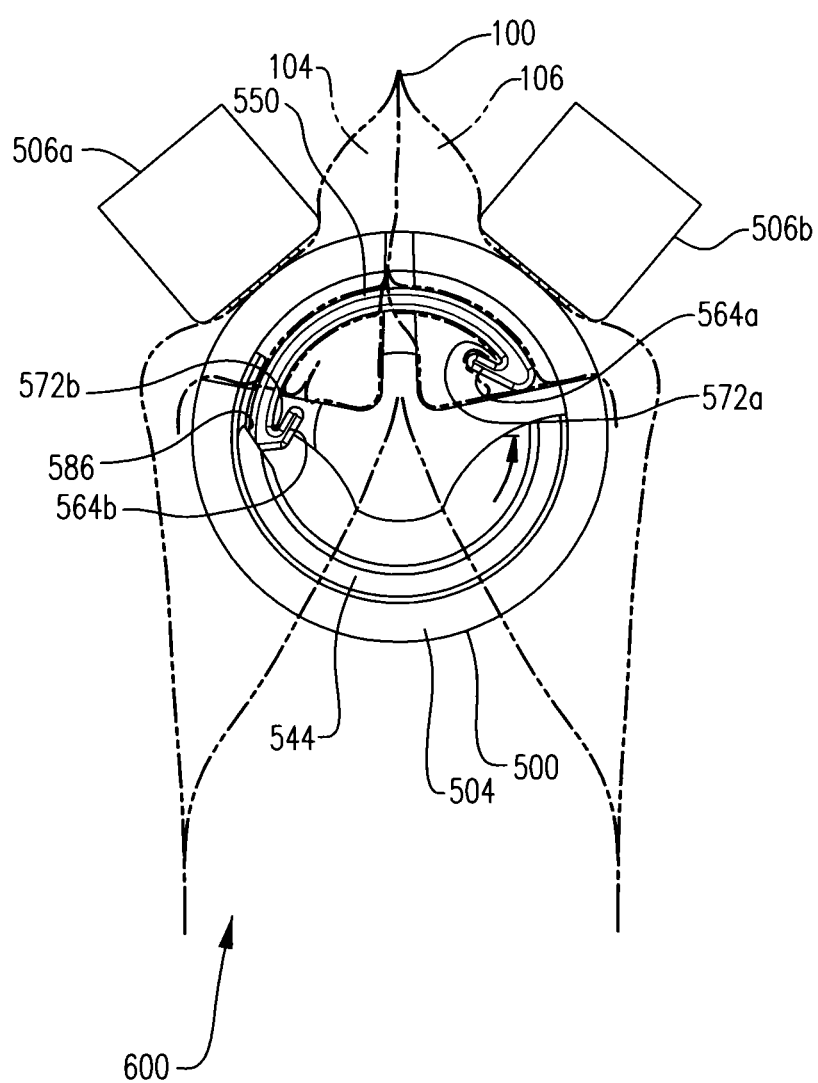
FIG. 46 is an end view of the fastening end of the tissue fastening device of FIG. 37 during a sixth fastening step for closing a skin wound.

During a sixth fastening step 600 as illustrated in FIG. 46, the penetrator 544 is fully withdrawn such that it resides solely within the wall arc 526, the capture of first side 104 and second side 106 with fastener 550 is completed with the first side 104 elastically captured within the second durable retention zone 572b and the second side 106 elastically captured within the first durable retention zone 572a. If when penetrator 544 fully resides within the wall arc 526, the internally projecting cleat 564a remains within the enclosed third insertion gap 536 as shown in FIG. 45, a trailing penetrator member 602 as shown in FIG. 45 can be used to bump internally projecting cleat 564a from the enclosed third insertion gap 536.

Figure 47:
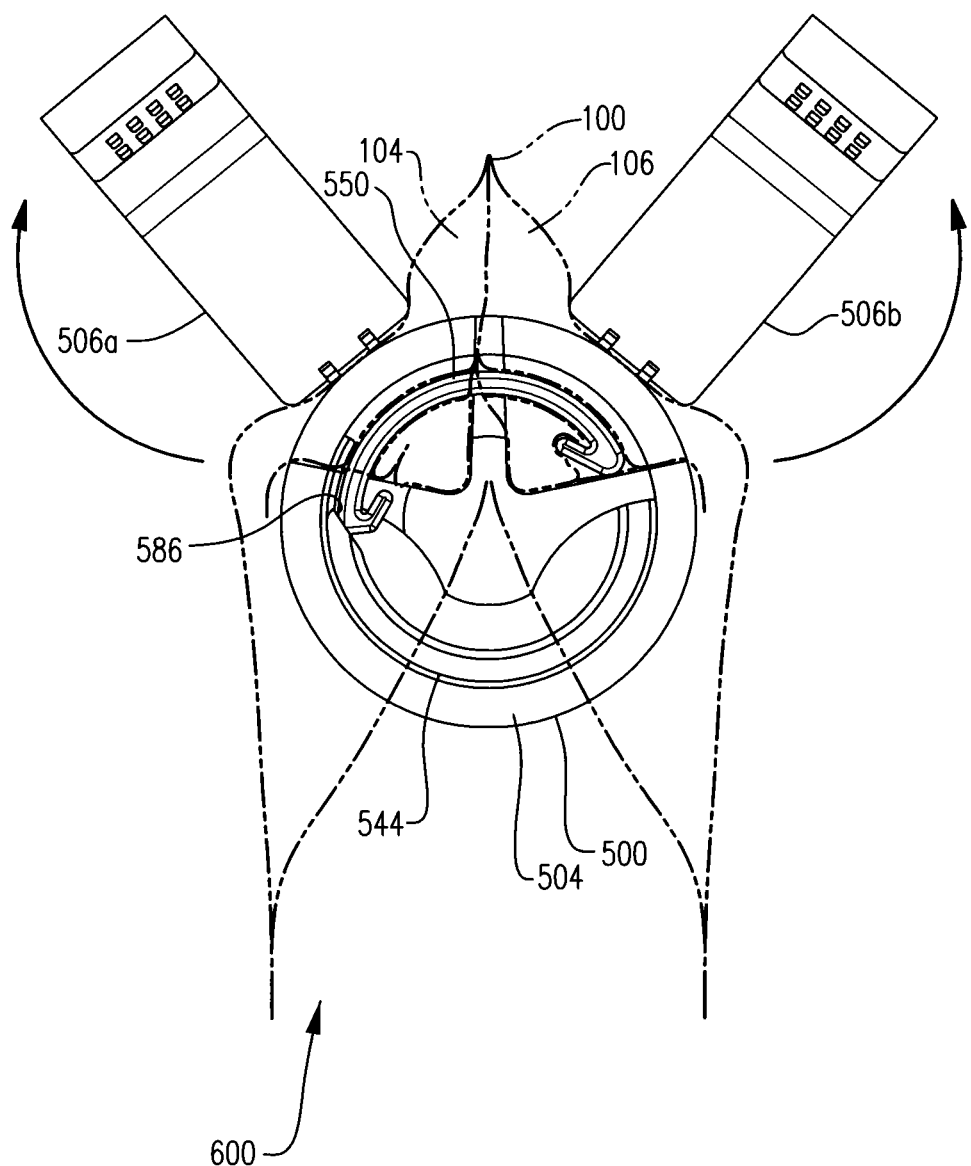
FIG. 47 is an end view of the fastening end of the tissue fastening device of FIG. 37 during a seventh fastening step for closing a skin wound.
Figure 48:
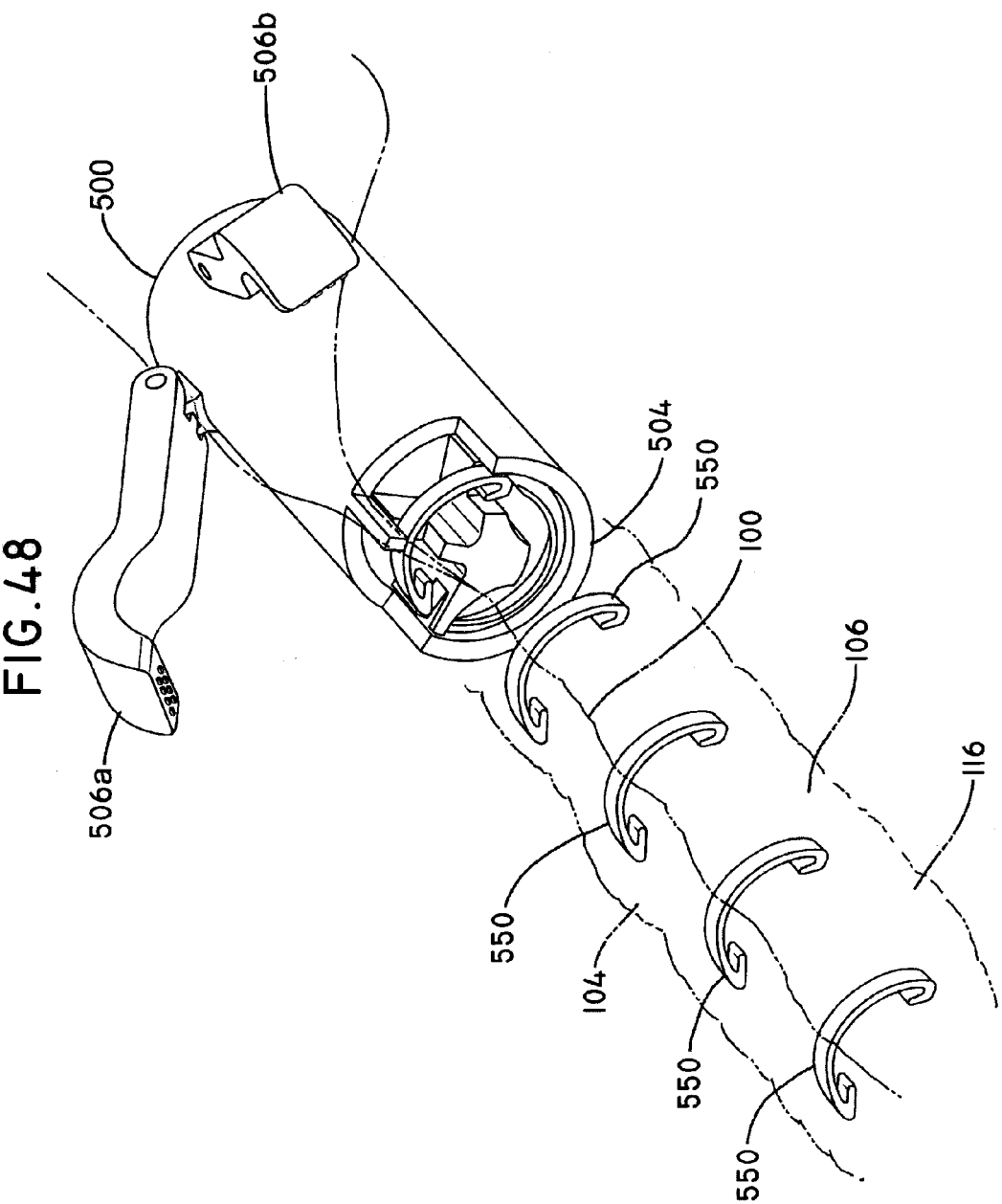
FIG. 48 is a perspective view of the tissue fastening device of FIG. 37 being repositioned in a skin wound for deployment of the fastener of FIG. 40.
Figure 49:
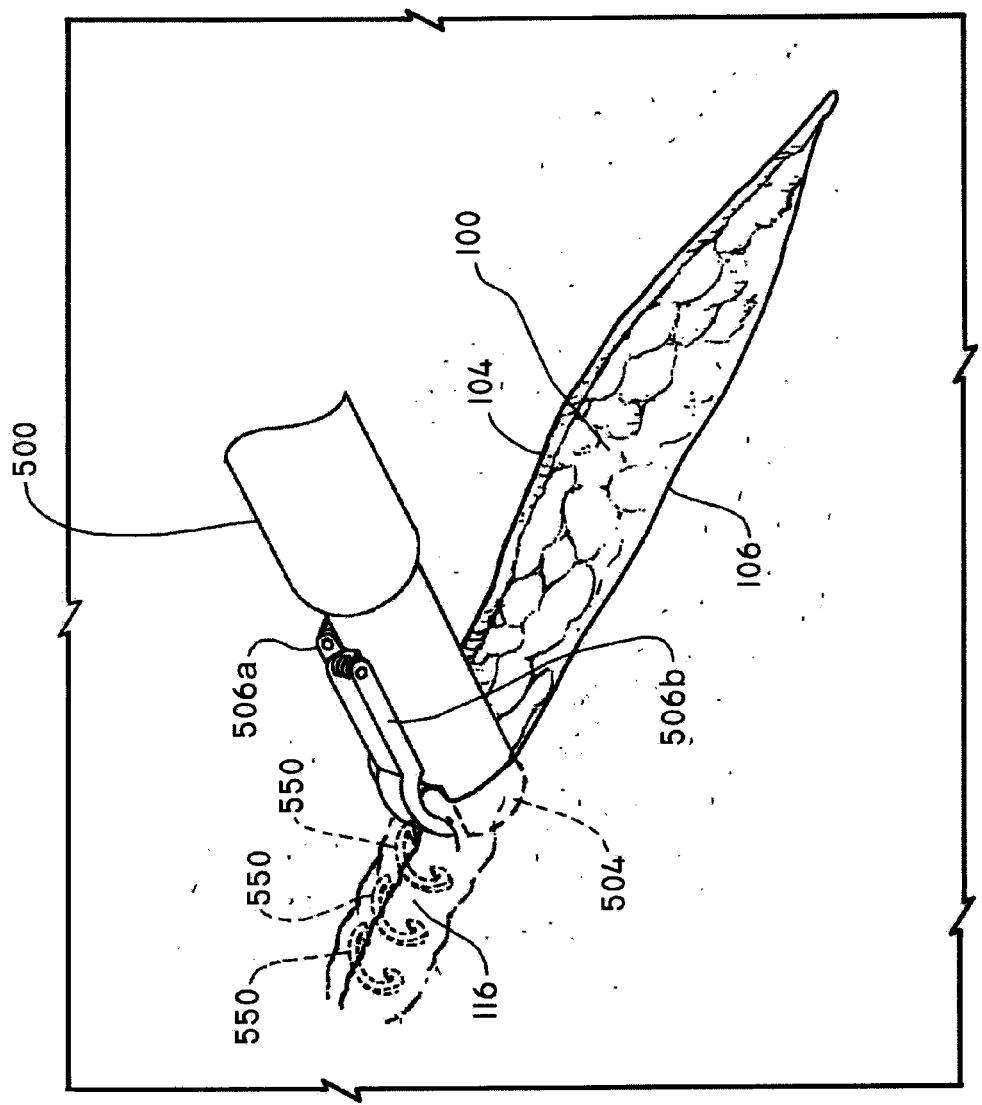
FIG. 49 is a perspective view of the tissue fastening device of FIG. 37 deploying the fastener of FIG. 40 to close a skin wound.
Figure 50:
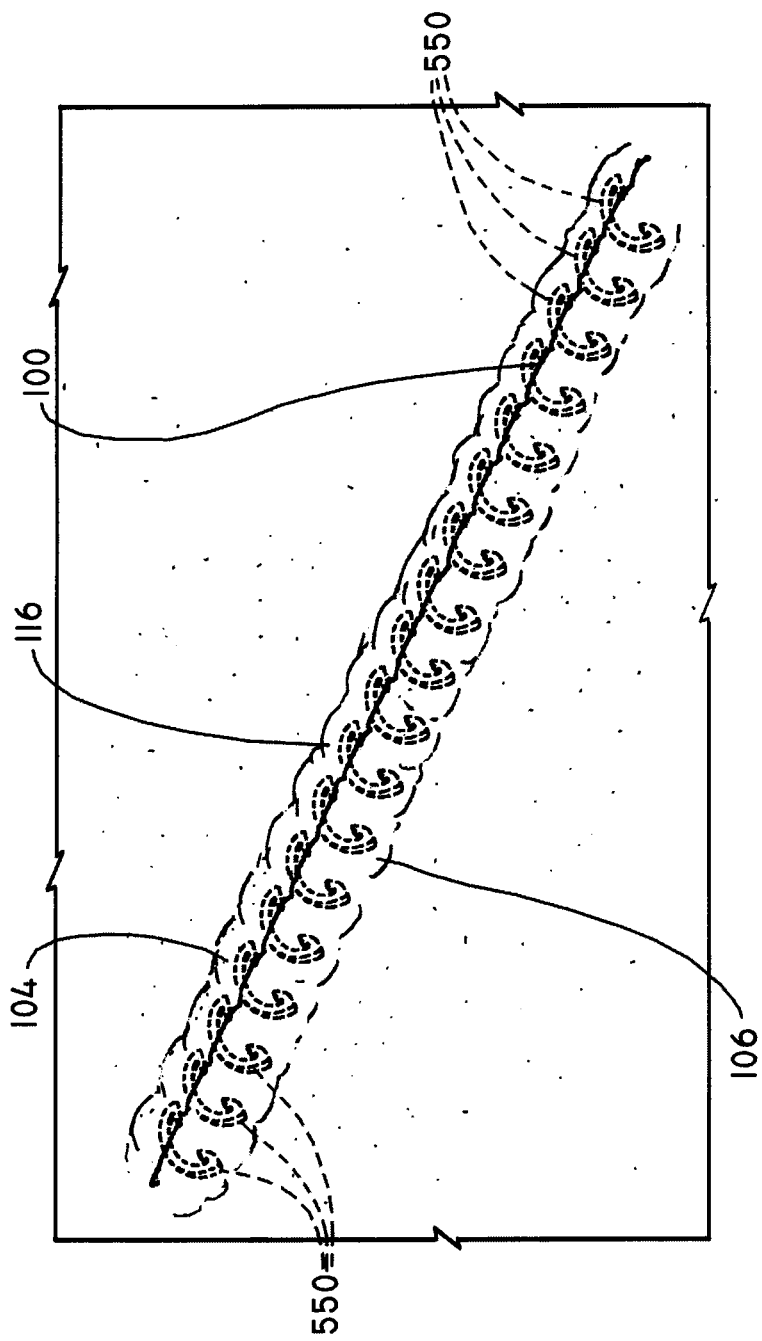
FIG. 50 is a perspective view of an everted wound closure being closed with a plurality of the fasteners of FIG. 40.

Finally, tissue capture members 506a, 506b are withdrawn during a seventh fastening step 604 illustrated in FIG. 47 such that tissue fastening device 500 can be lifted from the opening 100 and first side 104 and second side 106 are retainably held by fastener 550. Following seventh fastening step 604, the fastening process can be repeated by repositioning tissue fastening device 500 as shown in FIGS. 48 and 49 at a next desired fastening location along opening 100 if tissue fastening device 500 includes additional fasteners 550 as illustrated in FIG. 38a. As illustrated in FIGS. 48, 49 and 50, tissue fastening device 500 has been utilized to close skin opening 100 with a plurality of fasteners 550 in a generally downwardly facing, non-parallel orientation with respect to exterior surface 116. Fasteners 550 retain first side 104 and second side 106 in the generally everted disposition most advantageous for wound healing.

Due to the flexibility of tissue fastening device 500, fastener 550 can be deployed in almost any orientation ranging from substantially parallel to substantially perpendicular with respect to the exterior surface 116 of first side 104 and second side 106. Due to the flexibility of the placement orientation of fasteners 550 within first side 104 and second side 106, a medical professional is provided the option of varying the spacing between adjacent fasteners allowing the medical professional to selectively increase the overall closure strength along the length of opening 100 by placing adjacent fastener 550 in close proximity, which may be especially advantageous in either high-stress wound locations or for larger wounds. As best illustrated in FIG. 50, the placement of a plurality of fasteners 550 to close wound 100 essentially simulates a wound closure accomplished using a running, subcuticular suture with the added benefit of each fastener 550 being interrupted so as to reduce the potential for infection and inflammation which can be communicated along the continuous length of a running, subcuticular suture.

As illustrated in FIG. 51, the closure principles disclosed in the aforementioned apparatus and method embodiments are applicable to and can be utilized to form a minimally invasive tissue fastening device 700. Similar to tissue fastening devices 200 and 500, minimally invasive tissue fastening device 700 can comprise a biasing portion 702 and an insertion portion 704. Minimally invasive tissue fastening device 700 can further comprise an extended body portion 706 allowing the insertion portion 704 to be inserted through a body wall, such as, for example, an abdominal wall 708 such that insertion portion 704 can fasten tissue within the abdomen 710. Extended body portion 706 can be adapted for direct insertion through the abdominal wall 708 or alternatively, an extended body portion 706 can be inserted through a laproscopic port in the abdominal wall. Biasing portion 702 generally remains outside the body allowing a user to manipulate insertion portion 704 to capture and secure tissue in a manner similar to that previously described with respect to tissue fastening devices 200 and 500. However, tissue fastening device 700 may be used in internal applications wherein the positioning, joining and anchoring of tissue or organ does not suffer the disadvantage associated with "buttonholing" or piercing the epidermis during skin tissue closure. As such, tissue capture using minimally invasive tissue fastening device 700 may, in some treatment applications, have less criticality with respect to tissue capture with insertion portion 704.

While various representative embodiments of the present invention have been described with respect to fastening of dermal tissue, it will be recognized that the present invention is also applicable to other types of tissue having membranes walls or layers such as facia, muscle and the like.

Although the present invention has been described with respect to a variety of representative, presently contemplated embodiments, it will be understood that numerous insubstantial changes in configuration, arrangement or appearance of the elements of the present invention can be made without departing from the intended scope of the present invention. Accordingly, it is intended that the scope of the present invention be determined by the claims as set forth.

The invention claimed is:

1. A method for sequentially capturing adjacent tissue with a fastener comprising:
providing a medical apparatus that includes a falcate penetrator adapted to pierce tissue along a generally arc-shaped path of travel, the falcate penetrator having a maximum cross-section dimension transverse to the path of travel;
providing a discrete fastener adapted to be carried by the falcate penetrator and having a first capture portion and a second capture portion proximate generally opposing ends of the fastener, each capture portion of the fastener having a maximum cross-section dimension transverse to the path of travel of the falcate penetrator that is greater than the maximum cross-section dimension of the falcate penetrator;
piercing a first tissue portion with the falcate penetrator, the falcate penetrator operably carrying a first capture portion of the fastener though the first tissue portion wherein the first tissue portion is caused to stretch over the first capture portion of the fastener due to the first capture portion cross-section dimension exceeding the falcate penetrator cross-section dimension;
piercing a second tissue portion with the falcate penetrator such that the first capture portion of the fastener is advanced through the second tissue portion, wherein the second tissue portion is caused to stretch over the first capture portion of the fastener due to the first capture portion cross-section dimension exceeding the falcate penetrator cross-section dimension, while a second capture portion of the fastener operably engages the first tissue portion; and
removing the falcate penetrator from the first tissue portion and the second tissue portion without causing the fastener to be withdrawn such that the fastener retainably captures the first tissue portion and the second tissue portion with the first portion of the fastener operably engaging the second tissue portion and the second portion of the fastener operably engaging the first tissue portion.

2. The method of claim 1, wherein the step of removing the falcate penetrator is accomplished by withdrawing the falcate penetrator back along the path of travel.

* * * * *